(12) United States Patent
Romesberg et al.

(10) Patent No.: US 12,173,291 B2
(45) Date of Patent: Dec. 24, 2024

(54) UNNATURAL BASE PAIR COMPOSITIONS AND METHODS OF USE

(71) Applicant: THE SCRIPPS RESEARCH INSTITUTE, La Jolla, CA (US)

(72) Inventors: Floyd E. Romesberg, La Jolla, CA (US); Michael P. Ledbetter, La Jolla, CA (US); Rebekah J. Karadeema, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 1056 days.

(21) Appl. No.: 16/913,226

(22) Filed: Jun. 26, 2020

(65) Prior Publication Data
US 2020/0318122 A1    Oct. 8, 2020

Related U.S. Application Data

(63) Continuation of application No. PCT/US2018/067969, filed on Dec. 28, 2018.

(60) Provisional application No. 62/612,062, filed on Dec. 29, 2017.

(51) Int. Cl.
| | |
|---|---|
| C12N 15/67 | (2006.01) |
| C07K 14/405 | (2006.01) |
| C12N 9/22 | (2006.01) |
| C12N 9/96 | (2006.01) |
| C12N 15/113 | (2010.01) |
| C12N 15/70 | (2006.01) |
| C12P 19/34 | (2006.01) |

(52) U.S. Cl.
CPC .............. *C12N 15/67* (2013.01); *C12N 9/22* (2013.01); *C12N 9/96* (2013.01); *C12N 15/113* (2013.01); *C12N 15/70* (2013.01); *C12P 19/34* (2013.01); *C07K 14/405* (2013.01); *C12N 2310/20* (2017.05); *C12N 2310/3125* (2013.01); *C12N 2800/80* (2013.01)

(58) Field of Classification Search
CPC ............ C12N 15/67; C12N 9/22; C12N 9/96; C12N 15/113; C12N 15/70; C12N 2310/20; C12N 2310/3125; C12N 2800/80; C12N 15/76; C12P 19/34; C12P 21/02; C07K 14/405
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,683,195 A | 7/1987 | Mullis et al. |
| 4,683,202 A | 7/1987 | Mullis |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,965,188 A | 10/1990 | Mullis et al. |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |

(Continued)

FOREIGN PATENT DOCUMENTS

| | | |
|---|---|---|
| EP | 0614907 A1 | 9/1994 |
| EP | 0629633 A2 | 12/1994 |

(Continued)

OTHER PUBLICATIONS

Malyshev, Denis A., et al. "A semi-synthetic organism with an expanded genetic alphabet." Nature 509.7500 (2014): 385-388 (Year: 2014).*
Chakraborty, Syandan, et al. "Vector modifications to eliminate transposase expression following piggyBac-mediated transgenesis." Scientific reports 4.1 (2014): 7403 (Year: 2014).*
Zhang, Yorke, et al. "A semisynthetic organism engineered for the stable expansion of the genetic alphabet." Proceedings of the National Academy of Sciences 114.6 (Jan. 23, 2017): 1317-1322 (Year: 2017).*
Van Rooijen, Rutger J., Mike J. Gasson, and Willem M. De Vos. "Characterization of the Lactococcus lactis lactose operon promoter: contribution of flanking sequences and LacR repressor to promoter activity." Journal of bacteriology 174.7 (1992): 2273-2280 (Year: 1992).*

(Continued)

*Primary Examiner* — Nancy J Leith
*Assistant Examiner* — Kyle T Rega
(74) *Attorney, Agent, or Firm* — Thomas Fitting

(57) ABSTRACT

Disclosed herein are methods, cells, engineered microorganisms, and kits for increasing the production of polypeptides comprising one or more unnatural amino acids. Further provided are cells, engineered microorganisms, and kits for increasing the retention of unnatural nucleic acids encoding the unnatural amino acids in an engineered cell, or semi-synthetic organism.

14 Claims, 17 Drawing Sheets

Specification includes a Sequence Listing.

(56) References Cited

U.S. PATENT DOCUMENTS

| | | |
|---|---|---|
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,656,493 A | 8/1997 | Mullis et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 5,888,732 A | 3/1999 | Hartley et al. |
| 6,005,096 A | 12/1999 | Matteucci et al. |
| 6,143,557 A | 11/2000 | Hartley et al. |
| 6,171,861 B1 | 1/2001 | Hartley et al. |
| 6,268,490 B1 | 7/2001 | Imanishi et al. |
| 6,270,969 B1 | 8/2001 | Hartley et al. |
| 6,277,608 B1 | 8/2001 | Hartley et al. |
| 6,525,191 B1 | 2/2003 | Ramasamy |
| 6,670,461 B1 | 12/2003 | Wengel et al. |
| 6,720,140 B1 | 4/2004 | Hartley et al. |
| 6,770,748 B2 | 8/2004 | Imanishi et al. |
| 6,794,499 B2 | 9/2004 | Wengel et al. |
| 6,955,807 B1 | 10/2005 | Shanafelt et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 9,682,934 B2 | 6/2017 | Stafford et al. |
| 9,840,493 B2 | 12/2017 | Yang et al. |
| 9,938,516 B2 | 4/2018 | Zimmerman et al. |
| 9,988,619 B2 | 6/2018 | Zimmerman et al. |
| 10,513,706 B2 | 12/2019 | Romesberg et al. |
| 10,626,138 B2 | 4/2020 | Romesberg et al. |
| 10,696,719 B2 | 6/2020 | Romesberg et al. |
| 10,696,720 B2 | 6/2020 | Romesberg et al. |
| 2002/0007051 A1 | 1/2002 | Cheo et al. |
| 2004/0171570 A1 | 9/2004 | Allerson et al. |
| 2005/0130923 A1 | 6/2005 | Bhat et al. |
| 2006/0074035 A1 | 4/2006 | Hong et al. |
| 2007/0004041 A1* | 1/2007 | Church ............... C12N 15/90 435/473 |
| 2007/0054381 A1 | 3/2007 | Zelder et al. |
| 2007/0287831 A1 | 12/2007 | Seth et al. |
| 2008/0039618 A1 | 2/2008 | Allerson et al. |
| 2008/0300163 A1 | 12/2008 | Cho et al. |

(56) References Cited

U.S. PATENT DOCUMENTS

| | | |
|---|---|---|
| 2012/0077252 A1 | 3/2012 | Picataggio et al. |
| 2012/0244112 A1 | 9/2012 | Ast et al. |
| 2014/0328791 A1 | 11/2014 | Bossard et al. |
| 2017/0369871 A1 | 12/2017 | Ptacin et al. |
| 2018/0086734 A1 | 3/2018 | Yang et al. |
| 2019/0218257 A1 | 7/2019 | Romesberg et al. |
| 2019/0376054 A1 | 12/2019 | Ptacin et al. |
| 2020/0017540 A1 | 1/2020 | Romesberg et al. |
| 2020/0024597 A1 | 1/2020 | Ptacin et al. |
| 2020/0040027 A1 | 2/2020 | Romesberg et al. |
| 2020/0095591 A1 | 3/2020 | Romesberg et al. |
| 2020/0131555 A1 | 4/2020 | Ptacin et al. |
| 2020/0224234 A1 | 7/2020 | Romesberg et al. |
| 2020/0277342 A1 | 9/2020 | Romesberg et al. |
| 2020/0377877 A1 | 12/2020 | Romesberg et al. |
| 2020/0392550 A1 | 12/2020 | Romesberg et al. |
| 2021/0222147 A1 | 7/2021 | Ptacin et al. |
| 2022/0228148 A1 | 7/2022 | Romesberg et al. |
| 2022/0243244 A1 | 8/2022 | Romesberg et al. |

FOREIGN PATENT DOCUMENTS

| | | |
|---|---|---|
| WO | WO-9213869 A1 | 8/1992 |
| WO | WO-9422890 A1 | 10/1994 |
| WO | WO-9735869 A1 | 10/1997 |
| WO | WO-9914226 A2 | 3/1999 |
| WO | WO-9962923 A2 | 12/1999 |
| WO | WO-0105801 A1 | 1/2001 |
| WO | WO-0132887 A1 | 5/2001 |
| WO | WO-02070533 A2 | 9/2002 |
| WO | WO-2004007713 A1 | 1/2004 |
| WO | WO-2004106356 A1 | 12/2004 |
| WO | WO-2005021570 A1 | 3/2005 |
| WO | WO-2005026187 A1 | 3/2005 |
| WO | WO-2005045015 A2 | 5/2005 |
| WO | WO-2006049297 A1 | 5/2006 |
| WO | WO-2007015557 A1 | 2/2007 |
| WO | WO-2007066737 A1 | 6/2007 |
| WO | WO-2007090071 A2 | 8/2007 |
| WO | WO-2007134181 A2 | 11/2007 |
| WO | WO-2008101157 A1 | 8/2008 |
| WO | WO-2008150729 A2 | 12/2008 |
| WO | WO-2008154401 A2 | 12/2008 |
| WO | WO-2009006478 A2 | 1/2009 |
| WO | WO-2009123216 A1 | 10/2009 |
| WO | WO-2011043385 A1 | 4/2011 |
| WO | WO-2011139699 A2 | 11/2011 |
| WO | WO-2013176772 A1 | 11/2013 |
| WO | WO-2014160025 A2 | 10/2014 |
| WO | WO-2015021432 A1 | 2/2015 |
| WO | WO-2015086795 A1 | 6/2015 |
| WO | WO-2015157555 A2 | 10/2015 |
| WO | WO-2016073433 A1 | 5/2016 |
| WO | WO-2016094867 A1 | 6/2016 |
| WO | WO-2016115168 A1 | 7/2016 |
| WO | WO-2017106767 A1 | 6/2017 |
| WO | WO-2017223528 A1 | 12/2017 |
| WO | WO-2019014262 A1 | 1/2019 |
| WO | WO-2019014267 A1 | 1/2019 |
| WO | WO-2019133883 A1 | 7/2019 |
| WO | WO-2021067313 A1 | 4/2021 |
| WO | WO-2022087475 A1 | 4/2022 |

OTHER PUBLICATIONS

Nuñez, James K., Lucas B. Harrington, and Jennifer A. Doudna. "Chemical and biophysical modulation of Cas9 for tunable genome engineering." ACS chemical biology 11.3 (Feb. 9, 2016): 681-688 (Year: 2016).*

Machida, Yasunori, et al. "Factors determining frequency of plasmid cointegration mediated by insertion sequence IS 1." Proceedings of the National Academy of Sciences 79.2 (1982): 277-281 (Year: 1982).*

Trentmann, Oliver, et al. "Nonmitochondrial ATP/ADP transporters accept phosphate as third substrate." Journal of Biological Chemistry 283.52 (2008): 36486-36493 (Year: 2008).*

Curti (Molecular microbiology 71.2 (2009): 315-331) (Year: 2009).*

Ennis (Proceedings of the National Academy of Sciences 82.10 (1985): 3325-3329) (Year: 1985).*

Acsadi et al. Human Dystrophin Expression in mdx Mice After Intramuscular Injection of DNA Constructs. Nature 352:815-818 (1991).

Adhikary et al. Adaptive Mutations Alter Antibody Structure and Dynamics During Affinity Maturation. Biochemistry 54(11):2085-93 (2015).

Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).

Ambrogelly et al. Pyrrolysine is not hardwired for cotranslational insertion at UAG condons. PNAS 104(9):3141-3146 (2007).

Amiri et al. Deep origin of plastid/parasite ATP/ADP translocases. J. Mol. Evol. 56:137-150 (2003).

Arenas-Ramirez et al. Improved cancer immunotherapy by a CD25-mimobody conferring selectivity to human interleukin-2. Sci Transl Med 8:367ra166 (Nov. 30, 2016). 13 pages.

Arie et al. Phylogenetic identification of n-alkane assimilating Candida yeasts based on nucleotide divergence in the 59 end of LSU rDNA gene. J Gen Appl Microbiol. 46(5):257-262 (2000).

Ast et al. Diatom plastids depend on nucleotide import from the cytosol. PNAS USA 106:3621-3626 (2009).

Baba et al. Construction of Escherichia coli K-12 in-frame, single-gene knockout mutants: the Keio collection. Mol Syst Biol. 2:2006. 0008 (2006).

Banach-Orlowska et al. DNA polymerase II as a fidelity factor in chromosomal DNA synthesis in Escherichia coli. Mol. Microbiol. 58:61-70 (2005).

Beigelman et al. Synthesis of 5'-C-Methyl-D-allo- & L-Talo-ribonucleoside 3' -O-Phosphoramidites & Their Incorporation into Hammerhead Ribozymes. Nucleosides and Nucleotides 14(3-5): 901-905 (1995).

Bell et al. RecA: Regulation and Mechanism of a Molecular Search Engine. Trends Biochem. Sci. 41:491-507 (2016).

Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).

Berardini et al. DNA polymerase II (poIB) is involved in a new DNA repair pathway for DNA interstrand cross-links in Escherichia coli. J Bacteria 181:2878-2882 (1999).

Berger et al. Stability and selectivity of unnatural DNA with five-membered-ring nucleobase analogues. J Am Chem Soc 124(7):1222-6 (2002).

Berger et al. Stable and selective hybridization of oligonucleotides with unnatural hydrophobic bases. Angew Chem Int Ed Engl 39:2940-2942 (2000).

Berger et al. Universal bases for hybridization, replication and chain termination. Nucleic Acids Res 28(15):2911-2914 (2000).

Betz et al. KlenTaq polymerase replicates unnatural base pairs by inducing a Watson-Crick geometry. Nat Chem Biol 8:612-614 (2012).

Betz et al. Structural insights into DNA replication without hydrogen bonds. J Am Chem Soc 135:18637-18643 (2013).

Bhatt et al. Peripheral Blood Lymphocyte Responses in Patients with Renal Cell Carcinoma treated with High-Dose Interleukin-2. Poster (SITC 2018).

Biocentury Innovations publication Oct. 27, 2016 (26 pgs).

Bohringer et al. Synthesis of 5'-deoxy-5'-methylphosphonate linked thymidine oligonucleotides. Tet Lett 34:2723-2726 (1993).

Bonner et al. DNA polymerase II is encoded by the DNA damage-inducible dinA gene of Escherichia coli. PNAS USA 87:7663-7667 (1990).

Bordo et al. Suggestions for "safe" residue substitutions in site-directed mutagenesis. J Mol Biol 217:721-729 (1991).

Boyman et al. Selective Stimulation of T Cell subsets with Antibody-Cytokine Immune Complexes. Science 311:1924-1927 (2006).

(56) References Cited

OTHER PUBLICATIONS

Boyman et al. Selectively Expanding Subsets of T Cells in Mice by Injection of Interleukin-2/Antibody Complexes: Implications for Transplantation Tolerance. Transplantation Proceedings 44:1032-1034 (2012).

Boyman et al. The role of interleukin-2 during homeostatis and activation of the immune system. Nature 12:180-190 (2012).

Braasch et al. Locked nucleic acid (LNA): fine-tuning the recognition of DNA and RNA. Chem Bio 8:1-7 (2001).

Branca. Rekindling cancer vaccines. Nat Biotechnol 34(10):1019-1025 (2016).

Cameron et al. Tunable protein degradation in bacteria. Nature Biotechnology 32:1276-1281 (2014).

Cann et al. A heterodimeric DNA polymerase: Evidence that members of Euryarchaeota possess a distinct DNA polymerase. PNAS USA 95:14250 (1998).

Cantrell. Vectors for the expression of recombinant proteins in *E. coli*. Methods Mol Biol. 235:257-75 (2003).

Cariello et al. Fidelity of Thermococcus litoralis DNA polymerase (VentTM) in PCR determined by denaturing gradient gel electrophoresis Nucl Acid Res 19:4193-4198 (1991).

Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).

Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).

Chastgner et al. Lack of intermediate-affinity interleukin-2 receptor in mice leads to dependence on interkeukin-2 receptor α,β and γ chain expression for T cell growth. Eur J Immunol 26:201-206 (1996).

Chatterjee et al. A Versatile Platform for Single- and Multiple-Unnatural Amino Acid Mutagenesis in *Escherichia coli*. Biochemistry 52(10):1828-1837 (2013).

Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).

Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).

Chen et al. A novel human IL-2 mutein with minimal systemic toxicity exerts greater antitumor efficacy than wild-type IL-2. Cell Death& Disease 9:989 (2018).

Chen et al. Directed polymerase evolution. FEBS Lett. 588(2):219-229 (2014).

Chen et al. Phosphonate Analogues of Cytosine Arabinoside Monophosphate. Phosphorus, Sulfur and Silicon 177:1783-1786 (2002).

Chen et al. The expanding world of DNA and RNA. Curr Opin Chem Biol 34:80-87 (2016).

Chien et al. Deoxyribonucleic acid polymerase from the extreme thermophile Thermus aquaticus. J Bacteriol 127:1550-1557 (1976).

Collingwood et al. The Synthesis and Incorporation in Oligonucleotides of a Thymidine Dimer Containing an Internucleoside Phosphinate Linkage. Synlett 7:703-705 (1995).

Crooke et al. Pharmacokinetic properties of several novel oligonucleotide analogs in mice. J Pharmacol Exp Ther 277:923-937 (1996).

Database UniParc [Online] May 31, 2010 (May 31, 2010), Database accession No. UPI0001D42ADE (2 pgs).

Datsenko et al. One-step inactivation of chromosomal genes in *Escherichia coli* K-12 using PCR products. PNAS USA 97(12):6640-6645 (2000).

De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).

Derbyshire et al. Genetic and crystallographic studies of the 3',5'-exonucleolytic site of DNA polymerase I. Science 240:199-201 (1988).

Deuschle et al. Promoters of *Escherichia coli*: a hierarchy of in vivo strength indicates alternate structures. EMBO J 5:2987-2994 (1986).

Dhami et al. Systematic exploration of a class of hydrophobic unnatural base pairs yields multiple new candidates for the expansion of the genetic alphabet. Nucleic Acids Res 42:10235-10244 (2014).

Diab et al. NKTR-214 (CD-122-biased agonist) plus nivolumab in patients with advanced solid tumors: Preliminary phase 1/2 results of Pivot. Powerpoint presentation. ClinicalTrials.gov NCT02983045. 2018 ASCO Annual Meeting (2018).

Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).

Diaz et al. Accuracy of replication in the polymerase chain reaction. Comparison between Thermotoga maritima DNA polymerase and Thermus aquaticus DNA polymerase. Braz J Med Res 31:1239-1242 (1998).

Dien et al. Eight-Letter DNA. Biochemistry 58:2581-2583 (2019).

Dien et al. Expansion of the genetic code via expansion of the genetic alphabet. Curr Opin Chem Biol 46:196-202 (2018).

Dien et al. Progress Toward a Semi-Synthetic Organism with an Unrestricted Expanded Genetic Alphabet. J Am Chem Soc. 140:16115-16123 (2018).

Doudna et al. Genome editing. The new frontier of genome engineering with CRISPR-Cas9. Science 346:1258096 (2014).

Dranoff. Cytokines in cancer pathogenesis and cancer therapy. Nature Reviews Cancer 4:11-22 (2004).

Dumas et al. Designing logical codon reassignment—Expanding the chemistry in biology. Chem Sci 6:50-69 (2015).

Dupradeau et al. Differential solvation and tautomer stability of a model base pair within the minor and major grooves of DNA. J Am Chem Soc 127(44):15612-7 (2005).

Egholm et al. PNA hybridizes to complementary oligonucleotides obeying the Watson-Crick hydrogen-bonding rules. Nature 365(6446):566-568 (1993).

Elayadi et al. Application of PNA and LNA oligomers to chemotherapy. Curr Opinion Invens Drugs 2:558-561 (2001).

Ellington et al. In vitro selection of RNA molecules that bind specific ligands. Nature 346:818-822 (1990).

Engler et al. A one pot, one step, precision cloning method with high throughput capability. PLoS One 3:e3647 (2008).

Englisch et al. Chemically Modified Oligonucleotides as Probes and Inhibitors. Angew. Chem. Int. Ed. Eng. 30:613-629 (1991).

Eppacher et al. Synthesis and Incorporation of C(5')-Ethynylated Uracil-Derived Phosphoramidites into RNA. Helvetica Chimica Acta 87:3004-3020 (2004).

Escoubas et al. Is the IS1 transposase, InsAB', the only IS1-encoded protein required for efficient transposition? J Bacteriol. 176:5864-5867 (1994).

Fa et al. Expanding the substrate repertoire of a DNA polymerase by directed evolution. J Am Chem Soc 126(6):1748-54 (2004).

Fairhurst et al. Synthesis and Hybridisation Properties of Phosphonamidate Ester Modified Nucleic Acid. Synlett 4:467-472 (2001).

Fan et al. Rationally evolving tRNAPyl for efficient incorporation of noncanonical amino acids. Nucleic Acids Res 43(22):e156 (2015).

Feldman et al. A Tool for the Import of Natural and Unnatural Nucleoside Triphosphates into Bacteria. J Am Chem Soc 140(4):1447-1454 (2018).

Feldman et al. Chemical Stabilization of Unnatural Nucleotide Triphosphates for the in Vivo Expansion of the Genetic Alphabet. J Am Chem Soc 139(6):2464-2467 (2017).

Feldman et al. In Vivo Structure-Activity Relationships and Optimization of an Unnatural Base Pair for Replication in a Semi-Synthetic Organism. J Am Chem Soc 139:11427-11433 (2017).

(56) References Cited

OTHER PUBLICATIONS

Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Floros et al. Anticancer Cytokines: Biology and Clinical Effects of Interferon-α2, Interleukin (IL)-2, IL-15, IL-21, and IL-12. Semin Oncol 42(4):539-548 (2015).
Fluman et al. mRNA-programmed translation pauses in the targeting of E. coli membrane proteins. eLife 2014; 3:e03440.
Fu et al. Improving CRISPR-Cas nuclease specificity using truncated guide RNAs. Nat Biotechnol 32:279-284 (2014).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gibson, et al. Enzymatic assembly of DNA molecules up to several hundred kilobases. Nat Methods. May 2009;6(5):343-5.
Gietz et al. Improved method for high efficiency transformation of intact yeast cells. Nucleic Acids Res 20:1425 (1992).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Goodman et al. Causes and effects of N-terminal codon bias in bacterial genes. Science 342:475-479 (2013).
Guo et al. Directed evolution of an enhanced and highly efficient FokI cleavage domain for zinc finger nucleases. J Mot Biol 400:96-107 (2010).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).

Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Horvath et al. CRISPR/Cas, the Immune System of Bacteria and Archaea. Science 327:167-170 (2010).
Hsu et al. Development and applications of CRISPR-Cas9 for genome engineering. Cell 157(6):1262-78 (2014).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Insight-Esprit Study Group et al. Interleukin-2 Therapy in Patients with HIV Infection. N Engl J Med. 361(16):1548-59 (2009).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Jiricny. Postreplicative mismatch repair. Cold Spring Harb. Perspect. Biol. 5:a012633 (2013).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).

(56) References Cited

OTHER PUBLICATIONS

Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Khlebnikov et al. Effect of lacY expression on homogeneity of induction from the P(tac) and P(trc) promoters by natural and synthetic inducers. Biotechnol Prog 18:672-674 (2002).
Kim et al. Stability and polymerase recognition of pyridine nucleobase analogues: role of minor-groove H-bond acceptors. Angew Chem Int Ed Engl 45(46):7809-12 (2006).
Kimoto et al. Chemical Biology of Nucleic Acids: Fundamentals and Clinical Applications (eds A. Volker Erdmann, T. Wojciech Markiewicz, & Jan Barciszewski) pp. 131-148 (Springer Berlin Heidelberg, 2014).
Kisker et al. Prokaryotic nucleotide excision repair. Cold Spring Harb. Perspect. Biol. 5:a012591 (2013).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Kornberg et al. Purification and DNA synthesis in cell-free extracts: properties of DNA polymerase II. PNAS USA 68:761-764 (1971).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Krieg et al. Improved IL-2 immunotherapy by selective stimulation of IL-2 receptors on lymphocytes and endothelial cells. PNAS USA 107(26):11906-11911 (Jun. 29, 2010).
Kuhlman et al. Site-specific chromosomal integration of large synthetic constructs. Nucleic Acids Res 38:e92 (2010).
Kumar et al. The First Analogues of LNA (Locked Nucleic Acids): Phosphorothioate LNA and 2'-Thio-LNA. Bioorg Med Chem Lett 8:2219-2222 (1998).
Kuzminov. Recombinational repair of DNA damage in *Escherichia coli* and bacteriophage lambda. Mol Biol. Rev. 63:751-813 (1999).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lazear et al. Targeting of IL-2 to cytotoxic lymphocytes as an improved method of cytokine-driven immunotherapy. Oncoimmunology 6(2):e1265721 (2017).
Lecomte et al. Selective Inactivation of the 3' to 5' exonuclease activity of *Escherichia coli* DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Lifsics et al. DNA replication defect in *Salmonella typhimurium* mutants lacking the editing (epsilon) subunit of DNA polymerase III. Bacteria 174:6965-6973 (1992).
Liu et al. Adding new chemistries to the genetic code. Annu Rev Biochem 79:413-444 (2010).

(56) References Cited

OTHER PUBLICATIONS

Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Marraffini et al. CRISPR interference: RNA-directed adaptive immunity in bacteria and archaea. Nat Rev Genet. 11(3):181-90 (2010).
Marshall et al., A link between integral membrane protein expression and simulated integration efficiency. Cell Reports 16(8): 2169-2177 (2016).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Michel. After 30 years of study, the bacterial SOS response still surprises US. PLoS Biol. 3:e255 (2005).
Micklefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue): D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mutalik, et al., Precise and reliable gene expression via standard transcription and translation initiation elements. Nature Methods 10:354-360 (2013).
Myers et al. Reverse transcription and DNA amplification by a Thermus thermophilus DNA polymerase. Biochemistry 30:7661-7666 (1991).
Nawrot et al. A novel class of DNA analogs bearing 5'-C-phosphonothymidine units: synthesis and physicochemical and biochemical properties. Oligonucleotides16(1):68-82 (2006).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.

(56) References Cited

OTHER PUBLICATIONS

Nektar Therapeutics. Investor Meeting presentation Jun. 3, 2017.
Nelson et al. N3'—>P5' Oligodeoxyribonucleotide Phosphoramidates: A New Method of Synthesis Based on a Phosphoramidite Amine-Exchange Reaction. J Org Chem 62:7278-7287 (1997).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nicolini et al. The FAP-IL2v Immunocytokine is a Versatile Combination Partner for Cancer Immunotherapy. Poster (SITC 2018).
Nielsen et al. Sequence-selective recognition of DNA by strand displacement with a thymine-substituted polyamide. Science 254:1497-1500 (1991).
Nomura et al. Transcriptional organization of the convergent overlapping dnaQ-rnh genes of *Escherichia coli*. J. Biol. Chem. 260:7122-7125 (1985).
Nordstrom et al. Characterization of bacteriophage T7 Dna polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2017/039133 International Search Report and Written Opinion dated Sep. 20, 2017.
PCT/US2018/041503 International Search Report and Written Opinion dated Nov. 7, 2018.
PCT/US2018/045257 International Search Report and Written Opinion dated Nov. 21, 2018.
PCT/US2018/067969 International Search Report and Written Opinion dated Mar. 18, 2019.
Peyrottes et al. Oligodeoxynucleoside phosphoramidates (P-NH2): synthesis and thermal stability of duplexes with DNA and RNA targets. Nucleic Acids Res 24:1841-1848 (1996).

Pfannenstiel et al. A Novel, Individualized Xenograft Model of Cancer Immunotherapy and Tumor Growth Inhibition by ALKS 4230. Poster #P351 (SITC 2017).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Quan et al. Circular polymerase extension cloning for high-throughput cloning of complex and combinatorial DNA libraries. Nat Protoc 6(2):242-251 (2011).
Rangarajan et al. A phenotype for enigmatic DNA polymerase II: a pivotal role for pol II in replication restart in UV-irradiated *Escherichia coli*. PNAS USA 96:9224-9229 (1999).
Rath et al. The CRISPR-Cas immune system: biology, mechanisms and applications. Biochimie 117:119-128 (2015).
Roessler et al. Cooperative interactions between the interleukin 2 receptor α and β chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1:Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sabri et al. Knock-in/Knock-out (KIKO) vectors for rapid integration of large DNA sequences, including whole metabolic pathways, onto the *Escherichia coli* chromosome at well-characterised loci. Microb Cell Fact 12:60 (2013).
Saha et al. 5'-Methyl-DNA-A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schlegel et al. De-convoluting the genetic adaptations of *E. coli* C41(DE3) in real time reveals how alleviating protein production stress improves yields. Cell Rep 10:1758-1766 (2015).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Schneider et al. NIH Image to ImageJ: 25 years of image analysis. Nat Methods 9:671-675 (2012).
Schultz et al. Oligo-2'-fluoro-2'-deoxynucleotide N3'—> P5' phosphoramidates: synthesis and properties. Nucleic Acids Res 24:2966-2973 (1996).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Shaloiko et al. Effective non-viral leader for cap-independent translation in a eukaryotic cell-free system. Biotechnology and Bioengineering 88(6):730-739 (2004).
Sharma et al. NKTR-214 enhances anti-tumor T cell immune responses induced by checkpoint blockade or vaccination. Poster (SITC 2017).

(56) References Cited

OTHER PUBLICATIONS

Shea et al. Synthesis, hybridization properties and antiviral activity of lipid-oligodeoxynucleotide conjugates. Nucl. Acids Res 18:3777-3783 (1990).
Siegel et al. Interleukin-2 Toxicity. J Clin Oncol 9(4):694-704 (1991).
Sikorski et al. A system of shuttle vectors and yeast host strains designed for efficient manipulation of DNA in *Saccharomyces cerevisiae*. Genetics 122:19-27 (1989).
Sim et al. IL2 Variant Circumvents ICOS+ Regulatory T-cell Expansion and Promotes NK Cell Activation. Cancer Immunol Res. 4(11):983-995 (Nov. 2016).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Sivakumar et al. Comparison of Vascular Leak Syndrome in Mice treated with IL21 or IL2. Comparative Medicine 63(1):13-21 (2013).
Southern et al. Transformation of mammalian cells to antibiotic resistance with a bacterial gene under control of the SV40 early region promoter. J Mol Appl Genet 1:327-341 (1982).
Spangler et al. Antibodies to Interleukin-2 Elicit Selective T Cell Subset Potentiation through Distinct Conformational Mechanism. Immunity 42:815-825 (2015).
Srivastava et al. Five- and six-membered conformationally locked 2',4'-carbocyclic ribo-thymidines: synthesis, structure, and biochemical studies. J Am Chem Soc 129(26):8362-8379 (2007).
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sugden et al. A vector that replicates as a plasmid and can be efficiently selected in B-lymphoblasts transformed by Epstein-Barr virus. Mol. Cell. Biol. 5:410-413 (1985).
Sun et al. First-in-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al. Inhibition of HIV proliferation in MT-4 cells by antisense oligonucleotide conjugated to lipophilic groups. Biochimie 75:49-54 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under the Securities Act of 1933 filed Nov. 27, 2018 (355 pgs.).
Tae et al. Efforts toward expansion of the genetic alphabet: replication of DNA with three base pairs. J. Am. Chem. Soc. 123:7439-7440 (2001).
Taft-Benz et al. Mutational analysis of the 3'→ 5' proofreading exonuclease of *Escherichia coli* DNA polymerase III. Nucleic Acids Res. 26:4005-4011 (1998).
Takagi et al. Characterization of DNA polymerase from *Pyrococcus* sp. strain KOD1 and its application to PCR. Appl Environ Microbiol 63(11):4504-4510 (1997).
Takeshita et al. High-copy-number and low-copy-number plasmid vectors for lacZ alpha-complementation and chloramphenicol- or kanamycin-resistance selection. Gene 61, 63-74 (1987).
Tang et al. Roles of *E. coli* DNA polymerases IV and V in lesion-targeted and untargeted SOS mutagenesis. Nature 404:1014-1018 (2000).
Tapp et al. Homogeneous scoring of single-nucleotide polymorphisms: comparison of the 5'-nuclease TaqMan assay and Molecular Beacon probes. Biotechniques 28(4):732-738 (2000).
The Concise Encyclopedia of Polymer Science and Engineering, Kroschwitz, J.I., Ed., John Wiley & Sons pp. 858-859 (1990).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,097 Office Action dated Feb. 7, 2020.
U.S. Appl. No. 16/546,097 Office Action dated Nov. 21, 2019.
U.S. Appl. No. 16/546,100, filed Aug. 20, 2019.
U.S. Appl. No. 16/546,100 Office Action dated Feb. 7, 2020.
U.S. Appl. No. 16/546,100 Office Action dated Nov. 27, 2019.
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
U.S. Appl. No. 16/900,154, filed Jun. 12, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody—Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fc-mediated depletion of regulatory T-cells. Nat Comm 8:15373 (2017).
Verma. Retroviral vectors for gene transfer. In: Microbiology (Leive L et al., eds., Ann. Soc. Microbiol) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino) methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).

(56) References Cited

OTHER PUBLICATIONS

Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wan et al. Pyrrolysyl- tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. Response and adaptation of *Escherichia coli* to suppression of the amber stop codon. Chembiochem 15:1744-1749 (2014).
Wang et al. An engineered rare codon device for optimization of metabolic pathways. Scientific Reports 6:20608 (2016).
Wang et al. Biophysical and biochemical properties of oligodeoxynucleotides containing 4'-C- and 5'-C-substituted thymidines. Bioorg Med Chem Lett 9:885-890 (1999).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, β, and γc Receptors. Science 310:1159-63 (2005).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Ying et al. "Molecular Variation and Horizontal Gene Transfer of the Homocysteine Methyltransferase Gene mmuM and its Distribution in Clinical Pathogens," International Journal of Biological Sciences, Jan. 1, 2015 (Jan. 1, 2015), vol. 11, Iss. 1, pp. 11-21.
Yu et al. Polymerase recognition of unnatural base pairs. Angew Chem Int Ed Engl 41(20):3841-4 (2002).
Zalevsky. Jefferies 2016 Global Healthcare Conference. PowerPoint presentation (Nov. 16, 2016).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Evolution of functional six-nucleotide DNA. J Am Chem Soc 137:6734--6737 (2015).
Zhang et al. Semisynthetic Organisms with Expanded Genetic Codes. Biochemistry 57:2177-2178 (20180.
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).

\* cited by examiner

| Strain | Chromosomal UBP | dNaMTP-dTPT3TP | Doubling Time Mean (minutes) | S.D. |
|---|---|---|---|---|
| lacZYA::cat | - | + | 27.802 | 0.243 |
|  | - | - | 33.381 | 0.463 |
| WT-Opt | - | + | 34.474 | 2.570 |
|  | - | - | 35.929 | 0.264 |
|  | + | + | 39.443 | 0.795 |
|  | + | - | 41.530 | 2.545 |
| ΔrecA-Opt | - | + | 50.540 | 0.820 |
|  | - | - | 58.608 | 4.314 |
|  | + | + | 42.892 | 1.371 |
|  | + | - | 83.312 | 6.996 |
| Pol II+ΔrecA-Opt | - | + | 51.556 | 1.907 |
|  | - | - | 58.060 | 3.030 |
|  | + | + | 42.061 | 1.255 |
|  | + | - | 67.114 | 5.052 |

UNNATURAL BASE PAIR COMPOSITIONS AND METHODS OF USE

CROSS-REFERENCE

This application is a continuation of International Application No. PCT/US2018/067969, filed Dec. 28, 2018, which claims the benefit of U.S. Provisional Application No. 62/612,062, filed on Dec. 29, 2017, both of which are herein incorporated by reference in their entireties.

STATEMENT OF GOVERNMENT LICENSE RIGHTS

This invention was made with government support under grant number GM118178 awarded by The National Institutes of Health and grant number DGE1346837 awarded by The National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 25, 2020, is named 36271807301_SL.txt and is 116,359 bytes in size.

BACKGROUND OF THE INVENTION

Applications of the ability to sequence-specifically synthesize/amplify oligonucleotides (DNA or RNA) with polymerases are restricted by the limited chemical/physical diversity present in the natural genetic alphabet (the four natural nucleotides A, C, G, and T in DNA, and the four natural nucleotides A, C, G, and U in RNA). An expanded genetic alphabet including unnatural nucleic acids increases the information that can be stored in a cell and facilitate the creating of semi-synthetic organisms (SSOs) that use this increased information to create novel forms of gene expression products.

SUMMARY OF THE INVENTION

Described herein, in certain embodiments, are methods, cells, engineered microorganisms, plasmids, and kits for increased production of a nucleic acid molecule that comprises an unnatural nucleotide. In some embodiments, also described herein include cells, engineered microorganisms, plasmids, and methods of use that utilizes a modified transposition-associated protein, a modified DNA repair protein, or a combination thereof for increased production of a nucleic acid molecule that comprises an unnatural nucleotide.

Aspects disclosed herein provide engineered host cells comprising: a first nucleic acid molecule comprising an unnatural nucleotide; and optionally, a second nucleic acid molecule encoding a modified transposition-associated protein or transposable element. In some embodiments, the engineered host cell further comprises a third nucleic acid molecule encoding a modified nucleoside triphosphate transporter, wherein the third nucleic acid molecule is incorporated in a genomic sequence of the engineer host cell, or comprises a plasmid encoding the modified nucleoside triphosphate transporter. In some embodiments, the modified nucleoside triphosphate transporter exhibits increased stability of expression in the engineered host cell as compared to an expression in an equivalent engineered host cell that does not comprise the second nucleic acid molecule encoding the modified transposition-associated protein. In some embodiments, the modified nucleoside triphosphate transporter comprises a deletion of an entire nucleic acid molecule encoding the nucleoside triphosphate transporter, an N-terminal truncation, a C-terminal truncation, or a truncation of both termini. In some embodiments, the modified nucleoside triphosphate transporter comprises a nucleoside triphosphate transporter from *Phaeodactylum tricornutum* ($PtNTT_2$). In some embodiments, the modified nucleoside triphosphate transporter comprises a deletion. In some embodiments, the deletion is a terminal deletion or an internal deletion. In some embodiments, the deletion is an N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the $PtNTT_2$ is under the control of a promoter selected from a pSC plasmid or a promoter from a lac operon. In some embodiments, the engineered host cell further comprises a Cas9 polypeptide or variants thereof; and a single guide RNA (sgRNA) comprising a crRNA-tracrRNA scaffold, wherein the combination of Cas9 polypeptide or variants thereof and sgRNA modulates replication of the first nucleic acid molecule encoding the unnatural nucleotide. In some embodiments, the sgRNA comprises a target motif that recognizes a modification at the unnatural nucleotide position within the nucleic acid molecule. In some embodiments, the sgRNA further comprises a protospacer adjacent motif (PAM) recognition element. In some embodiments, the PAM element is adjacent to the 3' terminus of the target motif. In some embodiments, the target motif is between 15 to 30 nucleotides in length. In some embodiments, the combination of Cas9 polypeptide or variants thereof and sgRNA decreases the replication rate of the nucleic acid molecule comprising the modification by about 80%, 85%, 95%, 99%, or higher. In some embodiments, the Cas9 polypeptide is a wild-type Cas9. In some embodiments, the second nucleic acid molecule comprises a gene comprising catalase (cat), IS1 protein insB-4 (insB-4), IS1 protein insA-4 (insA-4), or a combination thereof. In some embodiments, the modified transposition-associated protein comprises Insertion element IS1 4 protein InsB, Insertion element IS1 4 protein InsA, or a combination thereof; and wherein the modified transposable element comprises IS1. In some embodiments, the gene comprises one or more deletions, wherein the one or more deletions comprise an N-terminal deletion, a C-terminal deletion, a truncation at both termini, an internal deletion, and/or a deletion of the entire gene. In some embodiments, the engineered host cell further comprises a fifth nucleic acid molecule encoding a modified DNA repair response-associated protein, wherein the DNA repair response comprises recombinational repair, SOS response, nucleotide excision repair, or methyl-directed mismatch repair, or a combination thereof. In some embodiments, the modified DNA repair response-associated protein comprises RecA, Rad51, RadA, or LexA, or a combination thereof. In some embodiments, the engineered host cell is a prokaryotic cell comprising an *Escherichia coli* cell, *Escherichia coli* BL21 (DE3) cell. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-aminopropyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of:

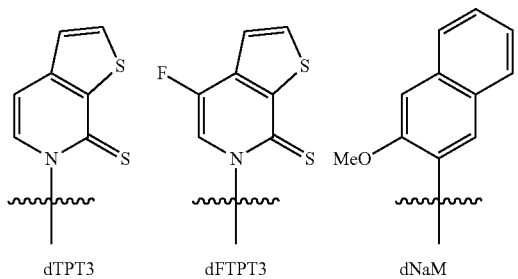

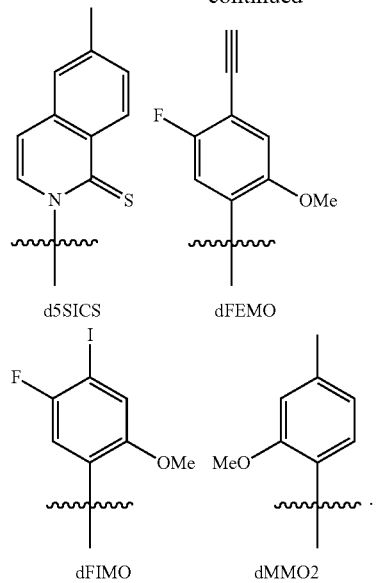

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$ alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON [(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the engineered host cell further comprises a polymerase. In some embodiments, the polymerase is constitutively expressed. In some embodiments, the polymerase is overexpressed. In some embodiments, the polymerase is a DNA polymerase. In some embodiments, the DNA polymerase is DNA polymerase II. In some embodiments, the polymerase is encoded by the polB gene. In some embodiments, the polB gene is derepressed. In some embodiments, the polB gene is derepressed through integration over an operator half site. In some embodiments, the operator is a lexA operator. In some embodiments, the polymerase is DNA polymerase I. In some embodiments, the polymerase is encoded by the polA gene. In some embodiments, the polymerase is DNA polymerase III. In some embodiments, the polymerase is encoded by the dnaQ gene.

Aspects disclosed herein provide methods of increasing the production of a nucleic acid molecule comprising an unnatural nucleotide, comprising: incubating an engineered host cell with a plurality of unnatural nucleotides, wherein the engineered host cell comprises a modified nucleoside triphosphate transporter and optionally, a modified transposition-associated protein or transposable element; and incorporating the plurality of unnatural nucleotides into one or more newly synthesized DNA strands, thereby generating the unnatural nucleic acid molecule; wherein the modified transposition-associated protein or transposable element and the modified nucleoside triphosphate transporter increases retention of unnatural base pairs comprising the unnatural nucleotides in the one or more newly synthesized DNA strands. In some embodiments, the modified transposition-associated protein comprises Insertion element IS1 4 protein InsB, Insertion element IS1 4 protein InsA, or a combination thereof; and wherein the modified transposable element comprises IS1. In some embodiments, the modified nucleoside triphosphate transporter comprises a codon optimized nucleoside triphosphate transporter from *Phaeodactylum tricornutum* ($PtNTT_2$). In some embodiments, the modified nucleoside triphosphate transporter comprises a deletion. In some embodiments, the deletion is a terminal deletion or an internal deletion. In some embodiments, the deletion is an N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the engineered host cell further comprises a Cas9 polypeptide or variants thereof; and a single guide RNA (sgRNA) comprising a crRNA-tracrRNA scaffold, wherein the combination of Cas9 polypeptide or variants thereof and sgRNA modulates replication of the first nucleic acid molecule encoding the unnatural nucleotide. In some embodiments, the sgRNA comprises a target motif that recognizes a modification at the unnatural nucleotide position within the nucleic acid molecule. In some embodiments, the sgRNA further comprises a protospacer adjacent motif (PAM) recognition element. In some embodiments, the PAM element is adjacent to the 3' terminus of the target motif. In some embodiments, the target motif is between 15 to 30 nucleotides in length. In some embodiments, the combination of Cas9 polypeptide or variants thereof and sgRNA decreases the replication rate of the nucleic acid molecule comprising the modification by about 80%, 85%, 95%, 99%, or higher. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of:

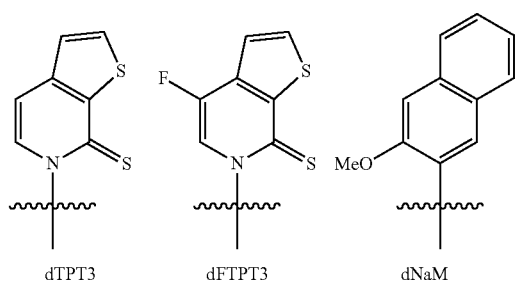

dTPT3    dFTPT3    dNaM

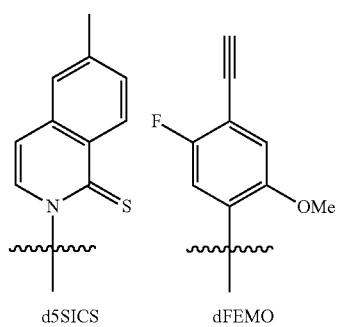

d5SICS    dFEMO

-continued

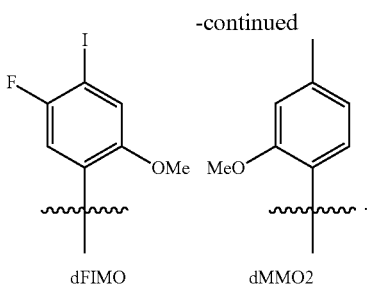

dFIMO    dMMO2

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, poly alkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the engineered host cell further comprises a polymerase. In some embodiments, the polymerase is constitutively expressed. In some embodiments, the polymerase is overexpressed. In some embodiments, the polymerase is a DNA polymerase. In some embodiments, the DNA polymerase is DNA polymerase II. In some embodiments, the polymerase is encoded by the polB gene. In some embodiments, the polB gene is derepressed. In some embodiments, the polB gene is derepressed through integration over an operator half site. In some embodiments, the operator is a lexA operator. In some embodiments, the polymerase is DNA polymerase I. In some embodiments, the polymerase is encoded by the polA gene. In some embodiments, the polymerase is DNA polymerase III. In some embodiments, the polymerase is encoded by the dnaQ gene.

Aspects disclosed herein provide methods of preparing a modified polypeptide comprising an unnatural amino acid, comprising: incubating an engineered host cell with a plurality of unnatural nucleotides, wherein the engineered host cell comprises a modified nucleoside triphosphate transporter and, optionally, a modified transposition-associated protein or transposable element; and incorporating the plurality of unnatural nucleotides into one or more newly synthesized DNA strands, thereby generating the unnatural nucleic acid molecule; wherein the modified transposition-associated protein or transposable element and the modified nucleoside triphosphate transporter increases retention of unnatural base pairs which facilitates incorporation of the plurality of unnatural nucleotides into the newly synthesized polypeptide to generate the modified polypeptide. In some embodiments, the modified transposition-associated protein comprises comprises Insertion element IS1 4 protein InsB, Insertion element IS1 4 protein InsA, or a combination thereof; and wherein the modified transposable element comprises IS1. In some embodiments, the modified nucleoside triphosphate transporter comprises a codon optimized nucleoside triphosphate transporter from *Phaeodactylum tricornutum* (PtNTT$_2$). In some embodiments, the modified nucleoside triphosphate transporter comprises a deletion. In some embodiments, the deletion is a terminal deletion or an internal deletion. In some embodiments, the deletion is an N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the engineered host cell further comprises a Cas9 polypeptide or variants thereof; and a single guide RNA (sgRNA) comprising a crRNA-tracrRNA scaffold, wherein the combination of Cas9 polypeptide or variants thereof and sgRNA modulates replication of the first nucleic acid molecule encoding the unnatural nucleotide. In some embodiments, the sgRNA comprises a target motif that recognizes a modification at the unnatural nucleotide position within the nucleic acid molecule. In some embodiments, the sgRNA further comprises a protospacer adjacent motif (PAM) recognition element. In some embodiments, the PAM element is adjacent to the 3' terminus of the target motif. In some embodiments, the target motif is between 15 to 30 nucleotides in length. In some embodiments, the combination of Cas9 polypeptide or variants thereof and sgRNA decreases the replication rate of the nucleic acid molecule comprising the modification by about 80%, 85%, 95%, 99%, or higher. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thiouracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido [3',2': 4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of:

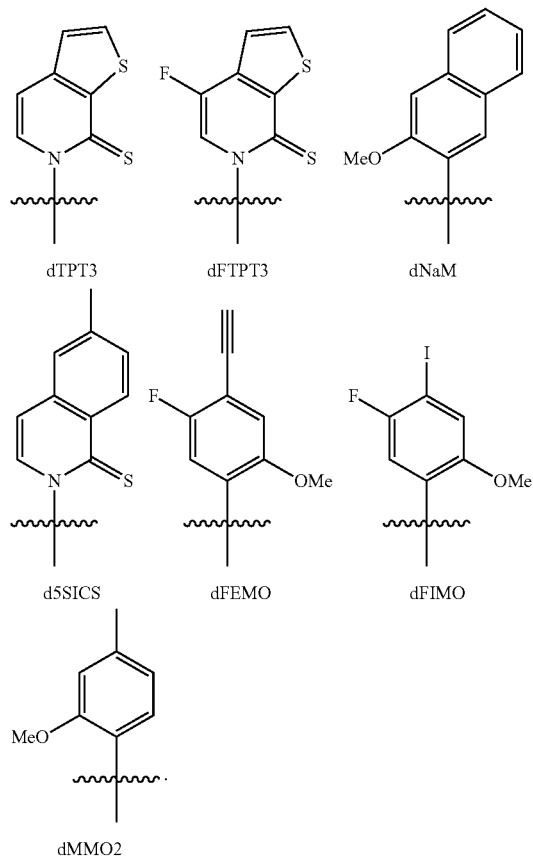

In some embodiments, the unnatural nucleotide further comprises an unnatural sugar moiety selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$ alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, poly alkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the engineered host cell further comprises a polymerase. In some embodiments, the polymerase is constitutively expressed. In some embodiments, the polymerase is overexpressed. In some embodiments, the polymerase is a DNA polymerase. In some embodiments, the DNA polymerase is DNA polymerase II. In some embodiments, the polymerase is encoded by the polB gene. In some embodiments, the polB gene is derepressed. In some embodiments, the polB gene is derepressed through integration over an operator half site. In some embodiments, the operator is a lexA operator. In some embodiments, the polymerase is DNA polymerase I. In some embodiments, the polymerase is encoded by the polA gene. In some embodiments, the polymerase is DNA polymerase III. In some embodiments, the polymerase is encoded by the dnaQ gene.

Aspects disclosed herein provide engineered host cells for producing an unnatural product comprising a modified DNA repair response-associated protein. In some embodiments, the DNA repair response comprises recombinational repair. In some embodiments, the DNA repair response comprises SOS response. In some embodiments, the engineered host cell is a prokaryotic cell, a eukaryotic cell, or a yeast cell. In some embodiments, the engineered host cell is a prokaryotic cell. In some embodiments, the prokaryotic cell is an *Escherichia coli* cell. In some embodiments, the *Escherichia coli* cell is an *Escherichia coli* BL21 (DE3) cell. In some embodiments, the modified DNA repair response-associated protein is RecA. In some embodiments, the engineered host cell is engineered to express a gene encoding RecA. In some embodiments, the modified DNA repair response-associated protein is Rad51. In some embodiments, the engineered host cell is engineered to express a gene encoding Rad51. In some embodiments, the modified DNA repair response-associated protein is RadA. In some embodiments, the modified DNA repair response-associated protein is LexA. In some embodiments, the gene encoding the modified DNA repair response-associated protein comprises one or more mutations, one or more deletions, or a combination thereof. In some embodiments, the gene comprises an N-terminal deletion, a C-terminal deletion, a truncation at both termini, or an internal deletion. In some embodiments, recA, rad51, and/or radA comprises one or more mutations, one or more deletions, or a combination thereof. In some embodiments, recA, rad51, and radA each independently comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347. In some embodiments, lexA comprises one or more mutations, one or more deletions, or a combination thereof. In some embodiments, lexA comprises a mutation at amino acid position S119, optionally a S119A mutation. In some embodiments, the engineered host cell further comprises a polymerase. In some embodiments, the polymerase is constitutively expressed. In some embodiments, the polymerase is overexpressed. In some embodiments, the polymerase is a DNA polymerase. In some embodiments, the DNA polymerase is DNA polymerase II. In some embodiments, the polymerase is encoded by the polB gene. In some embodiments, the polB gene is derepressed. In some embodiments, the polB gene is derepressed through integration over an operator half site. In some embodiments, the operator is a lexA operator. In some embodiments, the polymerase is DNA polymerase I. In some embodiments, the polymerase is encoded by the polA gene. In some embodiments, the polymerase is DNA polymerase III. In some embodiments, the polymerase is encoded by the dnaQ gene.

Aspects disclosed herein provide engineered host cells for producing an unnatural product comprising a modified DNA repair response-associated protein and a polymerase, wherein the polymerase has an elevated expression relative to an equivalent host cell comprising an equivalent polymerase with a basal expression level. In some embodiments, the DNA repair response comprises recombinational repair. In some embodiments, the DNA repair response comprises SOS response. In some embodiments, the polymerase is constitutively expressed. In some embodiments, the polymerase is DNA polymerase II. In some embodiments, the DNA repair response comprises recombinational repair, SOS response, nucleotide excision repair, or methyl-directed mismatch repair. In some embodiments, the DNA repair response comprises recombinational repair. In some embodiments, the DNA repair response comprises SOS response. In some embodiments, the engineered host cell is a prokaryotic cell, a eukaryotic cell, or a yeast cell. In some embodiments, the engineered host cell is a prokaryotic cell. In some embodiments, the prokaryotic cell is an *Escherichia coli* cell. In some embodiments, the *Escherichia coli* cell is an *Escherichia coli* BL21 (DE3) cell. In some embodiments, the modified DNA repair response-associated protein is RecA. In some embodiments, the modified DNA repair response-associated protein is Rad51. In some embodiments, the modified DNA repair response-associated protein is RadA. In some embodiments, the modified DNA repair response-associated protein is LexA. In some embodiments, the gene encoding the defective protein comprises one or more mutations, one or more deletions, or a combination thereof. In some embodiments, the gene comprises an N-terminal deletion, a C-terminal deletion, a truncation at both termini, or an internal deletion. In some embodiments, recA, rad51, and/or radA comprises one or more mutations, one or more deletions, or a combination thereof. In some embodiments, recA, rad51, and radA each independently comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347. In some embodiments, lexA comprises one or more mutations, one or more deletions, or a combination thereof. In some embodiments, lexA comprises a mutation at amino acid position S119, optionally a S119A mutation. In some embodiments, the engineered host cell further comprises a nucleoside triphosphate transporter from *Phaeodactylum tricornutum* (PtNTT$_2$). In some embodiments, the nucleoside triphosphate transporter from PtNTT$_2$ is modified. In some embodiments, the modified nucleoside triphosphate transporter is encoded by a nucleic acid molecule. In some embodiments, the nucleic acid molecule encoding the modified nucleoside triphosphate transporter is incorporated in the genomic sequence of the engineered host cell. In some embodiments, the engineered host cell comprises a plasmid comprising the nucleic acid molecule encoding the modified nucleoside triphosphate transporter. In some embodiments, the modified nucleoside triphosphate transporter is a codon optimized nucleoside triphosphate transporter from *Phaeodactylum tricornutum*. In some embodiments, the modified nucleoside triphosphate transporter comprises a deletion. In some embodiments, the deletion is a terminal deletion or an internal deletion. In some embodiments, the deletion is an N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the modified nucleoside triphosphate transporter is under the control of a promoter selected from a pSC plasmid or a promoter from a lac operon. In some embodiments, the lac operon is an *E. coli* lac operon. In some embodiments, the lac operon is selected from $P_{bla}$, $P_{lac}$, $P_{lacUV5}$, $P_{H207}$, $P_\lambda$, $P_{tac}$, or $P_{N25}$. In some embodiments, the modified nucleoside triphosphate transporter is under the control of promoter $P_{lacUV5}$. In some embodiments, the engineered host cell further comprises a Cas9 polypeptide or variants thereof, and a single guide RNA (sgRNA) comprising a crRNA-tracrRNA scaffold, wherein the combination of Cas9 polypeptide or variants thereof and sgRNA modulates replication of a nucleic acid molecule comprising an unnatural nucleotide. In some embodiments, the sgRNA comprises a target motif that recognizes a modification at the unnatural nucleotide position within the nucleic acid molecule. In some embodiments, the sgRNA further comprises a protospacer adjacent motif (PAM) recognition element. In some embodiments, the PAM element is adjacent to the 3' terminus of the target motif. In some embodiments, the target motif is between 15 to 30 nucleotides in length. In some embodiments, the combination of Cas9 polypeptide or variants thereof and sgRNA decreases the replication rate of the nucleic acid molecule comprising the modification by about 80%, 85%, 95%, 99%, or higher. In some embodiments, the Cas9 polypeptide is a wild-type Cas9. In some embodiments, the engineered host cell further comprises an unnatural nucleotide. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-aminopropyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

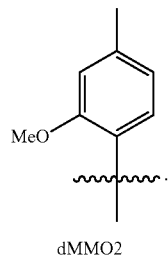

dMMO2

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural base is selected from the group consisting of

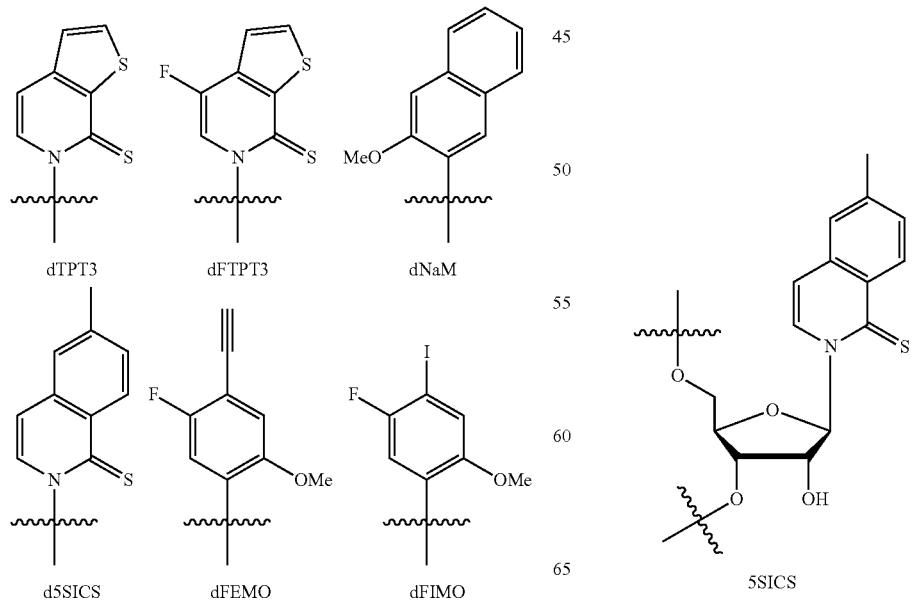

NAM

In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the unnatural nucleotide is dNaMTP and/or dTPT$_3$TP. In some embodiments, the unnatural nucleotide is integrated into the engineered host cell genome. In some embodiments, the unnatural nucleotide is integrated into a chromosome. In some embodiments, the unnatural nucleotide is integrated into an arsB locus. In some embodiments, the engineered host cell enables unnatural base pair retention of about 50%, 55%, 60%, 65%, 70%, 75%, 80%, 85%, 90%, 91%, 92%, 93%, 94%, 95%, 96%, 97%, 98%, 99% or more, relative to an equivalent engineered host cell in the absence of the modified DNA repair response-associated protein or in the absence of the modified DNA repair response-associated protein in combination with the overexpressed polymerase. In some embodiments, the engineered host cell enables unnatural base pair retention at least 50% after more than 50, more than 100, more than 120, more than 130, more than 150, or more than 200 generations. In some embodiments, the engineered host cell enables unnatural base pair retention at least 55% after more than 50, more than 100, more than 120, more than 130, more than 137, more than 150, or more than 200 generations. In some embodiments, the unnatural product is a nucleic acid molecule comprising an unnatural nucleotide. In some embodiments, the unnatural product is a polypeptide comprising an unnatural amino acid. In some embodiments, the engineered host cell is a semi-synthetic organism.

Aspects disclosed herein provide nucleic acid molecules comprising an unnatural nucleotide produced by an engineered host cell described herein.

Aspects disclosed herein provide polypeptide comprising one or more unnatural amino acids produced by an engineered host cell described herein.

Aspects disclosed herein provide methods of increasing fidelity of replication of a nucleic acid molecule comprising an unnatural nucleotide, comprising: (a) incubating an engineered host cell described herein with a plurality of unnatural nucleotides; and (b) incorporating the plurality of unnatural nucleotides into one or more newly synthesized DNA strands, thereby generating the unnatural nucleic acid molecule; wherein the modified DNA repair response-associated protein and optionally the overexpressed polymerase increases fidelity of replication of the unnatural base pairs comprising the unnatural nucleotides in the one or more newly synthesized DNA strands. In some embodiments, the DNA repair response comprises recombinational repair. In some embodiments, the DNA repair response comprises SOS response. In some embodiments, the increased production of the nucleic acid molecule comprising an unnatural nucleotide is relative to the production of the nucleic acid molecule in an equivalent host cell in the absence of the modified DNA repair response-associated protein and optionally the overexpressed polymerase. In some embodiments, the increased production of the nucleic acid molecule is at least 5%, 10%, 20%, 30%, 40%, 50%, 60%, 70%, 80%, 90%, or 99% higher than the production of the nucleic acid molecule in an equivalent host cell in the absence of the modified DNA repair response-associated protein and optionally the overexpressed polymerase. In some embodiments, the increased production of the nucleic acid molecule is more than 1-fold, 2-fold, 3-fold, 4-fold, 5-fold, 10-fold, 15-fold, 20-fold, 25-fold, 30-fold, 40-fold, 50-fold, 100-fold, or higher than the production of the nucleic acid molecule in an equivalent host cell in the absence of the modified DNA repair response-associated protein and optionally the overexpressed polymerase. In some embodiments, the increased production of the nucleic acid molecule is from 1-fold to 5-fold, from 5-fold to 10-fold, from 10-fold to 15-fold, from 15-fold to 20-fold, from 20-fold to 25-fold, from 25-fold to 30-fold, from 30-fold to 40-fold, from 40-fold to 50-fold, from 50-fold to 60-fold, from 60-fold to 70-fold, from 70-fold to 80-fold, from 80-fold to 90-fold, from 90-fold to 100-fold, or from 100-fold to 200-fold higher than the production of the nucleic acid molecule in an equivalent host cell in the absence of the modified DNA repair response-associated protein and optionally the overexpressed polymerase. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methylcytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido [3',2': 4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of nyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural base is selected from the group consisting of

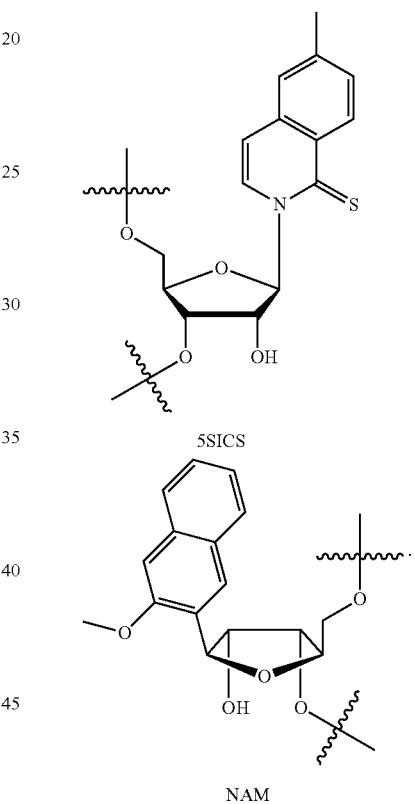

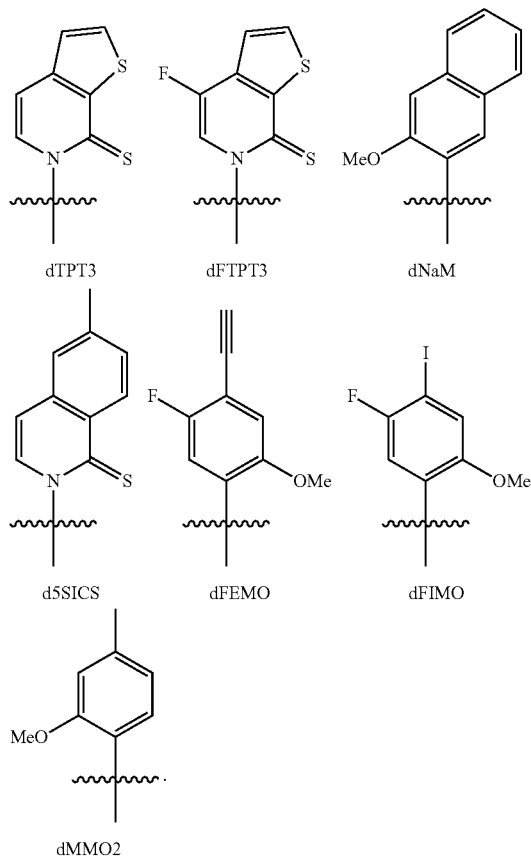

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alky- In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, C$_1$-C$_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the unnatural nucleotide is dNaMTP and/or dTPT$_3$TP. In some embodiments, the unnatural nucleotide is integrated into the engineered host cell genome. In some embodiments, the unnatural nucleotide is integrated into a chromosome. In some embodiments, the unnatural nucleotide is integrated into an arsB locus. In some embodiments, the modified DNA repair response-associated protein is RecA. In some embodiments, the modified DNA repair response-associated protein is Rad51. In some embodiments, the modified DNA repair response-associated protein is RadA. In some embodiments, the modified DNA repair response-associated protein is LexA. In some embodiments, the gene encoding the modified DNA repair response-associated protein comprises one or more mutations, one or more deletions, or a combination thereof. In some embodiments, the gene comprises an N-terminal deletion, a C-terminal deletion, a truncation at both termini, or an internal deletion. In some embodiments, recA, rad51, and/or radA comprises one or more mutations, one or more deletions, or a combination thereof. In some embodiments, recA, rad51, and radA each independently comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347. In some embodiments, lexA comprises one or more mutations, one or more deletions, or a combination thereof. In some embodiments, lexA comprises a mutation at amino acid position S119, optionally a S119A mutation.

Aspects disclosed herein provide methods of increasing the production of a nucleic acid molecule comprising an unnatural nucleotide, comprising: (a) incubating an engineered host cell described herein with a plurality of unnatural nucleotides; and (b) incorporating the plurality of unnatural nucleotides into one or more newly synthesized DNA strands, thereby generating the unnatural nucleic acid molecule; wherein the modified DNA repair response-associated protein and optionally the overexpressed polymerase increases retention of unnatural base pairs comprising the unnatural nucleotides in the one or more newly synthesized DNA strands. In some embodiments, the DNA repair response comprises recombinational repair. In some embodiments, the DNA repair response comprises SOS response. In some embodiments, the increased production of the nucleic acid molecule comprising an unnatural nucleotide is relative to the production of the nucleic acid molecule in an equivalent host cell in the absence of the modified DNA repair response-associated protein and optionally the overexpressed polymerase. In some embodiments, the increased production of the nucleic acid molecule is at least 5%, 10%, 20%, 30%, 40%, 50%, 60%, 70%, 80%, 90%, or 99% higher than the production of the nucleic acid molecule in an equivalent host cell in the absence of the modified DNA repair response-associated protein and optionally the overexpressed polymerase. In some embodiments, the increased production of the nucleic acid molecule is more than 1-fold, 2-fold, 3-fold, 4-fold, 5-fold, 10-fold, 15-fold, 20-fold, 25-fold, 30-fold, 40-fold, 50-fold, 100-fold, or higher than the production of the nucleic acid molecule in an equivalent host cell in the absence of the modified DNA repair response-associated protein and optionally the overexpressed polymerase. In some embodiments, the increased production of the nucleic acid molecule is from 1-fold to 5-fold, from 5-fold to 10-fold, from 10-fold to 15-fold, from 15-fold to 20-fold, from 20-fold to 25-fold, from 25-fold to 30-fold, from 30-fold to 40-fold, from 40-fold to 50-fold, from 50-fold to 60-fold, from 60-fold to 70-fold, from 70-fold to 80-fold, from 80-fold to 90-fold, from 90-fold to 100-fold, or from 100-fold to 200-fold higher than the production of the nucleic acid molecule in an equivalent host cell in the absence of the modified DNA repair response-associated protein and optionally the overexpressed polymerase. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-aminoadenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4] benzoxazin-2(3H)-one), carbazole cytidine (2H-pyrimido[4,5-b]indol-2-one), pyridoindole cytidine (H-pyrido [3',2':4,5] pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

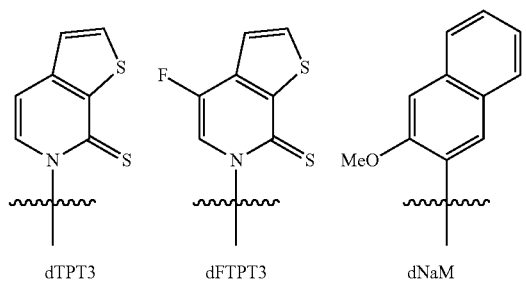

dTPT3  dFTPT3  dNaM

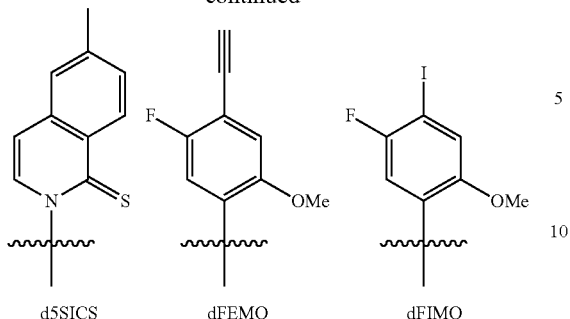

d5SICS     dFEMO     dFIMO

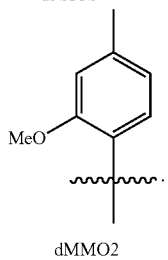

dMMO2

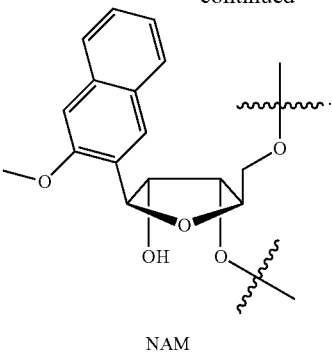

NAM

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$ alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural base is selected from the group consisting of

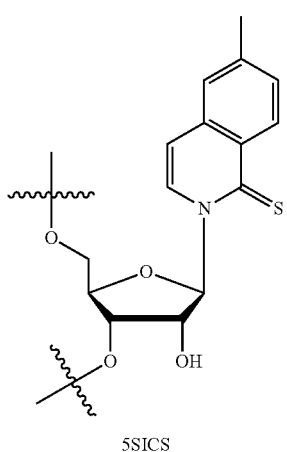

5SICS

In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, C$_1$-C$_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the unnatural nucleotide is dNaMTP and/or dTPT$_3$TP. In some embodiments, the unnatural nucleotide is integrated into the engineered host cell genome. In some embodiments, the unnatural nucleotide is integrated into a chromosome. In some embodiments, the unnatural nucleotide is integrated into an arsB locus. In some embodiments, the modified DNA repair response-associated protein is RecA. In some embodiments, the modified DNA repair response-associated protein is Rad51. In some embodiments, the modified DNA repair response-associated protein is RadA. In some embodiments, the modified DNA repair response-associated protein is LexA. In some embodiments, the gene encoding the modified DNA repair response-associated protein comprises one or more mutations, one or more deletions, or a combination thereof. In some embodiments, the gene comprises an N-terminal deletion, a C-terminal deletion, a truncation at both termini, or an internal deletion. In some embodiments, recA, rad51, and/or radA comprises one or more mutations, one or more deletions, or a combination thereof. In some embodiments, recA, rad51, and radA each independently comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347. In some embodiments, lexA comprises one or more mutations, one or more deletions, or a combination thereof. In some embodiments, lexA comprises a mutation at amino acid position S119, optionally a S119A mutation.

Aspects disclosed herein provide methods of preparing a modified polypeptide comprising an unnatural amino acid, comprising: (a) incubating an engineered host cell described herein with a plurality of unnatural amino acids; and (b) incorporating the plurality of unnatural amino acids into a newly synthesized polypeptide, thereby generating the modified polypeptide; wherein the modified DNA repair response-associated protein and optionally the overexpressed polymerase increases retention of unnatural base pairs which facilitates incorporation of the plurality of unnatural amino acids into the newly synthesized polypeptide to generate the modified polypeptide. In some embodiments, the DNA repair response comprises recombinational repair. In some embodiments, the DNA repair response comprises SOS response. In some embodiments, the modified polypeptide is further conjugated with a conjugating moiety to generate a modified polypeptide conjugate. In some embodiments, the conjugating moiety is a protein or binding fragment thereof, a polymer, a therapeutic agent, an imaging agent, or a combination thereof. In some embodiments, the modified polypeptide is further conjugated with a therapeutic agent. In some embodiments, the modified polypeptide is an imaging agent. In some embodiments, the modified polypeptide conjugate is further formulated with a pharmaceutical excipient to generate a pharmaceutical composition. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-aminoadenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4] benzoxazin-2(3H)-one), carbazole cytidine (2H-pyrimido[4,5-b]indol-2-one), pyridoindole cytidine (H-pyrido [3',2':4,5] pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

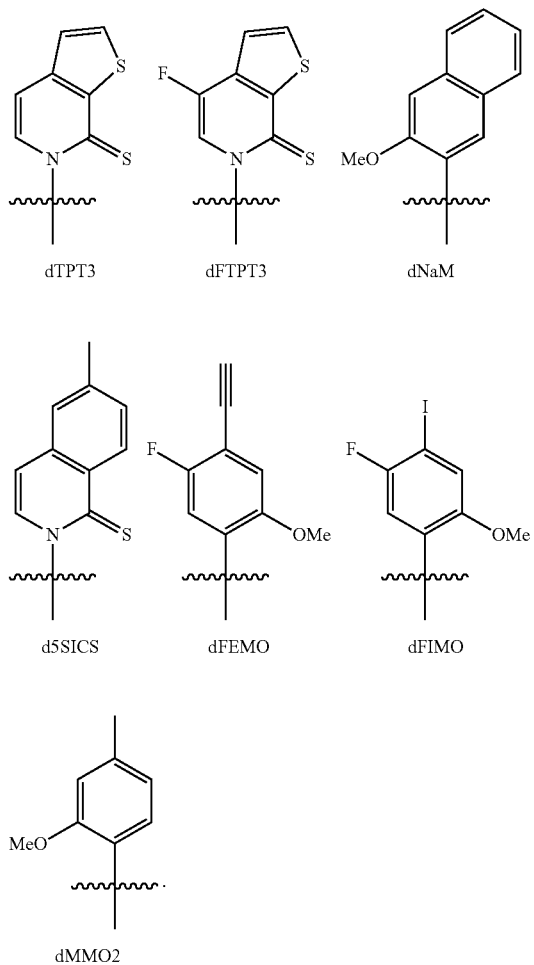

dTPT3   dFTPT3   dNaM d5SICS   dFEMO   dFIMO dMMO2

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON [(CH$_2$)nCH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural base is selected from the group consisting of

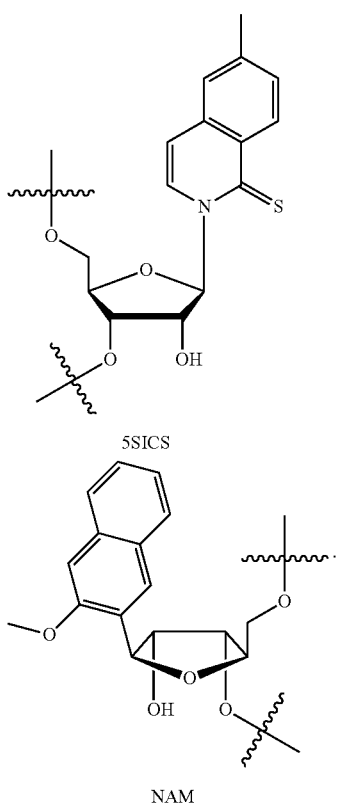

5SICS

NAM

In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the unnatural nucleotide is dNaMTP and/or dTPT$_3$TP. In some embodiments, the unnatural nucleotide is integrated into the engineered host cell genome. In some embodiments, the unnatural nucleotide is integrated into a chromosome. In some embodiments, the unnatural nucleotide is integrated into an arsB locus. In some embodiments, the modified DNA repair response-associated protein is RecA. In some embodiments, the modified DNA repair response-associated protein is Rad51. In some embodiments, the modified DNA repair response-associated protein is RadA. In some embodiments, the modified DNA repair response-associated protein is LexA. In some embodiments, the gene encoding the modified DNA repair response-associated protein comprises one or more mutations, one or more deletions, or a combination thereof. In some embodiments, the gene comprises an N-terminal deletion, a C-terminal deletion, a truncation at both termini, or an internal deletion. In some embodiments, recA, rad51, and/or radA comprises one or more mutations, one or more deletions, or a combination thereof. In some embodiments, recA, rad51, and radA each independently comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347. In some embodiments, lexA comprises one or more mutations, one or more deletions, or a combination thereof. In some embodiments, lexA comprises a mutation at amino acid position S119, optionally a S119A mutation.

Aspects disclosed herein provide methods of treating a disease or condition, comprising administering to a subject in need thereof a pharmaceutical composition comprising a modified polypeptide prepared by the methods disclosed herein, thereby treating the disease or condition.

Aspects disclosed herein provide kits comprising an engineered host cells described herein.

Aspects disclosed herein provide engineered host cells for producing an unnatural product comprising a modified RecA. In some embodiments, a gene encoding the modified RecA comprises one or more mutations, one or more deletions, or a combination thereof. In some embodiments, the gene comprises an N-terminal deletion, a C-terminal deletion, a truncation at both termini, or an internal deletion. In some embodiments, recA comprises an N-terminal deletion, a C-terminal deletion, a truncation at both termini, or an internal deletion. In some embodiments, recA comprises an internal deletion of residues 2-347.

Aspects disclosed herein provide engineered host cells for producing an unnatural product comprising a modified RecA and an overexpressed DNA polymerase II, wherein the expression level of the overexpressed DNA polymerase II is relative to an equivalent host cell comprising an equivalent DNA polymerase II with a basal expression level.

Aspects disclosed herein provide methods of increasing the production of a nucleic acid molecule comprising an unnatural nucleotide, comprising: (a) incubating an engineered host cell with a plurality of unnatural nucleotides, wherein the engineered host cell comprises a modified RecA and optionally an overexpressed DNA polymerase II, and wherein the expression level of the overexpressed DNA polymerase II is relative to an equivalent host cell comprising an equivalent DNA polymerase II with a basal expression level; and (b) incorporating the plurality of unnatural nucleotides into one or more newly synthesized DNA strands, thereby generating the unnatural nucleic acid molecule; wherein the modified DNA repair response-associated protein and optionally the overexpressed polymerase increases retention of unnatural base pairs comprising the unnatural nucleotides in the one or more newly synthesized DNA strands.

Aspects disclosed herein provide methods of preparing a modified polypeptide comprising an unnatural amino acid, comprising: (a) incubating an engineered host cell with a plurality of unnatural amino acids, wherein the engineered host cell comprises a modified RecA and optionally an overexpressed DNA polymerase II, and wherein the expression level of the overexpressed DNA polymerase II is relative to an equivalent host cell comprising an equivalent DNA polymerase II with a basal expression level; and (b)incorporating the plurality of unnatural amino acids into a newly synthesized polypeptide, thereby generating the modified polypeptide; wherein the modified DNA repair response-associated protein and optionally the overexpressed polymerase increases retention of unnatural base pairs which facilitates incorporation of the plurality of unnatural amino acids into the newly synthesized polypeptide to generate the modified polypeptide. In some embodiments, the DNA repair response comprises recombinational repair. In some embodiments, the DNA repair response comprises SOS response. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thiothymine, uracil-5-yl, hypoxanthin-9-yl (I), 5-methylcytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido [3',2': 4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

In some embodiments, the unnatural base is selected from the group consisting of

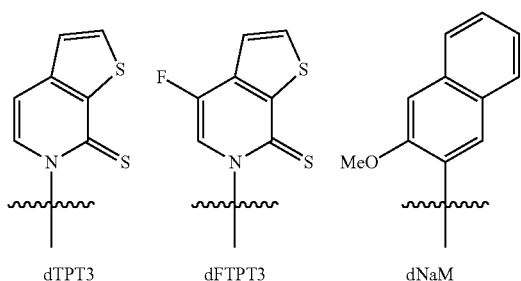

dTPT3   dFTPT3   dNaM

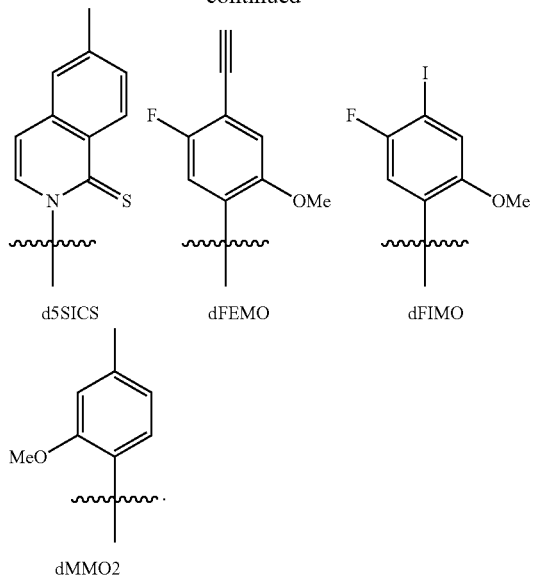

d5SICS   dFEMO   dFIMO dMMO2

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'-$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, —$O[(CH_2)nO]mCH_3$, —$O(CH_2)nOCH_3$, —$O(CH_2)nNH_2$, —$O(CH_2)nCH_3$, —$O(CH_2)n$-$ONH_2$, and —$O(CH_2)nON$ $[(CH_2)nCH_3)]_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural base is selected from the group consisting of

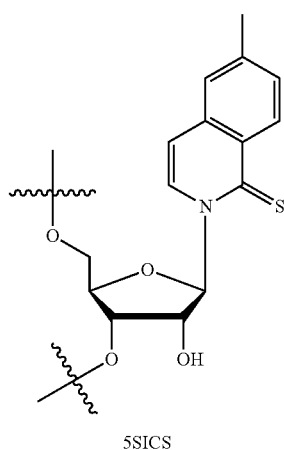

5SICS

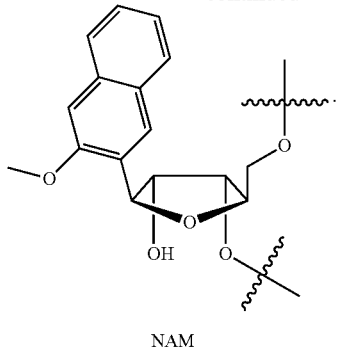

NAM

In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the unnatural nucleotide is dNaMTP and/or dTPT$_3$TP. In some embodiments, the unnatural nucleotide is integrated into the engineered host cell genome. In some embodiments, the unnatural nucleotide is integrated into a chromosome. In some embodiments, the unnatural nucleotide is integrated into an arsB locus.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates the dNaM-dTPT$_3$ UBP and a natural dG-dC base pair. FIG. 1B illustrates the strains deficient for NER (ΔuvrC), MMR (ΔmutH), or RER (ΔrecA). FIG. 1C illustrates strains deficient for RER and SOS (ΔrecA) and strains deficient only for SOS (lexA (S119A)). FIG. 1D illustrates strains deficient for the SOS regulated polymerases Pol II (ΔpolB) or Pols IV and V (ΔdinBΔumuCD) or RER and SOS (ΔrecA). FIG. 1E illustrates strains with Pol I$^{exo-}$ (polA(D424A, K890R)) or Pol III$^{exo-}$ (dnaQ(D12N)) in wild-type, ΔpolB, or ΔpolBΔrecA backgrounds. In each case the indicated strains were challenged with replicating a plasmid with the UBP embedded within the sequence indicated (X=dNaM). n≥3 for all data shown; points represent individual replicates; bars represent sample means; error bars represent S.D.

FIG. 2A illustrates that retention of UBP in individual clones of WT-Opt (medium grey), ΔrecA-Opt (dark grey), and Pol II$^+$ΔrecA-Opt (light grey) after selection on solid growth media. Each strain was challenged with replicating pINF-borne UBPs in sequence contexts of varying difficulty (GTAXAGA<TCCXCGT<TCCXGGT). Each point represents and individual clone, and n≥12 for each distribution. FIG. 2B illustrates growth curves of chromosomal UBP integrants of WT-Opt (medium grey), ΔrecA-Opt (dark grey), and Pol II$^+$ΔrecA-Opt (light grey) cells during exponential phase growth in media with (circles/solid lines) and without (squares/dotted lines) dNaMTP and dTPT3TP. Data is fit with theoretical exponential growth curves. n=3; small points represent individual replicates; large points represent sample means; error bars for time and OD600 represent S.D. FIG. 2C illustrates retention of the chromosomal dNaM-dTPT3 UBP in WT-Opt (medium grey), ΔrecA-Opt (dark grey), and Pol II$^+$ΔrecA-Opt (light grey) cells was measured over long-term growth. n=3; small points represent individual replicates; large points represent sample means; error bars represent two S.D. for both cell doublings and retention except for Pol II$^+$ΔrecA-Opt data. After approximately seventy doublings, one replicate of Pol II$^+$ΔrecA-Opt strain was contaminated with WT-Opt cells. Therefore, data at and after the black arrow represent the mean of only two independent experiments for Pol II$^+$ΔrecA-Opt.

FIG. 4A shows pACS2 was used to generate all data provided in FIG. 1B-FIG. 1E, except for Pol III$^{Exo-}$ strains. FIG. 4B shows pACS2+dnaQ(D12N) was used to generate Pol IIIexo– strain data. FIG. 4C shows chromosomal expression from the lacZYA locus was used to generate all FIG. 2A-FIG. 2C data.

FIG. 6A shows that polA was truncated to its 5" - - - 3" exonuclease domain (corresponding to PolA(1-341)). Then the desired D424A mutation was introduced. The K890R mutation occurred in PCR and was predicted to have limited impact on Pol I function. FIG. 6B shoes that PpolB was derepressed (PPol II+) through integration over one of the lexA operator half sites (bold) present upstream of the –35 sequence of the promoter.

FIG. 7A shows construction strategy of the arsB::UBP integration cassette. The integration cassette was constructed through overlapping PCR of a short UBP containing DNA and the neo cassette of the pKD13 plasmid. FIG. 7B shows successful integration of a chromosomal UBP was confirmed by PCR and biotin shift PCR. Confirmation of ΔrecA-Opt and Pol II$^+$ΔrecA-Opt SSO integrants (A2 and B3 respectively) is shown. Teal bands indicate overexposure. FIG. 7C shows replating initial integrants and isolating individual clones quickly identified 100% retention clones for ΔrecA-Opt and Pol II+ ΔrecA-Opt (A2.1 and B3.1 respectively). The same procedure for a WT-Opt integrant (C1) did not. A representative subset of replated clones is shown. Red bands indicate overexposure. In panels B and C, the identities of the primer sets used to produce each gel are given above each gel. Molecular weights are provided next to size standards in number of base pairs. When relevant % Shift values are provided below lanes and streptavidin-DNA and DNA species are indicated with black and red arrows, respectively.

FIG. 8A shows growth curves for reprogrammed strains without a chromosomal UBP (WT-Opt (red), ΔrecA-Opt (blue), and Pol II+ ΔrecA-Opt (gold)) and wild-type BL21(DE3) with chloramphenicol resistance (lacZYA::cat (black)) are shown. Circles/solid lines represent growth in media with dNaMTP and dTPT3TP. Squares/dotted lines represent growth in media without dNaMTP and dTPT3TP. FIG. 8B shows the average measured doubling times (n=3) are presented for all strains with and without a chromosomal UBP and with and without the addition of dXTPs. FIG. 6B discloses SEQ ID NOS 28 and 29, respectively, in order of appearance.

FIG. 9A shows the PpoIB locus was monitored by PCR of gDNA samples from passaging of replicate 3 for the Pol II+ ΔrecA-Opt integrant. Strains with the PPol II+ mutation produce a larger amplicon than wild-type BL21(DE3) with chloramphenicol resistance (lacZYA::cat) (a) as seen from analysis of Pol II+ ΔrecA-Opt before UBP integration (b). FIG. 9B shows the recA locus was monitored by PCR of gDNA samples from passaging of replicate 3 for the Pol II+ ΔrecA-Opt integrant. Strains with the ΔrecA mutation produce a smaller amplicon than wild-type BL21(DE3) with chloramphenicol resistance (lacZYA::cat) (a) as seen from analysis of Pol II+ ΔrecA-Opt before UBP integration (b).

FIG. 10A shows during passaging WT-Opt mutants arose where region between cat and IS1 (top panel) was truncated to the C-terminus of PtNTT2(66-575) and IS1 (middle panel). Sequencing confirmed this transposition (bottom panel). FIG. 10A discloses SEQ ID NOS 30-32, respectively, in order of appearance. FIG. 10B shows inactivation of PtNTT2(66-575) by the IS1 transposon was monitored by PCR of gDNA from passaging of WT-Opt. Transposition events inactivate PtNTT2(66-575) and range in size between ~3000-4000 bp. Inactivation occurs during the rapid phase of UBP loss. An additional amplicon (approximately 1500 bp in size) is also produced by these primers in wild-type BL21(DE3) with chloramphenicol resistance (lacZYA::cat) (a), WT-Opt before UBP integration (b), and wild-type BL21(DE3) (c).

DETAILED DESCRIPTION OF THE INVENTION

Figure 1A:
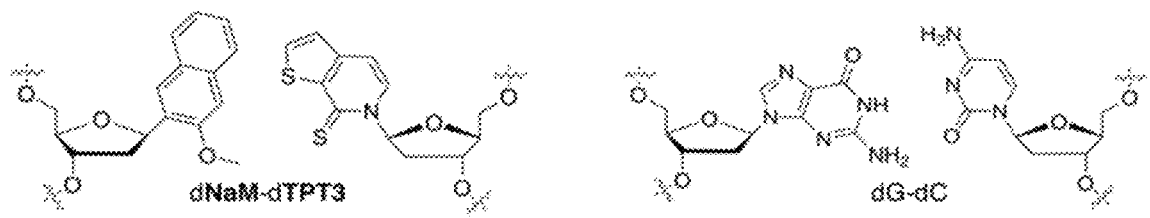
FIG. 1A-FIG. 1E illustrate unnatural base pairs (UBPs) and the contribution of DNA damage and tolerance pathways to its retention.

The development of an unnatural base pair (UBP) allowing cells to store and retrieve increased information has a profound effect in practical applications, including human health applications by facilitating the production of proteins containing unnatural amino acids for development as therapeutics. However, retention of the UBP within a population of cells is sequence-dependent and in some sequences, the UBP is not sufficiently maintained or maintained at a reduced level, for practical applications (e.g. protein expression), thereby limiting the number of codons available for use.

Although loss of the UBP during extended growth may be mitigated by applying selection pressure for triphosphate uptake and UBP retention via expression of Cas9 directed to cleave, and thus degrade DNA sequences that have lost the UBP, retention remains challenging in some sequence contexts. Moreover, this approach requires optimizing different guide RNAs for every sequence to be retained, which is challenging with many applications, for example, those involving propagation of random DNA sequences. In addition, encoding information with the UBP in the chromosome as opposed to a plasmid, was expected to be incompatible with applying this selection pressure due to undesired cleavage of UBP-containing sequences and/or because cleavage would result in destruction of the chromosome as opposed to the less consequential elimination of one of many copies of a plasmid.

Disclosed herein, in some embodiments are methods, compositions, cells, engineered microorganisms, plasmids, and kits for increased retention of a UBP utilizing modified DNA repair-associated proteins, e.g., proteins involved in recombinational repair, SOS response, nucleotide excision repair, or methyl-directed mismatch repair, and/or modified transposition-associated proteins, e.g., Insertion element IS1 4 protein InsB, Insertion element IS1 4 protein InsA. In some instances, constitutive expression or overexpression of DNA repair-associated proteins, and/or deletion of, or reduced expression, of transposition-associated proteins, facilitates the increased stability of the nucleoside triphosphate transporter resulting in the creation of SSOs characterized by an increased in UBP chromosomal retention.

Disclosed herein, in certain embodiments, are methods, compositions, cells, engineered microorganisms, plasmids, and kits for increased production of a nucleic acid molecule that comprises an unnatural nucleotide. In some instances, disclosed herein are engineered cells comprising: (a) a first nucleic acid molecule comprising an unnatural nucleotide; and (b) a second nucleic acid molecule encoding a modified transposition-associated protein. In some embodiments, the engineered cell further comprises a third nucleic acid molecule encoding a modified nucleoside triphosphate transporter, wherein the third nucleic acid molecule is incorporated in a genomic sequence of the engineer host cell, or comprises a plasmid encoding the modified nucleoside triphosphate transporter. In some embodiments, the engineered cell further comprises a Cas9 polypeptide or variants thereof; and a single guide RNA (sgRNA) comprising a crRNA-tracrRNA scaffold, wherein the combination of Cas9 polypeptide or variants thereof and sgRNA modulates replication of the first nucleic acid molecule encoding the unnatural nucleotide. In certain embodiments, the engineered cell further comprises: (a) a fourth nucleic acid molecule encoding a Cas9 polypeptide or variants thereof; and (b) a fifth nucleic acid molecule encoding a single guide RNA (sgRNA) comprising a crRNA-tracrRNA scaffold. In some instances, the first, second, third, fourth, and fifth nucleic acid molecules, are encoded in one or more plasmids, and the sgRNA encoded by the fifth nucleic acid molecule comprises a target motif that recognizes a modification at the unnatural nucleotide position within the first nucleic acid molecule.

In some embodiments, further provided herein include a nucleic acid molecule containing an unnatural nucleotide produced by a process comprising incubating an engineered cell with: (a) a first nucleic acid molecule comprising an unnatural nucleotide; (b) a second nucleic acid molecule encoding a modified transposition-associated protein; (c) a third nucleic acid molecule encoding a modified nucleoside triphosphate transporter; (d) a fourth nucleic acid molecule encoding a Cas9 polypeptide or variants thereof; and (e) a fifth nucleic acid molecule encoding a single guide RNA (sgRNA) comprising a crRNA-tracrRNA scaffold. In some instances, a modification at the unnatural nucleotide position within the first nucleic acid molecule generates a modified first nucleic acid molecule, and the combination of the Cas9 polypeptide or variants thereof and sgRNA modulates replication of the modified first nucleic acid molecule leading to production of the nucleic acid molecule containing an unnatural nucleotide. In some instances, expression of the modified transposition-associated protein in the engineered cell increases the stability of the triphosphate transporter. In some embodiments, increased stability of the triphosphate transporter contributes to an increase in the (i) production of a modified polypeptide comprising an unnatural amino acid encoded by the unnatural nucleotide, and/or (ii) increased retention of the unnatural nucleotide in the genome of the engineered cell.

In some embodiments, additional provided herein include a semi-synthetic organism (SSO) produced by a process comprising incubating an organism with: (a) a first nucleic acid molecule comprising an unnatural nucleotide; (b) a second nucleic acid molecule encoding a modified transposition-associated protein; (c) a third nucleic acid molecule encoding a modified nucleoside triphosphate transporter; (d) a fourth nucleic acid molecule encoding a Cas9 polypeptide or variants thereof; and (e) a fifth nucleic acid molecule encoding a single guide RNA (sgRNA) comprising a crRNA-tracrRNA scaffold. In some instances, a modification at the unnatural nucleotide position within the first nucleic acid molecule generates a modified first nucleic acid molecule, and the combination of the Cas9 polypeptide or variants thereof and the sgRNA modulates replication of the modified first nucleic acid molecule leading to production of the semi-synthetic organism containing a nucleic acid molecule comprising an unnatural nucleotide. In some instances, expression of the modified transposition-associated protein in the engineered cell increases the stability of the triphosphate transporter. In some embodiments, increased stability of the triphosphate transporter contributes to an increase in the (i) production of a modified polypeptide comprising an unnatural amino acid encoded by the unnatural nucleotide, and/or (ii) increased retention of the unnatural nucleotide in the genome of the SSO.

DNA Repair Machinery

DNA repair mechanisms include nucleotide excision repair (NER), ribonucleotide excision repair (RER), the SOS response, methyl-directed mismatch repair (MMR), and recombinational repair. NER, MMR, RER, and the SOS response, are induced by signals, which may be mimicked by UBP introduction into the host genome. Non-limiting examples of DNA repair-associated proteins in prokaryotic cells involved in the recombinational repair and/or SOS response include RecA, Rad51, RadA, and LexA. Non-limiting examples of DNA repair-associated proteins in prokaryotic cells involved in recombinational repair include RecO, RecR, RecN, and RuvABC. Non-limiting examples of DNA repair-associated proteins in prokaryotic cells involved in NER include UvrA, and UvrB. Non-limiting examples of DNA repair-associated proteins in prokaryotic cells involved in MMR include MutS, MutH, and MutL.

In some embodiments, modified DNA repair-associated proteins are introduced in an engineered cell, or SSO, described herein, to increase chromosomal UBP retention. In some embodiments, the modified DNA repair-associated proteins comprise a deletion of RecA, Rad51, RadA, LexA, RecO, RecR, RecN, RuvABC, MutS, MutH, MutL, UvrA, and/or UvrB. In some embodiments, the deletion comprises an N-terminal deletion, a C-terminal deletion, a truncation at both termini, an internal deletion, and/or a deletion of the entire gene. In some embodiments, a deletion or mutation in a nucleic acid molecule encoding the DNA repair-associated protein is modified to achieve the deletion.

Transposition-Associated Proteins

In $E.\ coli$, there are replicative and conservative (nonreplicative) modes of transposition of a transposable element (e.g., IS1) comprises of a nucleic acid sequence. In the replicative pathway, a new copy of the transposable element is generated in the transposition event. The results of the transposition are that one copy appears at the new site and one copy remains at the old site. In the conservative pathway, there is no replication. Instead, the element is excised from the chromosome or plasmid and is integrated into the new site. In these cases, DNA replication of the element does not occur, and the element is lost in the site of the original chromosome. Deletions of transposable elements cause a high incidence of deletions in their vicinity (e.g., deletion of the transposable element in addition to flanking or surrounding DNA).

The insB-4 and insA-4 genes encode two proteins required for the transposition of the IS1 transposon, InsB, and InsA. The IS1 transposition results in a 9 to 8 base pair target duplication. Deletion of insB-4 results in repression of aberrant transposition events mediated by InsB.

In some embodiments, the methods, engineered cells, and semi-synthetic organisms, described herein comprise a modified nucleic acid molecule encoding a transposition-associated protein. In some embodiments, the transposition-associated protein comprises insB, and/or insA. In some embodiments, the modified nucleic acid molecule encoding a transposition-associated protein comprises a deletion, or a mutation. In some embodiments, the deletion comprises an N-terminal deletion, a C-terminal deletion, a truncation at both termini, an internal deletion, and/or a deletion of the entire gene. In some embodiments, the mutation results in decreased expression of insB and/or InsA. In some embodiments, the deletion or mutation of the modified nucleic acid molecule encoding the transposition-associated protein is effective to stabilize expression and/or activity of the triphosphate nucleotide transporter, thereby increasing retention of the UBP.

In some embodiments, the methods, engineered cells, and semi-synthetic organisms, described herein comprise a modified nucleic acid molecule encoding the IS1 transposable element. In some embodiments, the modified nucleic acid molecule encoding the IS1 transposable element comprises a deletion, or a mutation. In some embodiments, the deletion comprises a knockout or knockdown of all, or part of the nucleic acid molecule encoding the IS1 transposon. In some embodiments, the mutation results in decreased expression of the IS1 transposon. In some embodiments, the deletion or mutation of the modified nucleic acid molecule encoding the IS1 transposon is effective to stabilize expression and/or activity of the triphosphate nucleotide transporter, thereby increasing retention of the UBP. In some instances, the modified nucleic acid molecule encoding the IS1 transposable element comprises SEQ ID NO. 4.

CRISPR/CRISPR-Associated (Cas) Editing System

In some embodiments, methods, cells, and engineered microorganisms disclosed herein utilize a CRISPR/CRISPR-associated (Cas) system for modification of a nucleic acid molecule comprising an unnatural nucleotide. In some instances, the CRISPR/Cas system modulates retention of a modified nucleic acid molecule that comprises a modification at its unnatural nucleotide position. In some instances, the retention is a decrease in replication of the modified nucleic acid molecule. In some instances, the CRISPR/Cas system generates a double-stranded break within a modified nucleic acid molecule leading to degradation involving DNA repair proteins such as RecBCD and its associated nucleases.

In some embodiments, the CRISPR/Cas system involves (1) an integration of short regions of genetic material that are homologous to a nucleic acid molecule of interest comprising an unnatural nucleotide, called "spacers", in clustered arrays in the host genome, (2) expression of short guiding RNAs (crRNAs) from the spacers, (3) binding of the crRNAs to specific portions of the nucleic acid molecule of interest referred to as protospacers, and (4) degradation of protospacers by CRISPR-associated nucleases (Cas). In some cases, a Type-II CRISPR system has been described in the bacterium Streptococcus pyogenes, in which Cas9 and two non-coding small RNAs (pre-crRNA and tracrRNA (trans-activating CRISPR RNA)) act in concert to target and degrade a nucleic acid molecule of interest in a sequence-specific manner (Jinek et al., "A Programmable Dual-RNA-Guided DNA Endonuclease in Adaptive Bacterial Immunity," Science 337(6096):816-821 (August 2012, epub Jun. 28, 2012)).

In some instances. the two noncoding RNAs are further fused into one single guide RNA (sgRNA). In some instances, the sgRNA comprises a target motif that recognizes a modification at the unnatural nucleotide position within a nucleic acid molecule of interest. In some embodiments, the modification is a substitution, insertion, or deletion. In some cases, the sgRNA comprises a target motif that recognizes a substitution at the unnatural nucleotide position within a nucleic acid molecule of interest. In some cases, the sgRNA comprises a target motif that recognizes a deletion at the unnatural nucleotide position within a nucleic acid molecule of interest. In some cases, the sgRNA comprises a target motif that recognizes an insertion at the unnatural nucleotide position within a nucleic acid molecule of interest.

In some cases, the target motif is between 10 to 30 nucleotides in length. In some instances, the target motif is between 15 to 30 nucleotides in length. In some cases, the target motif is about 11, 12, 13, 14, 15, 16, 17, 18, 19, 20, 21, 22, 23, 24, 25, 26, 27, 28, 29, or 30 nucleotides in length. In some cases, the target motif is about 15, 16, 17, 18, 19, 20, 21, or 22 nucleotides in length.

In some cases, the sgRNA further comprises a protospacer adjacent motif (PAM) recognition element. In some instances, PAM is located adjacent to the 3' terminus of the target motif. In some cases, a nucleotide within the target motif that forms Watson-Crick base pairing with the modification at the unnatural nucleotide position within the nucleic acid molecule of interest is located between 3 to 22, between 5 to 20, between 5 to 18, between 5 to 15, between 5 to 12, or between 5 to 10 nucleotides from the 5' terminus of PAM. In some cases, a nucleotide within the target motif that forms Watson-Crick base pairing with the modification at the unnatural nucleotide position within the nucleic acid molecule of interest is located about 3, 4, 5, 6, 7, 8, 9, 10, 11, 12, 13, 14, or 15 nucleotides from the 5' terminus of PAM.

In some instances, a CRISPR/Cas system utilizes a Cas9 polypeptide or a variant thereof. Cas9 is a double stranded nuclease with two active cutting sites, one for each strand of the double helix. In some instances, the Cas9 polypeptide or variants thereof generate a double-stranded break. In some cases, the Cas9 polypeptide is a wild-type Cas9. In some instances, the Cas9 polypeptide is an optimized Cas9 for expression in a cell and/or engineered microorganism described herein.

In some embodiments, the Cas9/sgRNA complex binds to a portion of the nucleic acid molecule of interest (e.g., DNA) that contains a sequence match to, for example, the 17-20 nucleotides of the sgRNA upstream of PAM. Once bound, two independent nuclease domains in Cas9 then each cleaves one of the DNA strands 3 bases upstream of the PAM, leaving a blunt end DNA double stranded break (DSB). The presence of DSB then results, in some instances, to degradation of the DNA of interest by RecBCD and its associated nucleases.

In some instances, the Cas9/sgRNA complex modulates retention of a modified nucleic acid molecule that comprises a modification at its unnatural nucleotide position. In some instances, the retention is a decrease in replication of the modified nucleic acid molecule. In some cases, the Cas9/sgRNA decreases the replication rate of the modified nucleic acid molecule by about 80%, 85%, 95%, 99%, or higher.

In some instances, the production of the nucleic acid molecule comprising an unnatural nucleotide increases by about 30%, 40%, 50%, 55%, 60%, 65%, 70%, 75%, 80%, 85%, 90%, 95%, 96%, 97%, 98%, 99%, or higher. In some instances, the production of the nucleic acid molecule comprising an unnatural nucleotide increases by about 50%, 60%, 70%, 80%, 90%, 95%, 96%, 97%, 98%, 99%, or higher.

In some cases, the retention of the nucleic acid molecule comprising an unnatural nucleotide increases by about 30%, 40%, 50%, 55%, 60%, 65%, 70%, 75%, 80%, 85%, 90%, 95%, 96%, 97%, 98%, 99%, or higher. In some instances, the retention of the nucleic acid molecule comprising an unnatural nucleotide increases by about 50%, 60%, 70%, 80%, 90%, 95%, 96%, 97%, 98%, 99%, or higher.

In some embodiments, the CRISPR/Cas system comprises two or more sgRNAs. In some instances, each of the two or more sgRNAs independently comprises a target motif that recognizes a modification at the unnatural nucleotide position within a nucleic acid molecule of interest. In some embodiments, the modification is a substitution, insertion, or deletion. In some cases, each of the two or more sgRNAs comprises a target motif that recognizes a substitution at the unnatural nucleotide position within a nucleic acid molecule of interest. In some cases, each of the two or more sgRNAs comprises a target motif that recognizes a deletion at the unnatural nucleotide position within a nucleic acid molecule of interest. In some cases, each of the two or more sgRNAs comprises a target motif that recognizes an insertion at the unnatural nucleotide position within a nucleic acid molecule of interest.

In some embodiments, the specificity of binding of the CRISPR components to the nucleic acid molecule of interest is controlled by the non-repetitive spacer elements in the pre-crRNA portion of sgRNA. which upon transcription along with the tracrRNA portion, directs the Cas9 nuclease to the protospacer:crRNA heteroduplex and induces double-strand breakage (DSB) formation. In some instances, the specificity of sgRNA is about 80%., 85%, 90%, 95%, 96%, 97%, 98%, 99%, or higher. In some instances, sgRNA has less than about 20%, 15%, 10%, 5%, 3%, 1%, or less off-target binding rate.

Nucleic Acid Molecules

In some embodiments, a nucleic acid (e.g., also referred to herein as nucleic acid molecule of interest) is from any source or composition, such as DNA, cDNA, gDNA (genomic DNA), RNA, siRNA (short inhibitory RNA), RNAi, tRNA, mRNA or rRNA (ribosomal RNA), for example, and is in any form (e.g., linear, circular, supercoiled, single-stranded, double-stranded, and the like). In some embodiments, nucleic acids comprise nucleotides, nucleosides, or polynucleotides. In some cases, nucleic acids comprise natural and unnatural nucleic acids. In some cases, a nucleic acid also comprises unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phagemid, autonomously replicating sequence (ARS), centromere, artificial chromosome, yeast artificial chromosome (e.g., YAC) or other nucleic acid able to replicate or be replicated in a host cell. In some cases, an unnatural nucleic acid is a nucleic acid analogue. In additional cases, an unnatural nucleic acid is from an extracellular source. In other cases, an unnatural nucleic acid is available to the intracellular space of an organism provided herein, e.g., a genetically modified organism.

Unnatural Nucleic Acids

A nucleotide analog, or unnatural nucleotide, comprises a nucleotide which contains some type of modification to either the base, sugar, or phosphate moieties. In some embodiments, a modification comprises a chemical modification. In some cases, modifications occur at the 3'OH or 5'OH group, at the backbone, at the sugar component, or at the nucleotide base. Modifications, in some instances, optionally include non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect, a modified backbone comprises a backbone other than a phosphodiester backbone. In one aspect, a modified sugar comprises a sugar other than deoxyribose (in modified DNA) or other than ribose (modified RNA). In one aspect, a modified base comprises a base other than adenine, guanine, cytosine or thymine (in modified DNA) or a base other than adenine, guanine, cytosine or uracil (in modified RNA).

In some embodiments, the nucleic acid comprises at least one modified base. In some instances, the nucleic acid comprises 2, 3, 4, 5, 6, 7, 8, 9, 10, 15, 20, or more modified bases. In some cases, modifications to the base moiety include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes, but is not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—Cl¼) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-aminoadenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, Jl., Ed., John Wiley & Sons, 1990, 858-859; Englisch et al., Angewandte Chemie, International Edition, 1991, 30, 613; and Sanghvi, Chapter 15, Antisense Research and Applications, Crookeand Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acid in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo [2.3-d]pyrimidin-5-yl, 2-amino-4-oxopyrolo [2, 3-d] pyrimidin-5-yl, 2-amino-4-oxopyrrolo [2.3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, a modified base of a unnatural nucleic acid is depicted below, wherein the wavy line identifies a point of attachment to the (deoxy)ribose or ribose.

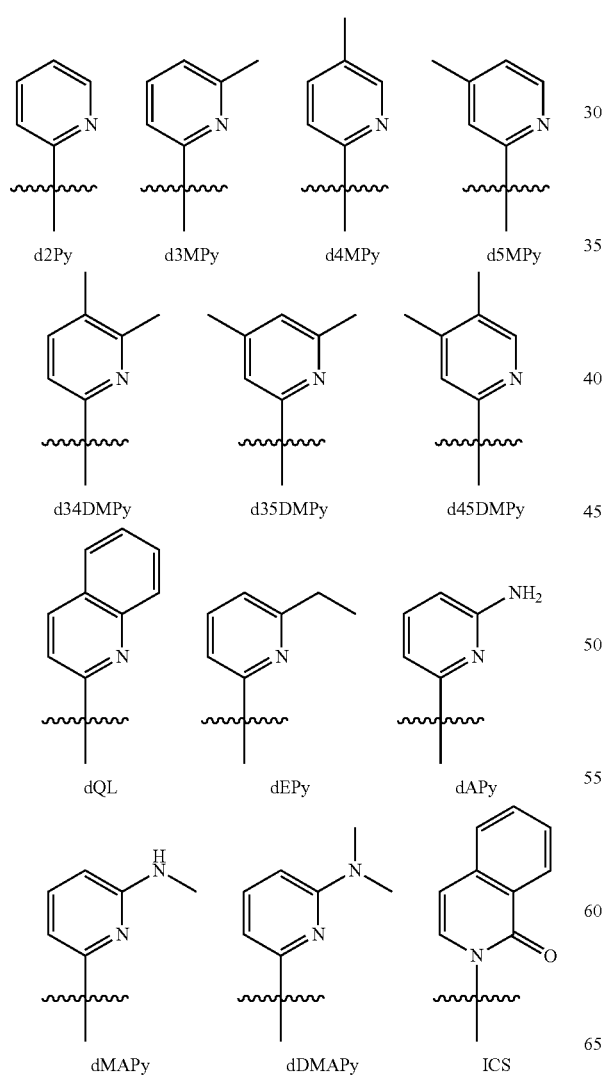

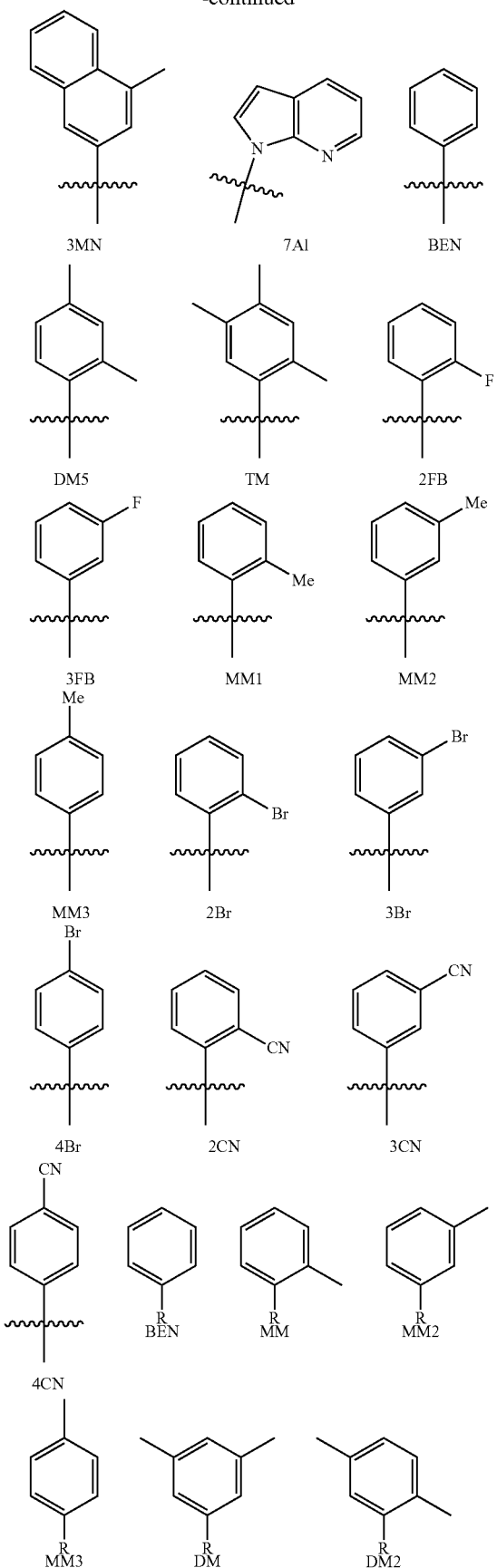

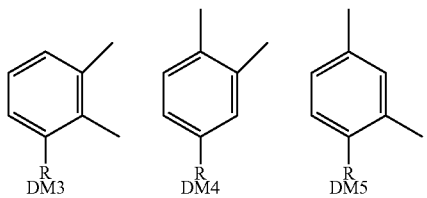
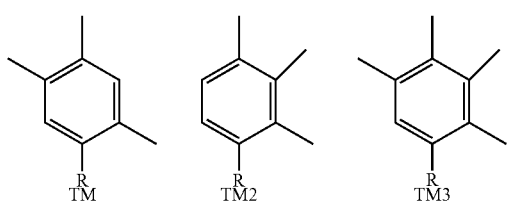
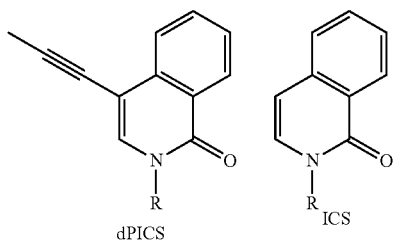
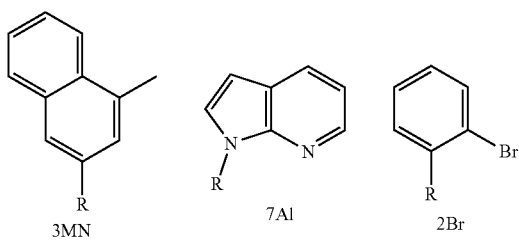
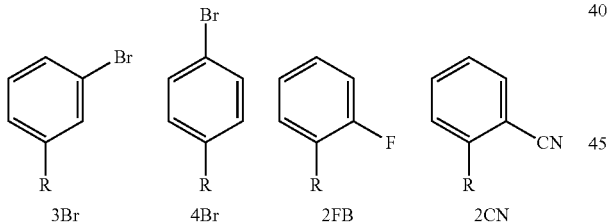
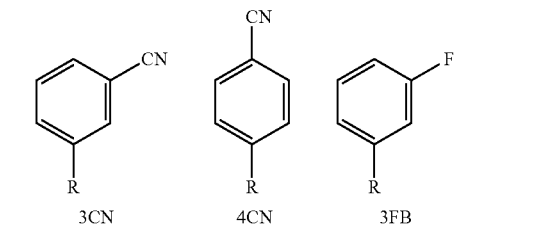
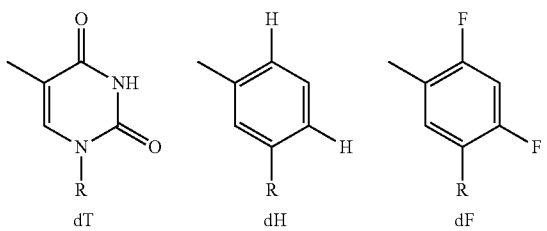
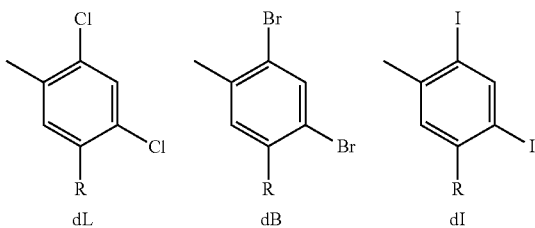
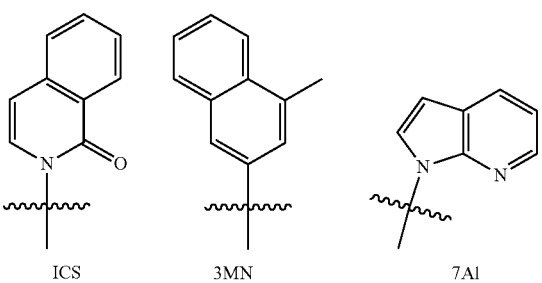
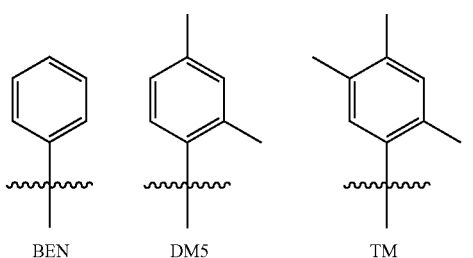
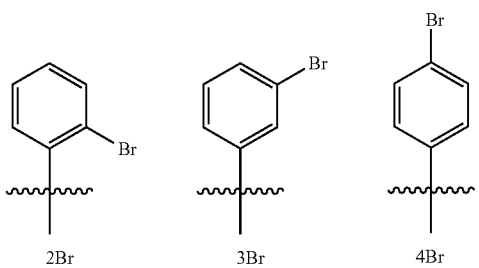
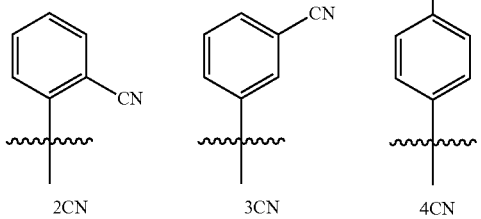
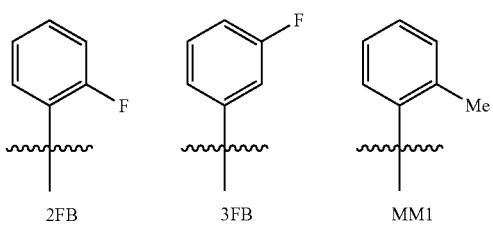

-continued
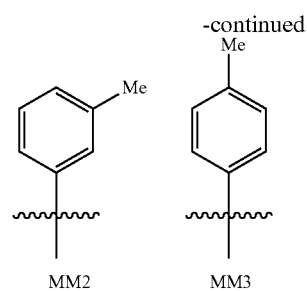
MM2  MM3
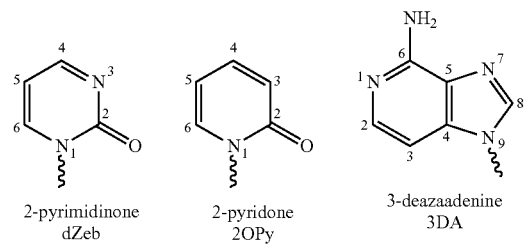
2-pyrimidinone dZeb  2-pyridone 2OPy  3-deazaadenine 3DA
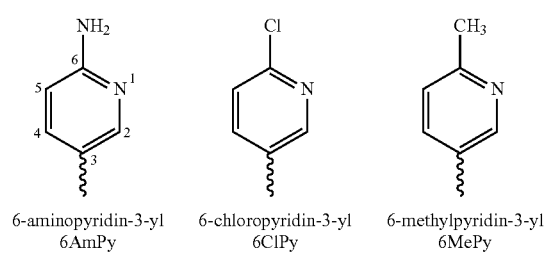
6-aminopyridin-3-yl 6AmPy  6-chloropyridin-3-yl 6ClPy  6-methylpyridin-3-yl 6MePy
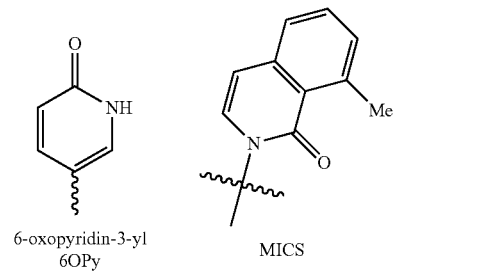
6-oxopyridin-3-yl 6OPy  MICS
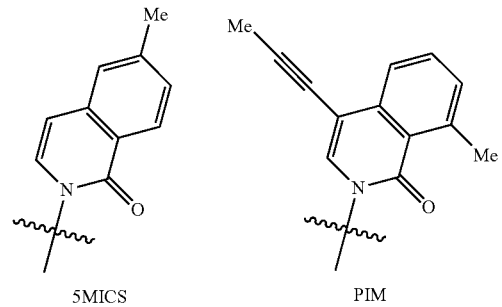
5MICS  PIM
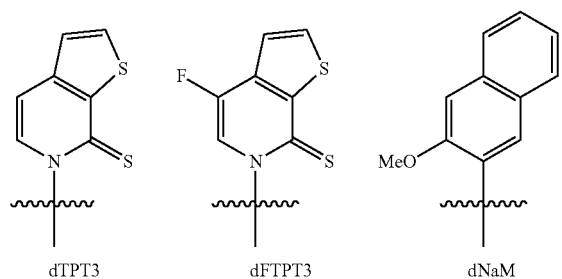
dTPT3  dFTPT3  dNaM
-continued
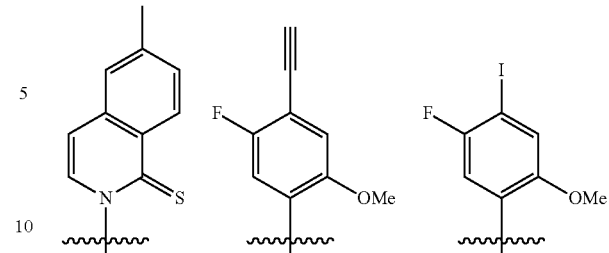
d5SICS  dFEMO  dFIMO
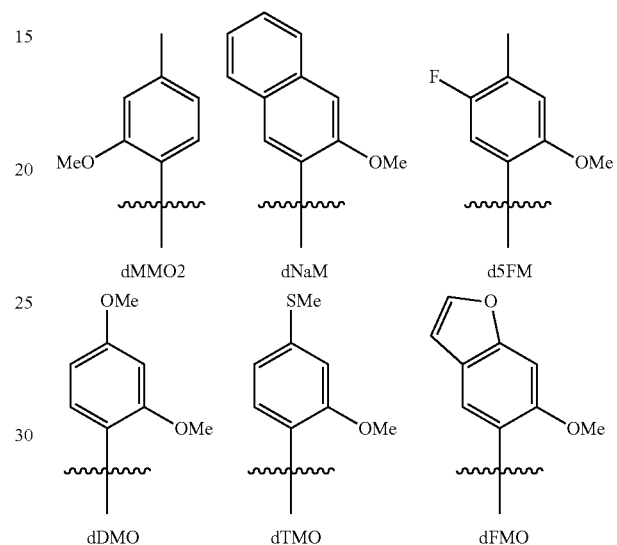
dMMO2  dNaM  d5FM
dDMO  dTMO  dFMO
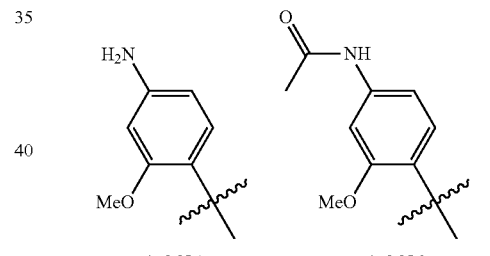
dAMO1  dAMO2
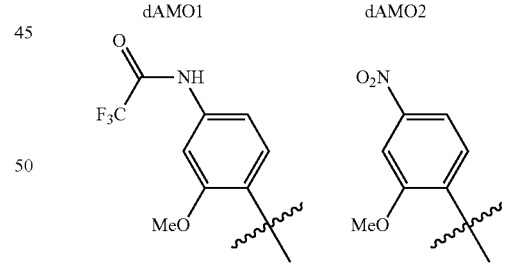
dAMO3  dNMO1
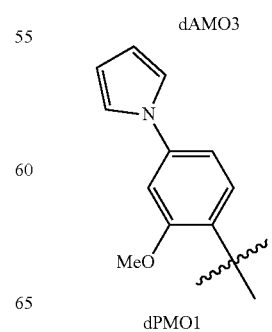
dPMO1

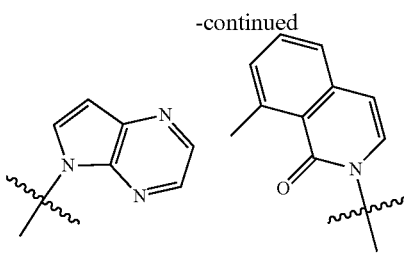

PP:MICS

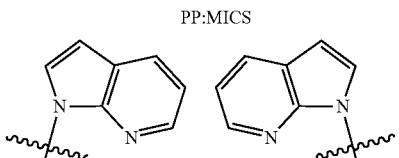

7AI:7AI

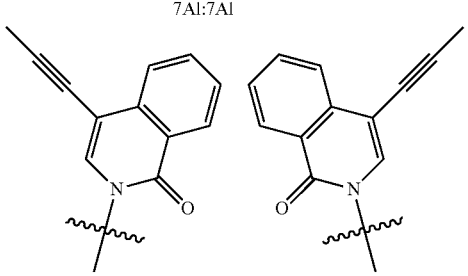

PICS:PICS

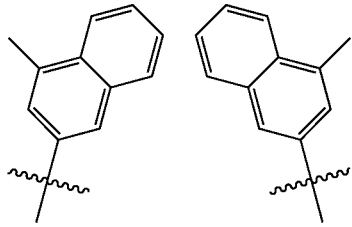

3MN:3MN

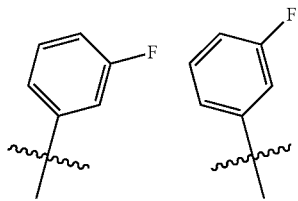

3FB:3FB

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-CH$_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., Synlett, 1997, 1287-1290). Unnatural nucleic acids can include 2'-substituted 5'-CH$_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group (SC(CH$_3$)$_3$) (and analogs thereof); a methyleneamino group (CH$_2$NH$_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or C(Ri)(R$_2$) (R=H, C$_1$-C$_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$, alkyl or C$_2$ to C$_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$ONH$_2$, and —O(CH$_2$)$_n$ON[(CH$_2$)$_n$CH$_3$)]$_2$, where n and m are from 1 to about 10.

Other modifications at the 2' position include but are not limited to: C$_1$ to C$_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—(C$_1$-C$_{10}$ alkyl), OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845); 4'-C(CH$_3$)(CH$_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N*-dimethylhydrazine (—CH$_2$—N(CH$_3$)—N(CH$_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Nucleic Acid Base Pairing Properties

In some embodiments, an unnatural nucleic acid forms a base pair with another nucleic acid. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleotide triphosphates that can base pair when incorporated into nucleic acids include a triphosphate of d5SICS (d5SICSTP) and a triphosphate of dNaM (dNaMTP). Such unnatural nucleotides can have a ribose or deoxyribose sugar moiety. In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural nucleic acid is an unnatural nucleic acid that can form a UBP, but does not substantially form a base pair with each of the four natural nucleic acids. In some embodiments, a stably integrated unnatural nucleic acid is an unnatural nucleic acid that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo includes, but is not limited to, 5SICS, d5SICS, NAM, dNaM, dTPT$_3$, and combinations thereof. In some embodiments, unnatural nucleotides include:

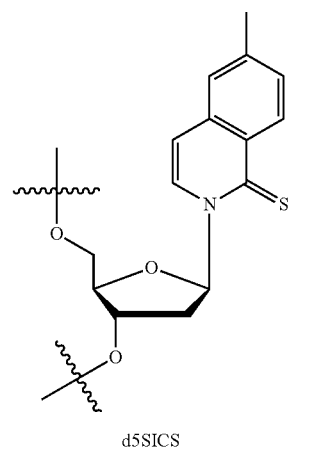

d5SICS

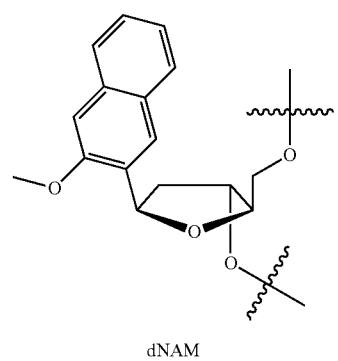

dNAM

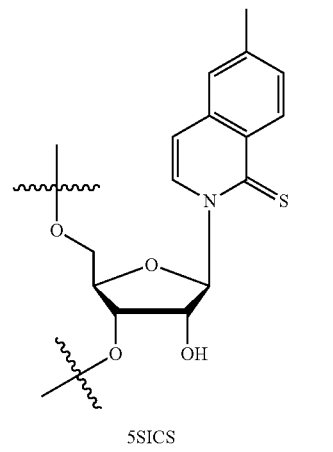

5SICS

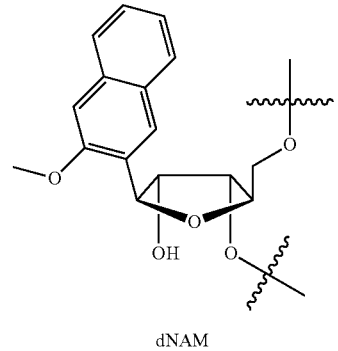

dNAM

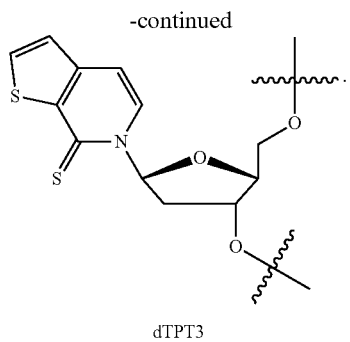

dTPT3

Engineered Organism

In some embodiments, methods and plasmids disclosed herein is further used to generate engineered organism, e.g. an organism that incorporates and replicates an unnatural nucleotide or an unnatural nucleic acid base pair (UBP) with improved UBP retention and also transcribes and translates the nucleic acid containing the unnatural nucleotide or unnatural nucleic acid base pair into a protein containing an unnatural amino acid residue. In some instances, the organism is a semi-synthetic organism (SSO). In some instances, the SSO is a cell.

In some instances, the cell employed is genetically transformed with an expression cassette encoding a heterologous protein, e.g., a nucleoside triphosphate transporter capable of transporting unnatural nucleotide triphosphates into the cell, a modified transposition-associated protein to increase stability of the nucleotide triphosphate transporter, a CRISPR/Cas9 system to remove modifications at the unnatural nucleotide triphosphate positions, and/or a polymerase with high fidelity for an unnatural nucleic acid, so that the unnatural nucleotides are incorporated into cellular nucleic acids and e.g., form unnatural base pairs under in vivo conditions. In some instances, cells further comprise enhanced activity for unnatural nucleic acid uptake. In some cases, cells further comprise enhanced activity for unnatural nucleic acid import. In some cases, cells further comprise enhanced polymerase activity for unnatural nucleic acids.

In some embodiments, Cas9 and sgRNA are encoded on separate plasmids. In some instances, Cas9 and sgRNA are encoded on the same plasmid. In some cases, the nucleic acid molecule encoding Cas9, sgRNA, or a nucleic acid molecule comprising an unnatural nucleotide are located on one or more plasmids. In some instances, Cas9 is encoded on a first plasmid and the sgRNA and the nucleic acid molecule comprising an unnatural nucleotide are encoded on a second plasmid. In some instances, Cas9, sgRNA, and the nucleic acid molecule comprising an unnatural nucleotide are encoded on the same plasmid. In some instances, the nucleic acid molecule comprises two or more unnatural nucleotides.

In some instances, a first plasmid encoding Cas9 and sgRNA and a second plasmid encoding a nucleic acid molecule comprising an unnatural nucleotide are introduced into an engineered microorganism. In some instances, a first plasmid encoding Cas9 and a second plasmid encoding sgRNA and a nucleic acid molecule comprising an unnatural nucleotide are introduced into an engineered microorganism. In some instances, a plasmid encoding Cas9, sgRNA and a nucleic acid molecule comprising an unnatural nucleotide is introduced into an engineered microorganism. In some instances, the nucleic acid molecule comprises two or more unnatural nucleotides.

In some embodiments, a living cell is generated that incorporates within its nucleic acids at least one unnatural nucleotide and/or at least one unnatural base pair (UBP). In some instances, the unnatural base pair includes a pair of unnatural mutually base-pairing nucleotides capable of forming the unnatural base pair under in vivo conditions, when the unnatural mutually base-pairing nucleotides, as their respective triphosphates, are taken up into the cell by action of a nucleotide triphosphate transporter. The cell can be genetically transformed by an expression cassette encoding a nucleotide triphosphate transporter so that the nucleotide triphosphate transporter is expressed and is available to transport the unnatural nucleotides into the cell. The cell can be genetically transformed by an expression cassette encoding a polymerase so that the polymerase is expressed and is available to incorporate unnatural nucleotides into the cell's nucleic acids. The cell can be a prokaryotic or eukaryotic cell, and the pair of unnatural mutually base-pairing nucleotides, as their respective triphosphates, can be a triphosphate of d5SICS (d5SICSTP) and a triphosphate of dNaM (dNaMTP).

In some embodiments, cells are genetically transformed cells with a nucleic acid, e.g., an expression cassette encoding a nucleotide triphosphate transporter capable of transporting such unnatural nucleotides into the cell. A cell can comprise a heterologous nucleotide triphosphate transporter, where the heterologous nucleotide triphosphate transporter can transport natural and unnatural nucleotide triphosphates into the cell. A cell can comprise a heterologous polymerase, where the heterologous polymerase has activity for an unnatural nucleic acid.

In some cases, a method described herein also include contacting a genetically transformed cell with the respective triphosphate forms unnatural nucleotides, in the presence of potassium phosphate and/or an inhibitor of phosphatases or nucleotidases. During or after such contact, the cell can be placed within a life-supporting medium suitable for growth and replication of the cell. The cell can be maintained in the life-supporting medium so that the respective triphosphate forms of unnatural nucleotides are incorporated into nucleic acids within the cells, and through at least one replication cycle of the cell. The pair of unnatural mutually base-pairing nucleotides as a respective triphosphate, can comprise a triphosphate of d5SICS (d5SICSTP) and a triphosphate of dNaM (dNaMTP), the cell can be E. coli, and the d5SICSTP and dNaMTP can be efficiently imported into E. coli by the transporter PtNTT2, wherein an E. coli polymerase, such as Pol I, can efficiently use the unnatural triphosphates to replicate DNA, thereby incorporating unnatural nucleotides and/or unnatural base pairs into cellular nucleic acids within the cellular environment.

By practice of a method of the invention, the person of ordinary skill can obtain a population of a living and propagating cells that has at least one unnatural nucleotide and/or at least one unnatural base pair (UBP) within at least one nucleic acid maintained within at least some of the individual cells, wherein the at least one nucleic acid is stably propagated within the cell, and wherein the cell expresses a nucleotide triphosphate transporter suitable for providing cellular uptake of triphosphate forms of one or more unnatural nucleotides when contacted with (e.g., grown in the presence of) the unnatural nucleotide(s) in a life-supporting medium suitable for growth and replication of the organism.

After transport into the cell by the nucleotide triphosphate transporter, the unnatural base-pairing nucleotides are incorporated into nucleic acids within the cell by cellular machinery, e.g., the cell's own DNA and/or RNA polymerases, a heterologous polymerase, or a polymerase that has been evolved using directed evolution (Chen T, Romesberg F E, FEBS Lett. 2014 Jan. 21; 588(2):219-29; Betz K et al., J Am Chem Soc. 2013 Dec. 11; 135(49):18637-43). The unnatural nucleotides can be incorporated into cellular nucleic acids such as genomic DNA, genomic RNA, mRNA, structural RNA, microRNA, and autonomously replicating nucleic acids (e.g., plasmids, viruses, or vectors).

In some cases, genetically engineered cells are generated by introduction of nucleic acids, e.g., heterologous nucleic acids, into cells. Any cell described herein can be a host cell and can comprise an expression vector. In one embodiment, the host cell is a prokaryotic cell. In another embodiment, the host cell is E. coli. In some embodiments, a cell comprises one or more heterologous polynucleotides. Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595, 899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some instances, genetic transformation is obtained using direct transfer of an expression cassette, in but not limited to, plasmids, viral vectors, viral nucleic acids, phage nucleic acids, phages, cosmids, and artificial chromosomes, or via transfer of genetic material in cells or carriers such as cationic liposomes. Such methods are available in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

For example, a nucleotide triphosphate transporter or polymerase nucleic acid molecule, expression cassette and/ or vector can be introduced to a cell by any method including, but not limited to, calcium-mediated transformation, electroporation, microinjection, lipofection, particle bombardment and the like.

In some cases, a cell comprises unnatural nucleotide triphosphates incorporated into one or more nucleic acids within the cell. For example, the cell can be a living cell capable of incorporating at least one unnatural nucleotide within DNA or RNA maintained within the cell. The cell can also incorporate at least one unnatural base pair (UBP) comprising a pair of unnatural mutually base-pairing nucleotides into nucleic acids within the cell under in vivo conditions, wherein the unnatural mutually base-pairing nucleotides, e.g., their respective triphosphates, are taken up into the cell by action of a nucleotide triphosphate transporter, the gene for which is present (e.g., was introduced) into the cell by genetic transformation. For example, upon incorporation into the nucleic acid maintained within s cell, d5SICS and dNaM can form a stable unnatural base pair that can be stably propagated by the DNA replication machinery of an organism, e.g., when grown in a life-supporting medium comprising d5SICS and dNaM.

In some cases, cells are capable of replicating an unnatural nucleic acid. Such methods can include genetically transforming the cell with an expression cassette encoding a nucleotide triphosphate transporter capable of transporting into the cell, as a respective triphosphate, one or more unnatural nucleotides under in vivo conditions. Alternatively, a cell can be employed that has previously been genetically transformed with an expression cassette that can express an encoded nucleotide triphosphate transporter. The method can also include contacting or exposing the genetically transformed cell to potassium phosphate and the respective triphosphate forms of at least one unnatural nucleotide (for example, two mutually base-pairing nucleotides capable of forming the unnatural base pair (UBP)) in a life-supporting medium suitable for growth and replication of the cell, and maintaining the transformed cell in the life-supporting medium in the presence of the respective triphosphate forms of at least one unnatural nucleotide (for example, two mutually base-pairing nucleotides capable of forming the unnatural base pair (UBP)) under in vivo conditions, through at least one replication cycle of the cell.

In some embodiments, a cell comprises a stably incorporated unnatural nucleic acid. Some embodiments comprise a cell (e.g., as E. coli) that stably incorporates nucleotides other than A, G, T, and C within nucleic acids maintained within the cell. For example, the nucleotides other than A, G, T, and C can be d5SICS, dNaM, and dTPT3, which upon incorporation into nucleic acids of the cell, can form a stable unnatural base pair within the nucleic acids. In one aspect, unnatural nucleotides and unnatural base pairs can be stably propagated by the replication apparatus of the organism, when an organism transformed with the gene for the triphosphate transporter, is grown in a life-supporting medium that includes potassium phosphate and the triphosphate forms of d5SICS, dNaM, and dTPT3.

In some cases, a cell comprises an expanded genetic alphabet. A cell can comprise a stably incorporated unnatural nucleic acid. In some embodiments, a cell with an expanded genetic alphabet comprises an unnatural nucleic acid that can form a base pair (bp) with another nucleic acid, e.g., a natural or unnatural nucleic acid. In some embodiments, a cell with an expanded genetic alphabet comprises an unnatural nucleic acid that is hydrogen bonded to another nucleic acid. In some embodiments, a cell with an expanded genetic alphabet comprises an unnatural nucleic acid that is not hydrogen bonded to another nucleic acid to which it is base paired. In some embodiments, a cell with an expanded genetic alphabet comprises an unnatural nucleic acid that base pairs to another nucleic acid via hydrophobic interactions. In some embodiments, a cell with an expanded genetic alphabet comprises an unnatural nucleic acid that base pairs to another nucleic acid via non-hydrogen bonding interactions. A cell with an expanded genetic alphabet can be a cell that can copy a homologous nucleic acid to form a nucleic acid comprising an unnatural nucleic acid. A cell with an expanded genetic alphabet can be a cell comprising an unnatural nucleic acid base paired with another unnatural nucleic acid (unnatural nucleic acid base pair (UBP)).

In some embodiments, cells form unnatural DNA base pairs (UBPs) from the imported unnatural nucleotides under in vivo conditions. In some embodiments potassium phosphate and/or inhibitors of phosphatase and/or nucleotidase activities can facilitate transport of unnatural nucleic acids. The methods include use of a cell that expresses a heterologous nucleotide triphosphate transporter. When such a cell is contacted with one or more nucleotide triphosphates, the nucleotide triphosphates are transported into the cell. The cell can be in the presence of potassium phosphate and/or inhibitors of phosphatase and nucleotidase. Unnatural nucleotide triphosphates can be incorporated into nucleic acids within the cell by the cell's natural machinery and, for example, can mutually base-pair to form unnatural base pairs within the nucleic acids of the cell.

In some embodiments, a UBP can be incorporated into a cell or population of cells when exposed to unnatural triphosphates. In some embodiments a UBP can be incorporated into a cell or population of cells when substantially consistently exposed to unnatural triphosphates. In some embodiments, replication of a UBP does not result in a substantially reduced growth rate. In some embodiments, replication expression of a heterologous protein, e.g., a nucleotide triphosphate transport does not result in a substantially reduced growth rate.

In some embodiments, induction of expression of a heterologous gene, e.g., an NTT, in a cell can result in slower cell growth and increased unnatural nucleic acid uptake compared to the growth and uptake of a cell without induction of expression of the heterologous gene. In some embodiments, induction of expression of a heterologous gene, e.g., an NTT, in a cell can result in increased cell growth and increased unnatural nucleic acid uptake compared to the growth and uptake of a cell without induction of expression of the heterologous gene.

In some embodiments, a UBP is incorporated during a log growth phase. In some embodiments, a UBP is incorporated during a non-log growth phase. In some embodiments, a UBP is incorporated during a substantially linear growth phase. In some embodiments a UBP is stably incorporated into a cell or population of cells after growth for a time period. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP can be stably incorporated into a cell or population of cells after growth for at least about 1, 2, 3, 4, 5, 6, 7, 8, 9, 10, 11, or 12 months of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments, a cell further utilizes a polymerase described herein to generate a mutant mRNA which contains a mutant codon that comprises one or more unnatural nucleic acid base. In some instances, a cell further utilizes a polymerase disclosed herein to generate a mutant tRNA which contains a mutant anticodon that comprises one or more unnatural nucleic acid base. In some instances, the mutant anticodon represents an unnatural amino acid. In some instances, the anticodon of the mutant tRNA pairs with the codon of the mutant mRNA during translation to synthesis a protein that contains an unnatural amino acid.

As used herein, an amino acid residue can refer to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" can refer to a molecule containing both an amino group and a carboxyl group bound to a carbon which is designated the α-carbon.

The term "β-amino acid" can refer to a molecule containing both an amino group and a carboxyl group in a β configuration.

"Naturally occurring amino acid" can refer to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Gin | E | polar | negative | −3.5 |
| Glutamine | Gin | Q | polar | neutral | −3.5 |
| Glycine | Gly | G | nonpolar | neutral | −0.4 |
| Histidine | His | H | polar | positive(10%) neutral(90%) | −3.2 |
| Isoleucine | He | I | nonpolar | neutral | 4.5 |
| Leucine | Len | L | nonpolar | neutral | 3.8 |
| Ly sine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" can be glycine, alanine, proline, and analogs thereof. "Large hydrophobic amino acids" can be valine, leucine, isoleucine, phenylalanine, methionine, tryptophan, and analogs thereof "Polar amino acids" can be serine, threonine, asparagine, glutamine, cysteine, tyrosine, and analogs thereof "Charged amino acids" can be lysine, arginine, histidine, aspartate, glutamate, and analogs thereof.

An "amino acid analog" can be a molecule which is structurally similar to an amino acid and which can be substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

A "non-natural amino acid" can be an amino acid which is not one of the twenty amino acids commonly found in peptides synthesized in nature, and known by the one letter abbreviations A, R, N, C, D, Q, E, G, H, I, L, K, M, F, P, S, T, W, Y and V.

Amino acid analogs can include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs can include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH·dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH·dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH·dicyclohexylammonium salt; cyclopentyl-Gly-OH·dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine·dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene) ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid;

(N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs can include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys (N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)$_2$-OH (symmetrical); Lys(ivDde)-OH; Lys(Me)$_2$-OH·HCl; Lys (Me3)-OH chloride; Nω-nitro-D-arginine; and Nω-nitro-L-arginine.

Amino acid analogs can include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs can include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-amino-ethyl)-L-cysteine, seleno-L-cystine, cystathionine, Cys (StBu)-OH, and acetamidomethyl-D-penicillamine.

Amino acid analogs can include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl) amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs can include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs can include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs can include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3, 4-tetrahydro-norharman-3-carboxylic acid; 5-methoxy-2-methyl-tryptophan; and 6-chloro-L-tryptophan.

Amino acid analogs can be racemic. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some embodiments, an unnatural amino acid is an unnatural amino acid described in Liu C. C., Schultz, P. G. Annu. Rev. Biochem. 2010, 79, 413. In some embodiments, an unnatural amino acid comprises N6(2-azidoethoxy)-carbonyl-L-lysine.

Cell Types

In some embodiments, many types of cells/microorganisms are used, e.g., for transforming or genetically engineering. In some embodiments, a cell is a prokaryotic or eukaryotic cell. In some cases, the cell is a microorganism such as a bacterial cell, fungal cell, yeast, or unicellular protozoan. In other cases, the cell is a eukaryotic cell, such as a cultured animal, plant, or human cell. In additional cases, the cell is present in an organism such as a plant or animal.

In some embodiments, an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is a yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon,* or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus var. diffluens, Cryptococcus laurentii, Cryptococcus neofomans, Debaryomyces hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii, Lipomyces lipoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica,* or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et. al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental strains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* bacteria, *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea hyssopoides, Cuphea ignea, Cuphea ingrata, Cuphea jorullensis, Cuphea lanceolata, Cuphea linarioides, Cuphea llavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea splendida* var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii, Cuphea lanceolata*).

Microorganisms or cells used as host organisms or source for a heterologous polynucleotide are commercially available. Microorganisms and cells described herein, and other suitable microorganisms and cells are available, for example, from Invitrogen Corporation, (Carlsbad, CA), American Type Culture Collection (Manassas, Virginia), and Agricultural Research Culture Collection (NRRL; Peoria, Illinois). Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Polymerase

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

In some instances, disclosed herein includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3 to 5' exonuclease proofreading activity or where a 3 to 5' exonuclease proofreading activity has been disabled, e.g. through mutation. Examples of DNA polymerases include polA, polB (see e.g. Parrel & Loeb, Nature Struc Biol 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In some embodiments, polymerases are characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

In some embodiments, polymerases are characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of $(k_{cat}/K_m)$ for the natural and unnatural nucleic acid and $(k_{cat}/K_m)$ for the incorrect natural and unnatural nucleic acid; where $k_{cat}$ and $K_m$ are Michaelis-Menten parameters in steady state enzyme kinetics (Fersht, A. R. (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1\times10^6$, with or without a proofreading activity.

In some embodiments, polymerases from native sources or variants thereof are screened using an assay that detects incorporation of an unnatural nucleic acid having a particular structure. In one example, polymerases can be screened for the ability to incorporate an unnatural nucleic acid or UBP; e.g., d5SICSTP, dNaMTP, or d5SICSTP-dNaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, GI, Cp-1, PRD1, PZE, SF5, Cp-5, Cp-7, PR4, PR5, PR722, or L17 polymerase.

Modified polymerases of the compositions described can optionally be modified and/or recombinant prokaryotic DNA polymerase, e.g., DNA polymerase II (Pol II), DNA polymerase III (Pol III), DNA polymerase IV (Pol IV), DNA polymerase V (Pol V). In some embodiments, the modified polymerases comprise polymerases that mediate DNA synthesis across non-instructional damaged nucleotides. In some embodiments, the genes encoding Pol I, Pol II (polB), PolI IV (dinB), and/or Pol V (umuCD) are constitutively expressed, or overexpressed, in the engineered cell, or SSO. In some embodiments, an increase in expression or overexpression of Pol II contributes to an increased retention of unnatural base pairs (UBPs) in an engineered cell, or SSO.

Nucleic acid polymerases generally useful in the invention include DNA polymerases, RNA polymerases, reverse transcriptases, and mutant or altered forms thereof. DNA polymerases and their properties are described in detail in, among other places, DNA Replication $2^{nd}$ edition, Kornberg and Baker, W. H. Freeman, New York, N. Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al, 1991, Polynucleotides Res, 19: 4193, New England Biolabs), 9° Nm™ DNA polymerase (New England Biolabs), Stoffel fragment, Thermo Sequenase© (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al, 1976, J. Bacteriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *Thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *Thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al, 1981, J Biol. Chem. 256:3112), and archaeal DP11/DP2 DNA polymerase II (Cann et al, 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3' exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al, CRC Crit Rev Biochem. 3:289-347(1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase Gardner et al. (2004) "Comparative Kinetics of Nucleotide Analog Incorporation by Vent DNA Polymerase (J. Biol. Chem., 279(12), 11834-11842; Gardner and Jack "Determinants of nucleotide sugar recognition in an archaeon DNA polymerase" Nucleic Acids Research, 27(12) 2545-2553.) Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

In some embodiments, the polymerase comprises 029, B103, GA-1, PZA, 015, BS32, M2Y, Nf, GI, Cp-1, PRD1, PZE, SF5, Cp-5, Cp-7, PR4, PR5, PR722, L17, ThermoSequenase®, 9° Nm™, Terminator™ DNA polymerase, Tne, Tma, Tfl, Tth, Tli, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some embodiments, the polymerase is DNA polymerase 1-Klenow fragment, Vent polymerase, Phusion® DNA polymerase, KOD DNA polymerase, Taq polymerase, T7 DNA polymerase, T7 RNA polymerase, Terminator™ DNA polymerase, POLB polymerase, SP6 RNA polymerase, *E. coli* DNA polymerase I, *E. coli* DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Nucleotide Transporter

Nucleotide transporters (NTs) are a group of membrane transport proteins that facilitate nucleoside substrates across cell membranes and vesicles. In some embodiments, there are two types of nucleoside transporters, concentrative nucleoside transporters and equilibrative nucleoside transporters. In some instances, NTs also encompass the organic anion transporters (OAT) and the organic cation transporters (OCT). In some instances, nucleotide transporter is a nucleoside triphosphate transporter.

In some embodiments, a nucleotide triphosphate transporter (NTT) is from bacteria, plant, or algae. In some embodiments, a nucleotide nucleoside triphosphate transporter is TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*).

In some embodiments, NTT is CNT1, CNT2, CNT3, ENT1, ENT2, OAT1, OAT3, or OCT1.

In some embodiments, NTT imports unnatural nucleic acids into an organism, e.g. a cell. In some embodiments, NTTs can be modified such that the nucleotide binding site of the NTT is modified to reduce steric entry inhibition of the unnatural nucleic acid into the nucleotide biding site. In some embodiments, NTTs can be modified to provide increased interaction with one or more unnatural features of the unnatural nucleic acids. Such NTTs can be expressed or engineered in cells for stably importing a UBP into the cells. Accordingly, the invention includes compositions that include a heterologous or recombinant NTT and methods of use thereof.

NTTs can be modified using methods pertaining to protein engineering. For example, molecular modeling can be carried out based on crystal structures to identify the locations of the NTTs where mutations can be made to modify a target activity or binding site. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of NTTs can be used in a method or composition set forth herein including, for example, protein-based enzymes isolated from biological systems and functional variants thereof. Reference to a particular NTT, such as those exemplified below, will be understood to include functional variants thereof unless indicated otherwise. In some embodiments, a NTT is a wild type NTT. In some embodiments, a NTT is a modified, or mutant, NTT.

NTTs, with features for improving entry of unnatural nucleic acids into cells and for coordinating with unnatural nucleotides in the nucleotide biding region, can also be used. In some embodiments, a modified NTT has a modified nucleotide binding site. In some embodiments, a modified or wild type NTT has a relaxed specificity for an unnatural nucleic acid.

In some embodiments, a modified NTT has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid. In some embodiments, a modified or wild type NTT has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified sugar. In some embodiments, a modified or wild type NTT has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward a nucleic acid comprising a triphosphate and/or the unnatural nucleic acid without the triphosphate. For example, a modified or wild type NTT can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid with a diphosphate or monophosphate, or no phosphate, or a combination thereof.

In some embodiments, a modified or wild type NTT has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid.

NTTs can be characterized according to their rate of dissociation from nucleic acids. In some embodiments a NTT has a relatively low dissociation rate for one or more natural and unnatural nucleic acids. In some embodiments a NTT has a relatively high dissociation rate for one or more natural and unnatural nucleic acids. The dissociation rate is an activity of a NTT that can be adjusted to tune reaction rates in methods set forth herein.

NTTs from native sources or variants thereof can be screened using an assay that detects importation of an unnatural nucleic acid having a particular structure. In one example, NTTs can be screened for the ability to import an unnatural nucleic acid or UBP; e.g., d5SICSTP, dNaMTP, or d5SICSTP-dNaMTP UBP. A NTT, e.g., a heterologous NTT, can be used that displays a modified property for the unnatural nucleic acid as compared to the wild-type NTT. For example, the modified property can be, e.g., $K_m$, $k_{cat}$, $V_{max}$, NTT importation in the presence of an unnatural nucleic acid (or of a naturally occurring nucleotide), average template read-length by a cell with the NTT in the presence of an unnatural nucleic acid, specificity of the NTT for an unnatural nucleic acid, rate of binding of an unnatural nucleic acid, or rate of product release, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the NTT optionally has an increased rate of binding of an unnatural nucleic acid, an increased rate of product release, and/or an increased cell importation rate, as compared to a wild-type NTT.

At the same time, a NTT can import natural nucleic acids, e.g., A, C, G, and T, into cell. For example, a NTT optionally displays a specific importation activity for a natural nucleic acid that is at least about 5% as high (e.g., 5%, 10%, 25%, 50%, 75%, 100% or higher), as a corresponding wild-type NTT. Optionally, the NTT displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type NTT.

NTTs used herein that can have the ability to import an unnatural nucleic acid of a particular structure can also be produced using a directed evolution approach. A nucleic acid synthesis assay can be used to screen for NTT variants having specificity for any of a variety of unnatural nucleic acids. For example, NTT variants can be screened for the ability to import an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant NTT variant. In some embodiments, such an assay is an in vivo assay, e.g., expressing a NTT variant in a cell. Such directed evolution techniques can be used to screen variants of any suitable NTT for activity toward any of the unnatural nucleic acids set forth herein.

Nucleic Acid Reagents & Tools

A nucleic acid reagent for use with a method, cell, or engineered microorganism described herein comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleic acid reagent or other reagent described herein is isolated or purified.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A nucleic acid or nucleic acid reagent can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

As noted above, nucleic acid reagents may also comprise one or more 5' UTR's, and one or more 3'UTR's. For example, expression vectors used in eukaryotic host cells (e.g., yeast, fungi, insect, plant, animal, human or nucleated cells) and prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR is used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells or eukaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic and eukaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Non-limiting examples of eukaryotic promoters that can be used include constitutive promoters, e.g., viral promoters such as CMV, SV40 and RSV promoters, as well as regulatable promoters, e.g., an inducible or repressible promoter such as a let promoter, a hsp70 promoter, and a synthetic promoter regulated by CRE. Vectors for bacterial expression include pGEX-5X-3, and for eukaryotic expression include pCIneo-CMV. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

Cloning

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, BsaI, Bsm I, BsmBI, BssH II, BstE II, Cfo I, Cla I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein k Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993)).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another function efficiently in another organism (e.g., a eukaryote, like yeast for example). In some embodiments, an ORI may function efficiently in one species (e.g., S. cerevisiae, for example) and another ORI may function efficiently in a different species (e.g., S. pombe, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the E. coli lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern et al., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985)).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise nonfunctional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683, 195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, a kit includes a suitable packaging material to house the contents of the kit. In some cases, the packaging material is constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

In some embodiments, a kit is provided that is useful for stably incorporating an unnatural nucleic acid into a cellular nucleic acid, e.g., using the methods provided by the present invention for preparing genetically engineered cells. In one embodiment, a kit described herein includes a genetically engineered cell and one or more unnatural nucleic acids. In another embodiment, a kit described herein includes an isolated and purified plasmid comprising a sequence selected from SEQ ID NOS 1-32.

In additional embodiments, the kit described herein provides a cell and a nucleic acid molecule containing a heterologous gene for introduction into the cell to thereby provide a genetically engineered cell, such as expression vectors comprising the nucleic acid of any of the embodiments hereinabove described in this paragraph.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

EXAMPLES

These examples are provided for illustrative purposes only and not to limit the scope of the claims provided herein.

Example 1: Determination of how Cells Retain or Lose the UBP in *E. coli*

Under steady-state conditions, DNA containing the dNaM-dTPT3 UBP was replicated in vitro with an efficiency approaching that of a fully natural counterpart; however, these rates are likely limited by product dissociation. In vivo replication is more processive, and correspondingly less likely to be limited by product dissociation. Therefore, replication of DNA containing the UBP in the SSO may be less efficient than that of fully natural DNA, and in turn, may cause replication forks to stall. Additionally, structural studies have indicated that the UBP adopts a Watson-Crick-like structure during triphosphate insertion, but once inserted, the UBP adopts a cross-strand intercalated structure that induces local helix distortions. Cells interpret both stalled replication forks and helix distortions as signs of DNA damage and initiate programs to repair or tolerate the offending nucleotides, which we suspected might contribute to UBP loss.

To determine how cells retain or lose the UBP, the effects of disabling these pathways was studied. Results indicate that neither nucleotide excision repair (NER) nor the SOS response contribute significantly to UBP retention or loss. Conversely, the normal replisome polymerase, DNA polymerase III (Pol III), Pol II, and methyl-directed mismatch repair (MMR), all contribute to UBP retention; while recombinational repair (RER) of replication forks that stall provides the major route to UBP loss. Next, the replisome of the SSO was reprogrammed to impart it with the ability to not only better retain the UBP on a plasmid, but also to stably harbor a UBP in its chromosome.

Nucleotide Excision Repair does not Contribute to UBP Retention or Loss

Figure 1B:
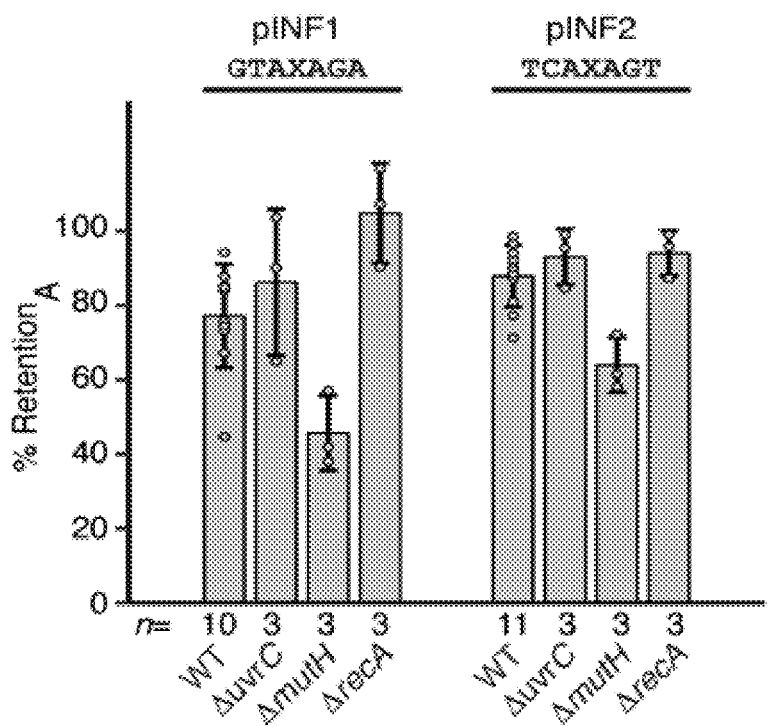

Generally, E. coli responds to DNA damage via direct damage reversal, base excision repair, NER, MMR, RER, and the SOS response. Neither direct damage reversal nor base excision repair is likely to contribute to UBP retention or loss, because these pathways rely on enzymes that recognize specific forms of DNA damage which are not likely to be mimicked by the UBP. In contrast, NER, MMR, RER, and the SOS response, are induced by less structure-specific signals. To begin to explore how cells manage to retain the UBP in their DNA, NER, which is mediated in a replication-independent manner by a complex of proteins that scan DNA for distortions resulting from bulky lesions that may be mimicked by the UBP, was studied. Contributions of NER to UBP retention or loss were explored by deleting uvrC, which encodes an essential component of NER, from the parental SSO (E. coli BL21(DE3)+pACS2 (FIG. 4)). Replication of DNA containing the dNaM-dTPT$_3$ UBP positioned in two different sequence contexts in plasmids pINF1 and pINF2 was unaffected by deletion of uvrC, indicating that NER makes no contribution to UBP retention or loss (FIG. 1B).

Methyl-Directed Mismatch Repair Increases UBP Retention

MMR was investigated next, which provides the critical first check of newly synthesized DNA as it emerges from a DNA polymerase during replication and is mediated by a complex of proteins that recognizes helix distortions caused by mismatched natural nucleotides. Upon detection of a mismatch, the MMR complex nicks the newly synthesized, unmethylated strand, which in turn leads to gap formation and subsequent resynthesis of the DNA. In contrast to NER, deactivation of MMR via deletion of mutH resulted in a reduction in UBP retention with both pINF1 and pINF2 (FIG. 1B). These results indicate that the helix distortions associated with the UBP are not sufficiently severe to activate MMR or that the unnatural nucleotides cannot be excised, but that the distortions caused by the pairing of an unnatural and a natural nucleotide are recognized and processed by MMR. Thus, MMR appears to effectively recognize the UBP as natural-like and selectively removes mispaired natural nucleotides, thereby supporting the stable expansion of the genetic alphabet.

Recombinational Repair Provides the Major Route to UBP Loss

Figure 1C:
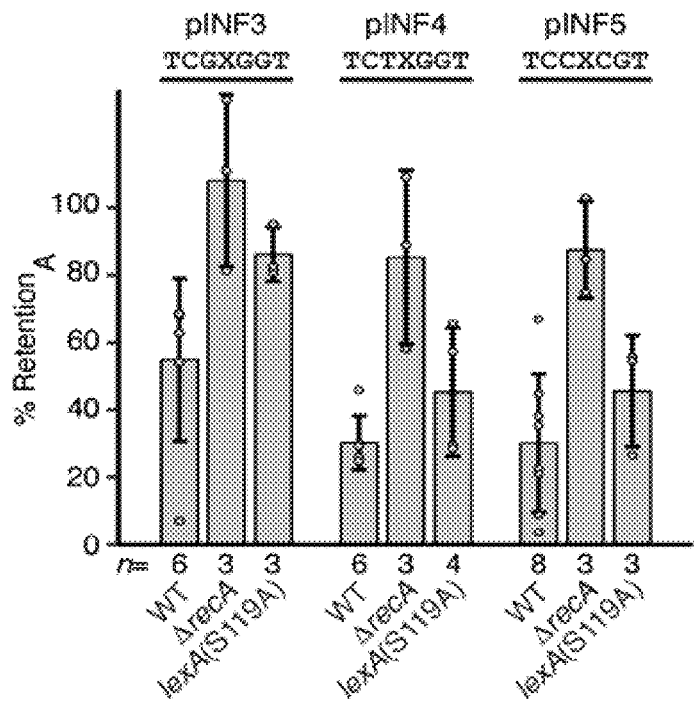

RER is mediated by RecA, which forms filaments on single-stranded DNA ahead of stalled replication forks, in turn, facilitating the formation of recombination intermediates and switching to a homologous template for continued DNA replication. The SOS response is induced when the same RecA filaments promote cleavage of the SOS repressor LexA, which leads to the derepression of a variety of genes involved in the tolerance and/or repair of the damaged DNA that caused the fork to stall. We explored the combined contribution of RER and the SOS response through the deletion of recA and observed a significant increase in UBP retention with pINF1 (FIG. 1B). To further explore the contribution of RecA, retention of the UBP in the more challenging sequences provided by pINF3, pINF4, and pINF5, was measured in the ΔrecA SSO (FIG. 1C). In these sequence contexts, the absence of recA resulted in a more dramatic increase in UBP retention.

To discern if recA deletion facilitates UBP retention by ablating RER or by preventing the induction of the SOS response, an SSO that is unable to induce the SOS response, but which is competent for RER (SSO lexA(S119A)) was examined (FIG. 1C). While selective suppression of the SOS response resulted in moderately increased UBP retention with pINF3, the increase was less than that observed with the ΔrecA SSO. With pINF4 and pINF5, selective SOS suppression resulted in only modest increases in UBP retention that were well below those observed with the recA SSO. These results demonstrate that the majority of UBP loss mediated by RecA occurs via RER and not via induction of the SOS response.

Pol II Contributes to the Replication of DNA Containing the UBP

Figure 1D:
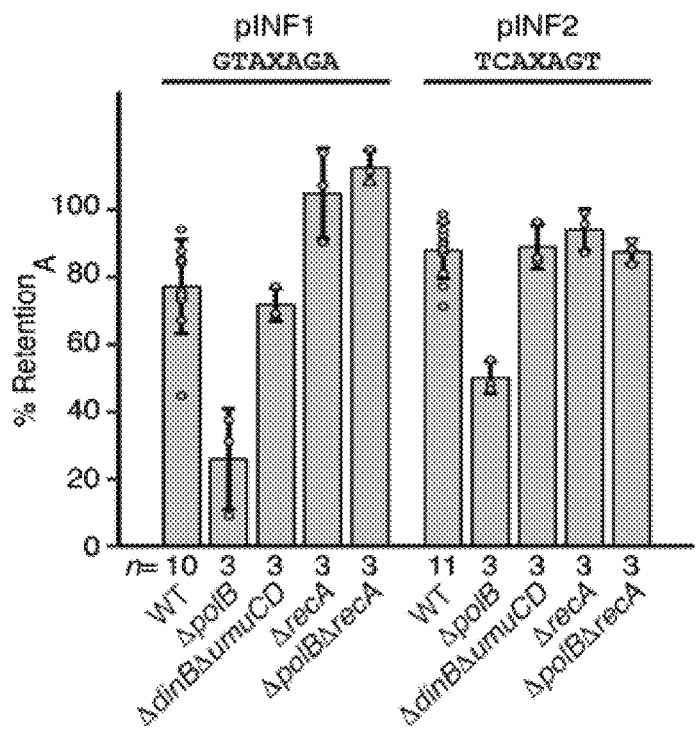

While the data suggests that much of UBP loss is mediated via RER, the marginal and sequence-specific increase in UBP retention with the lexA(S119A) SSO suggests that one or more SOS regulated proteins may also contribute. The contribution of the three SOS-regulated DNA polymerases, Pol II, Pol IV, and Pol V was investigated. Indeed, Pol IV and Pol V are "translesion" polymerases that are well known for their ability to mediate DNA synthesis across "non-instructional" damaged nucleotides. However, deletion of both dinB and umuCD (which encode Pol IV and the precursor of Pol V, respectively) did not impact UBP retention with either pINF1 or pINF2 (FIG. 1D). In contrast to the ΔdinBΔumuDC SSO, the deletion of polB (which encodes Pol II) resulted in a dramatic increase in UBP loss with both pINF1 and pINF2 (FIG. 1D). Overall, these data demonstrate that RER constitutes the major route to UBP loss and that Pol II provides an important route to UBP retention. While the production of Pol II is increased by the induction of SOS, the data suggests that its beneficial role is overwhelmed by the deleterious effects of the concomitantly induced RER.

Figure 1E:
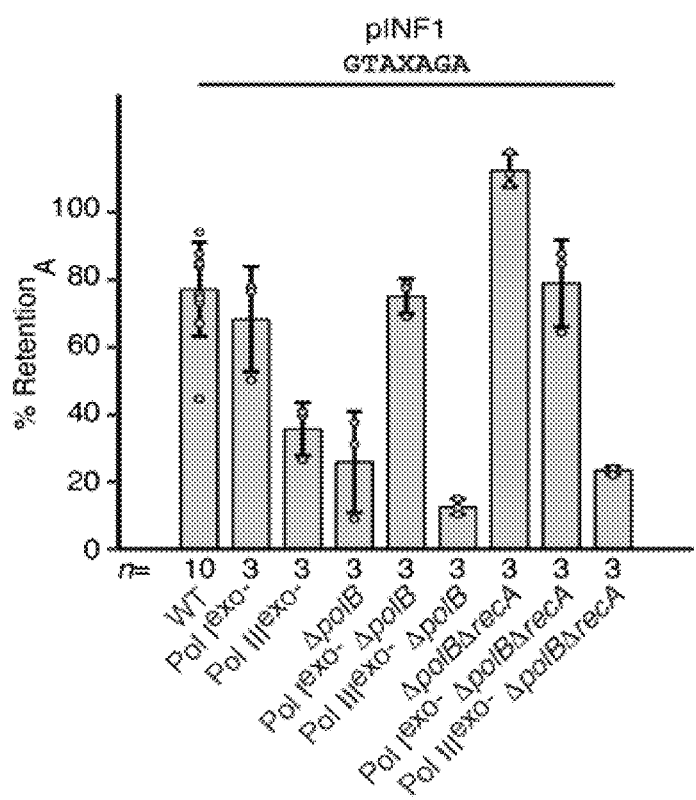

DNA Polymerases III Also Contributes to the Replication of DNA Containing the UBP The reduced but still detectable retention of the UBP in the ΔpolB SSO, along with the negligible effects of deleting the genes encoding Pol IV and Pol V, strongly suggest that one or both of the remaining DNA polymerases, Pol I and Pol III, must also contribute to retention of the UBP. To specifically examine whether Pol I or Pol III contribute to the replication of DNA containing the UBP, we constructed and characterized strains in which their 3'-5' exonuclease ("proofreading") activity was eliminated or impaired via mutation (Pol I$^{exo-}$ polA(D424A,K890R) and Pol III$^{exo-}$, dnaQ(D12N), respectively (FIG. 1E). While the deletion of Pol I exonuclease activity had no effect on UBP retention, the Pol III exonuclease deficient mutant showed a dramatic reduction in UBP retention. This data clearly indicates that in wild type cells, Pol III, but not Pol I, contributes to the replication of DNA containing the UBP.

To determine if any effects of the Pol I or Pol III mutations were masked by the activities of Pol II and/or RER, UBP retention was examined in the ΔpolB, or ΔpolBΔrecA SSO. Results indicate that the UBP was well retained with the ΔpolBΔrecA SSO, demonstrating that polymerases other than Pol II are capable of mediating high-level UBP retention in the absence of competition with RER-mediated loss (FIG. 1E). The Pol III exonuclease mutant again showed decreased UBP retention in both ΔpolB and ΔpolBΔrecA SSOs. However, in contrast to wild type cells, the deletion of Pol I exonuclease activity had significant and opposite effects with the ΔpolB and ΔpolBΔrecA SSO, in which retention increased and decreased, respectively. These data demonstrate that in addition to Pol II, Pol III contributes to the retention of the UBP, and in the absence of RER, Pol I does as well.

A model for the replication of DNA containing the UBP

Without wishing to be bound by any particular theory, the results described herein suggest the following model for replication of DNA containing the dNaM-dTPT3 UBP in the E. coli SSO. When the replisome with Pol III encounters an unnatural nucleotide during processive leading or lagging strand replication, Pol III incorporates either a natural or an unnatural nucleotide. If a natural nucleotide is incorporated, the rate of proofreading is competitive with, and perhaps more efficient than continued extension, and thus the natural nucleotide is commonly excised via the proofreading activity of Pol III. However, if a correct UBP is synthesized, more efficient extension prevents excision and the replisome continues synthesizing DNA. As it exits the polymerase, the nascent duplex is scanned by the MMR complex, which further increases UBP retention by preferentially eliminating any mispaired natural nucleotides that escaped proofreading.

Because extension of even a correct UBP is likely to be less efficient than natural synthesis, Pol III may also dissociate. The stalled fork, likely with the extending strand terminated immediately before the unnatural nucleotide in the template, is a now a substrate for RER, which reinitiates synthesis using a homologous natural sequence and thus provides the dominant mechanism for UBP loss. However, in competition with RecA-mediated RER, Pol II can rescue the stalled fork and reinitiate synthesis with high UBP retention, after which it presumably yields to Pol III and the reestablishment of a normal replication fork. The contribution of Pol I is more complex. In wild type cells, Pol I does not appear to contribute to the replication of DNA containing the UBP. In contrast, in the absence of Pol II and RecA, Pol I does contribute and correspondingly, the deletion of Pol I exonuclease activity results in decreased UBP retention. However, if the exonuclease activity is eliminated, Pol I can contribute if Pol II is eliminated, and in this case it increases retention by competing with RER.

It is accepted that Pol II has two putative roles: (1) in replication restart where Pol II rescues stalled forks after Pol III synthesizes a mispair that it cannot efficiently extend; and (2) Pol II is to compete with RER to fill in gaps created by NER as part of the cellular response to interstrand cross-linked DNA. Interestingly, the evoked role of Pol II in rescuing replication forks stalled at the UBP in competition with RER is strikingly similar to aspects of both of the putative natural roles. However, this effect on the replication of DNA containing the UBP is the most significant phenotype ever observed with its elimination.

Optimization of the SSO

Figure 4A:
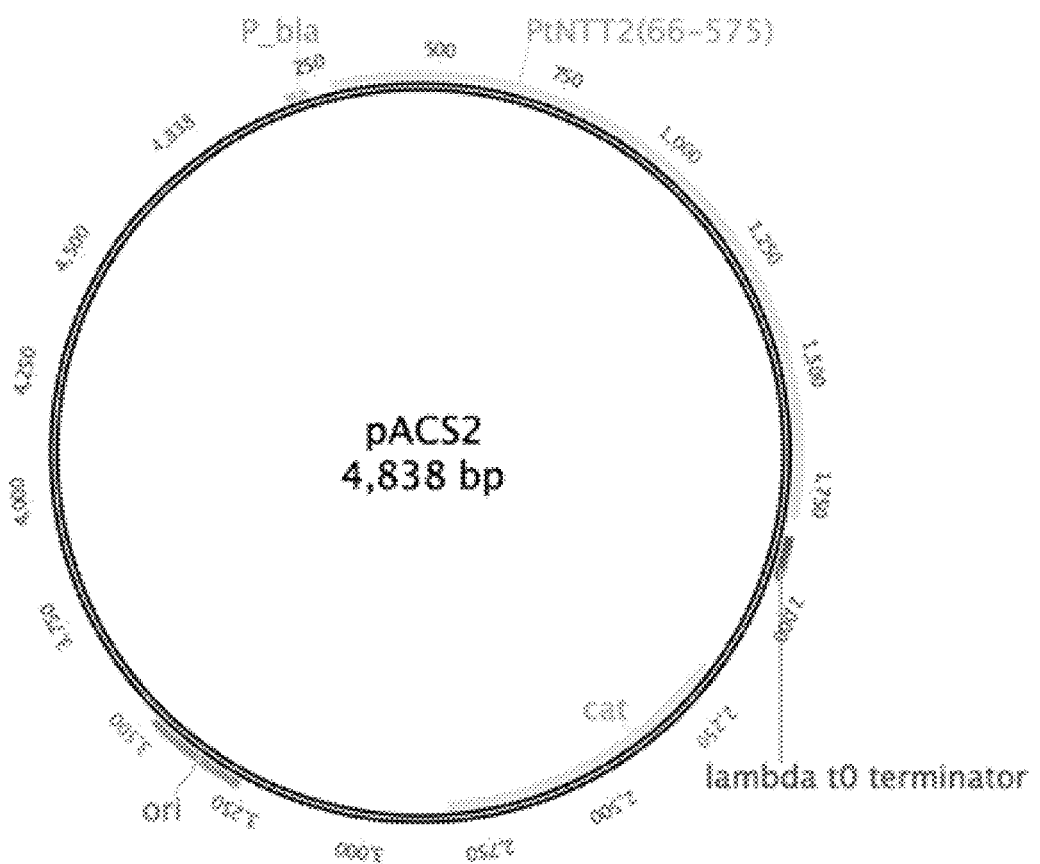
FIG. 4A-FIG. 4C exemplify PtNTT2 expression constructs. Expression constructs for PtNTT2(66-575) are shown.
Figure 4B:
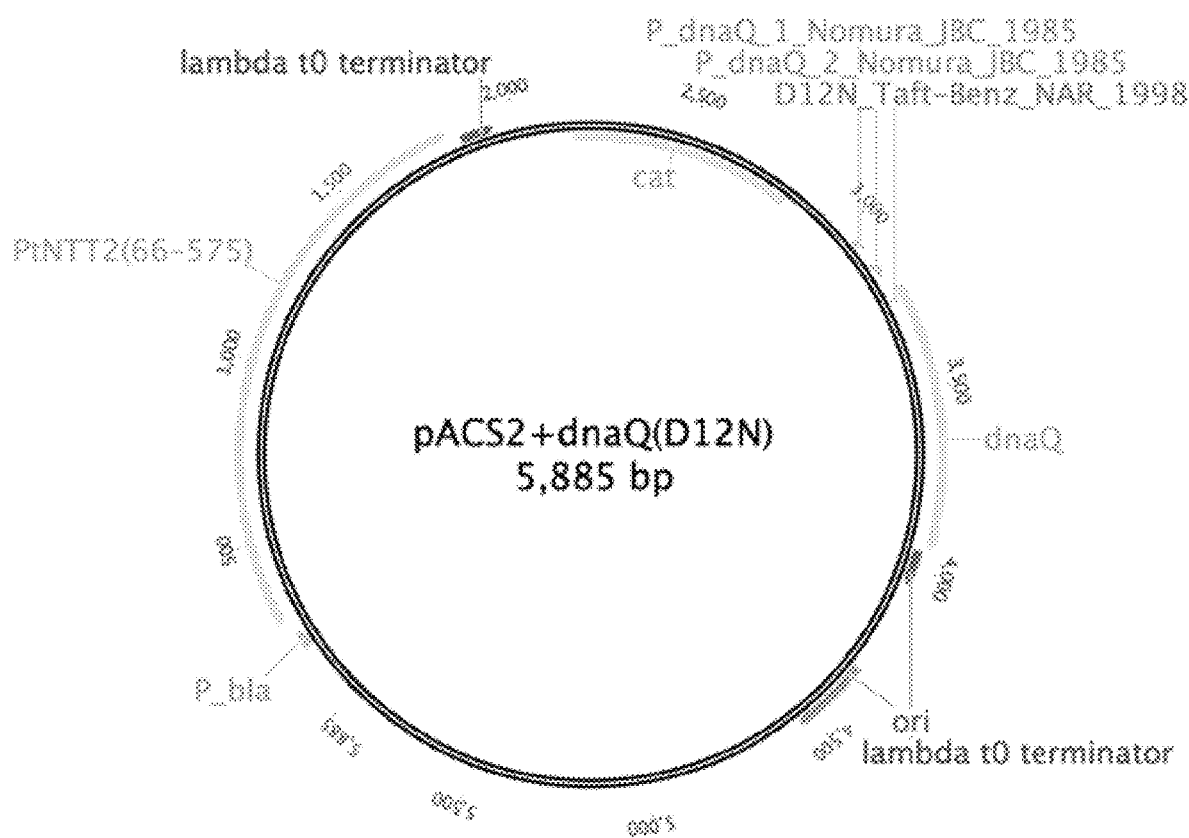
Figure 4C:
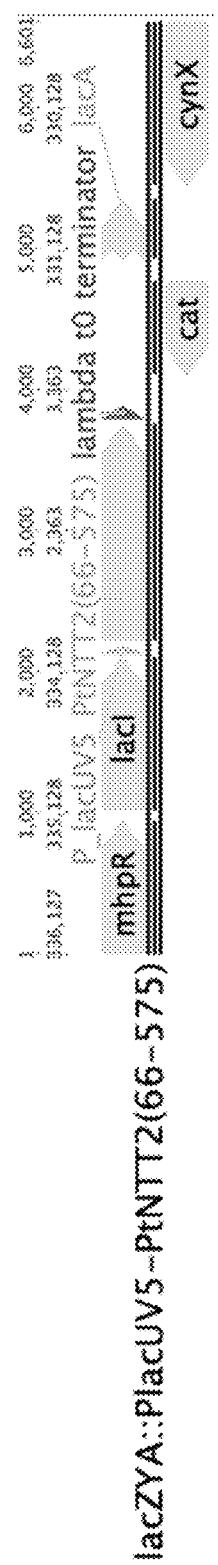
Figure 5:
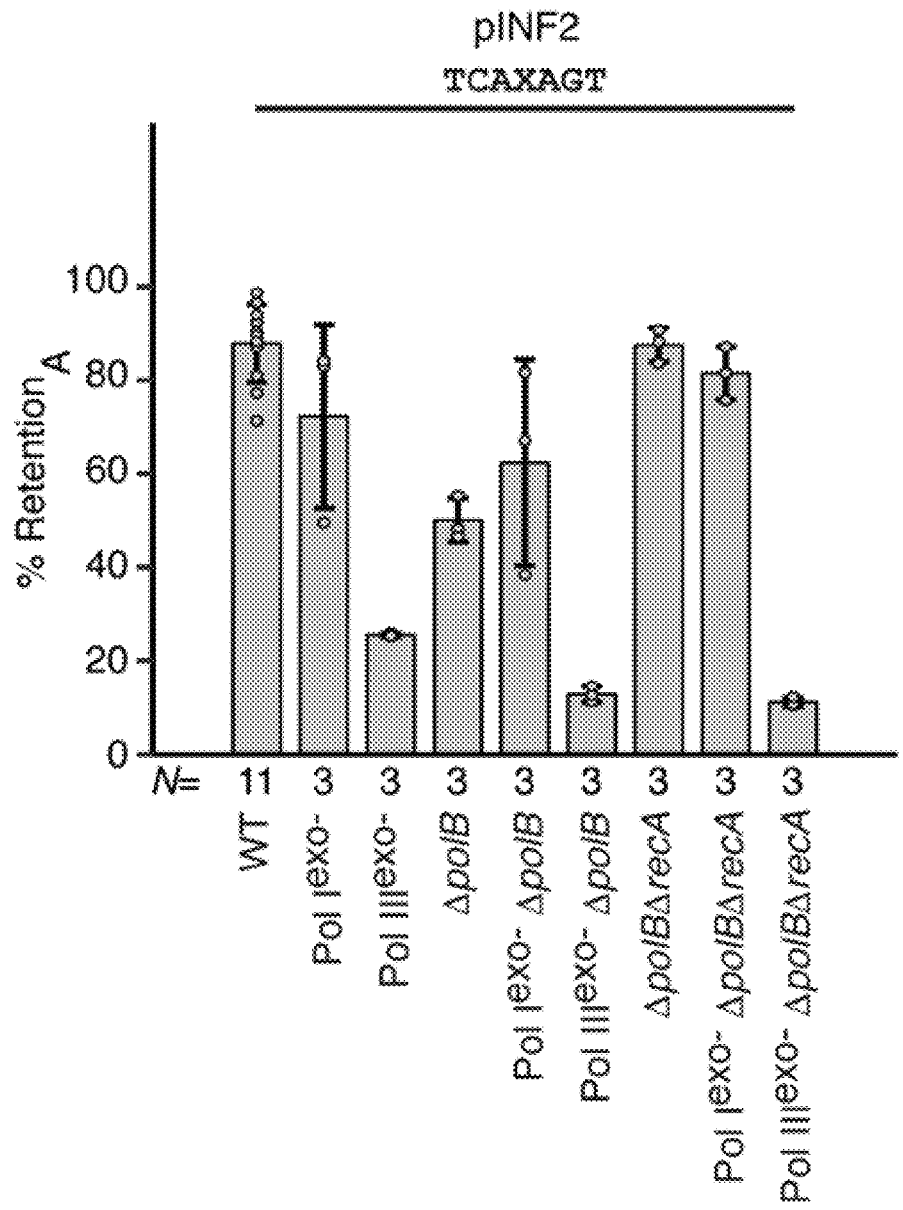
FIG. 5 illustrates exonuclease deficient polymerases replicating TCAXAGT pINF replication data for exonuclease deficient polymerase strains is shown. The same strains from FIG. 1E were also tested for their ability to replicate TCAXAGT (X=dNaM). N≥3 for all data shown; error bars represent 95% empirical bootstrap confidence intervals
Figure 6A:
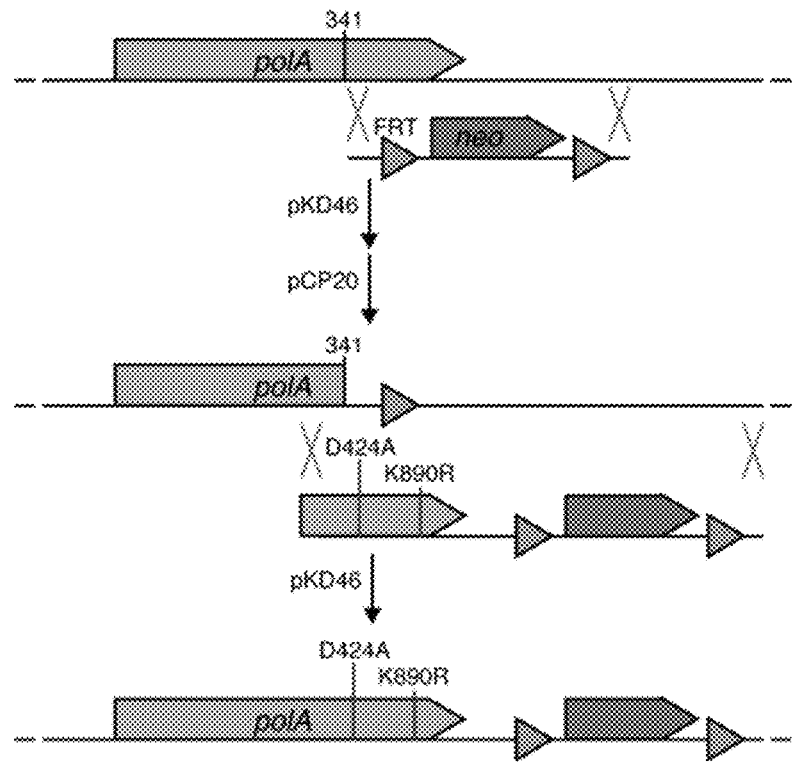
FIG. 6A-FIG. 6B illustrate polA(D424A, K890R), P_polB design. Construction strategy of polA(D424A, K890R) and derepressed PpolB are shown.
Figure 6B:
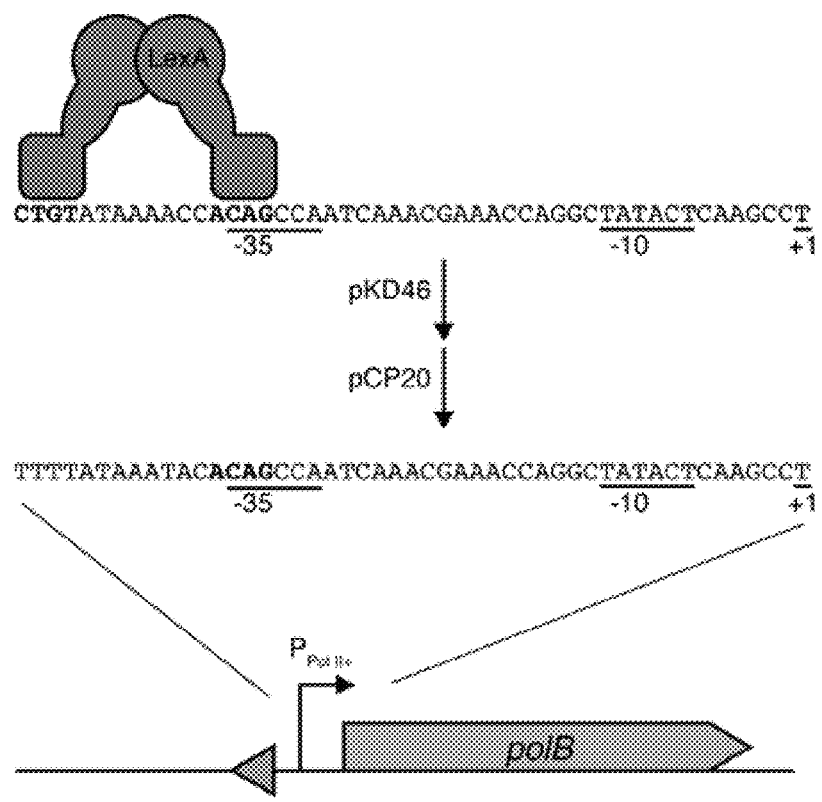

UBP retention might be optimized through the manipulation of RecA and Pol II. To explore this possibility, SSOs were optimized lacking recA and with or without Pol II constitutively expressed at SOS-derepressed levels (ΔrecA and Pol II$^+$ΔrecA, respectively (FIGS. 6A-6B). These strains (YZ3) also expressed an optimized PtNTT$_2$ transporter from a chromosomal locus (AlacZYA::P$_{lacUV5}$-PtNTT2(66-575)) (FIGS. 4A-4C). For comparison, the wild type strain with the same chromosomally integrated transporter (WT-Opt) was used. SSOs were transformed with pINF1, pINF5, or pINF6 (FIG. 6A), with pINF6 embedding the UBP in a sequence where its retention is particularly challenging, and plasmids were recovered from individual colonies to characterize UBP retention. In this case, selection on solid growth media was introduced to allow for analysis of UBP retention in individual clones, as opposed to the average UBP retentions determined in the previous experiments. A distribution of UBP retentions was observed with each plasmid in all SSOs, however, the distributions were shifted toward higher retention with the ΔrecA-Opt and especially the Pol II$^+$ΔrecA SSOs, compared to the WT-Opt SSO. Additionally, only the Pol II$^+$ΔrecA SSO produced clones with undetectable UBP loss in each sequence context examined. Notably, this was even true with pINF6, for which retention in the wild type SSO was undetectable, and only moderate (<60%) when enforced with Cas9 selection.

Figure 2A:
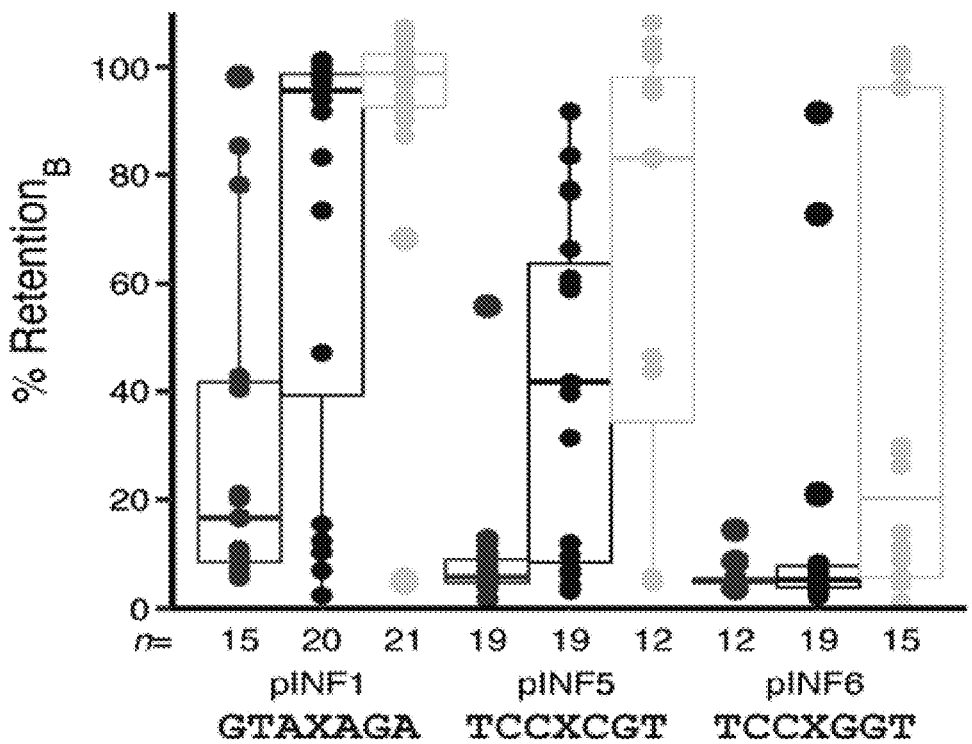
FIG. 2A-FIG. 2C illustrate replisome reprogramming results in optimized UBP retention.
Figure 2B:
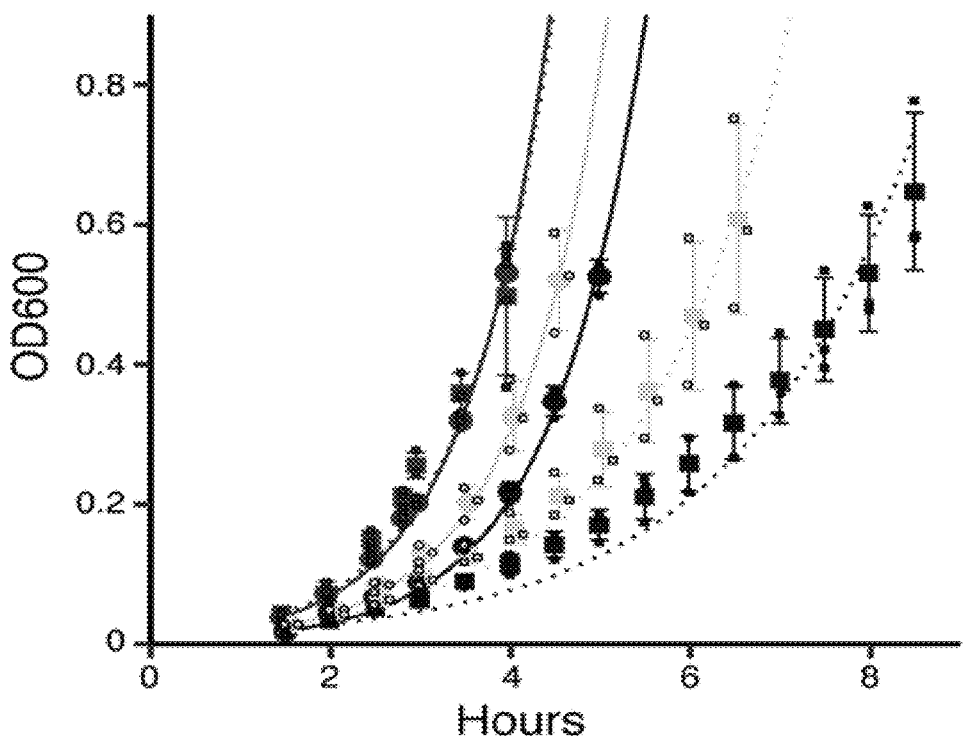
Figure 7A:
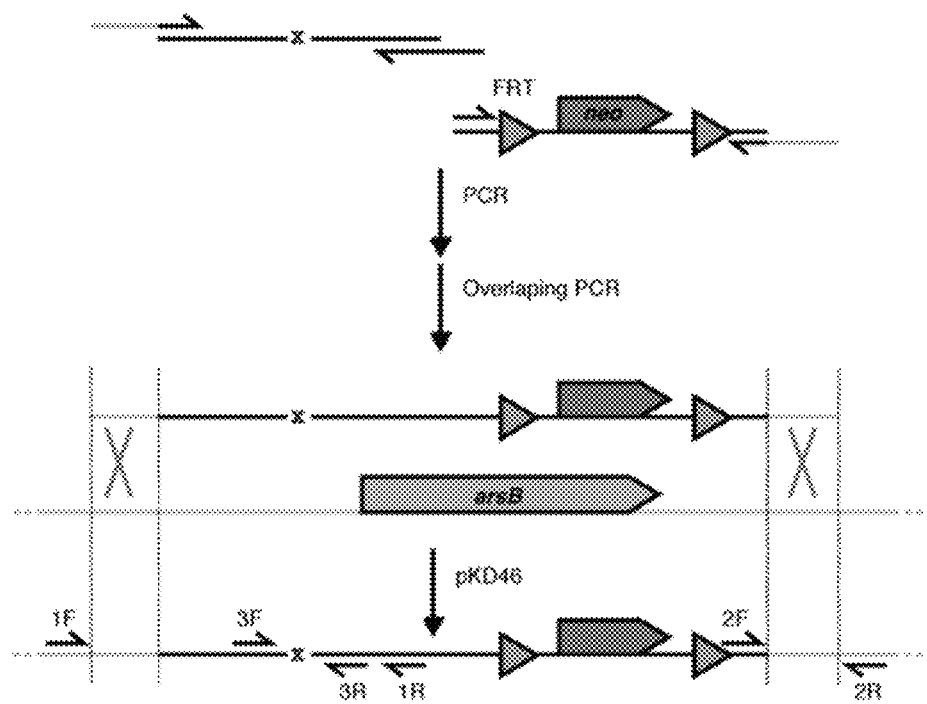
FIG. 7A-FIG. 7C illustrates UBP chromosomal integration.
Figure 7B:
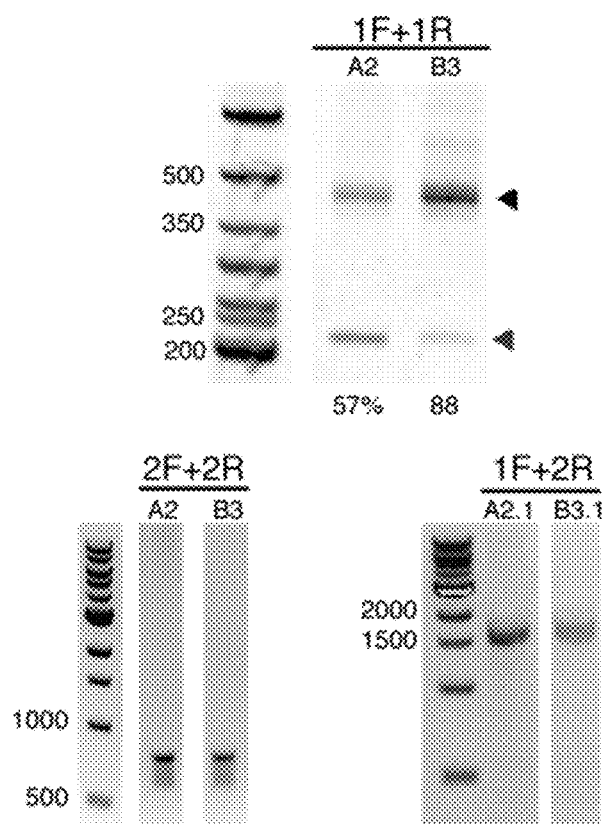
Figure 7C:
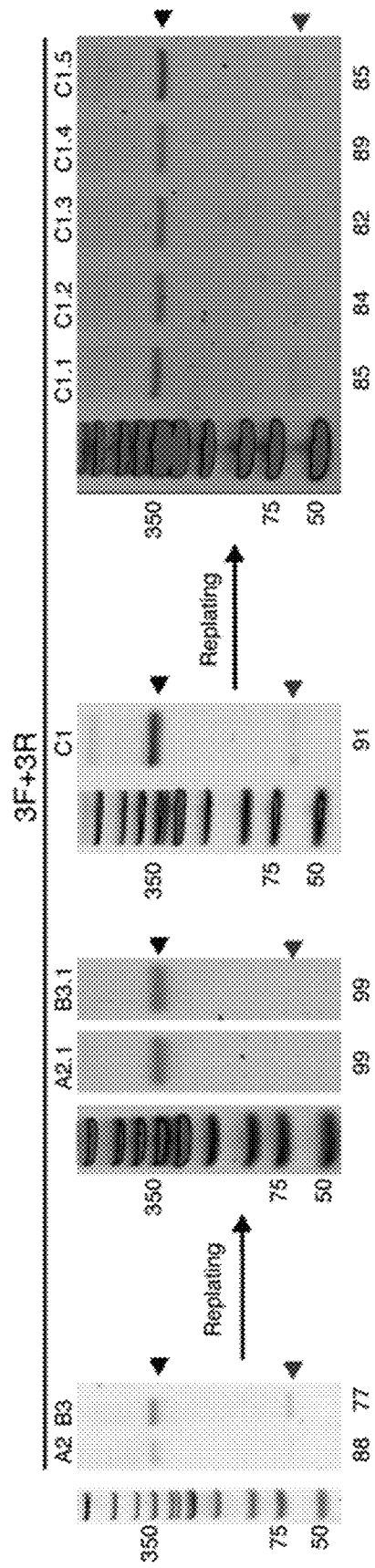
Figures 8A, 8B:
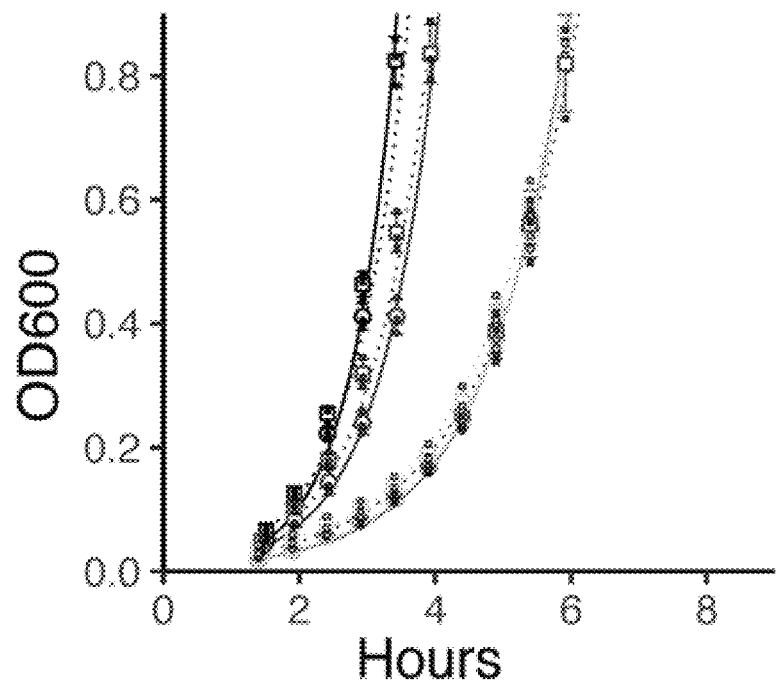
FIG. 8A-FIG. 8B show reprogrammed strains and chromosomal integrant doubling time characterization.

Whether the genetically optimized ΔrecA-Opt and Pol II$^+$ΔrecA SSOs could facilitate integration of the UBP into the chromosome was evaluated. An integration cassette was constructed that targets the sequence GTAXTGA (X=NaM) to the arsB locus, and used lambda red recombineering to integrate the cassette into the chromosomes of the WT-Opt, ΔrecA-Opt, and Pol II$^+$ΔrecA SSOs. Screening of integrants for UBP retention identified clones with 100% retention from the ΔrecA-Opt and Pol II$^+$ΔrecA SSOs, but despite significant effort we were unable to isolate WT-Opt clones with greater than 91% UBP retention (FIGS. 7A-7C), suggesting that significant UBP loss occurred during the required growth step. To characterize the effect of the chromosomally integrated UBP, aliquots of mid-log phase cells were inoculated into growth media with or without dNaMTP and dTPT3TP (FIG. 2B, FIGS. 8A-8B). The ΔrecA-Opt and Pol II$^+$ΔrecA integrants grew poorly when the unnatural triphosphates were not provided, consistent with the model that RER is required to efficiently bypass an unnatural nucleotide in the template. However, this growth defect was almost entirely eliminated in both SSOs when dNaMTP and dTPT3TP were provided. Thus, the deletion of recA and the overexpression of Pol II facilitate high-level retention of the UBP in the chromosome with only minimal consequence to fitness.

Figure 10A:
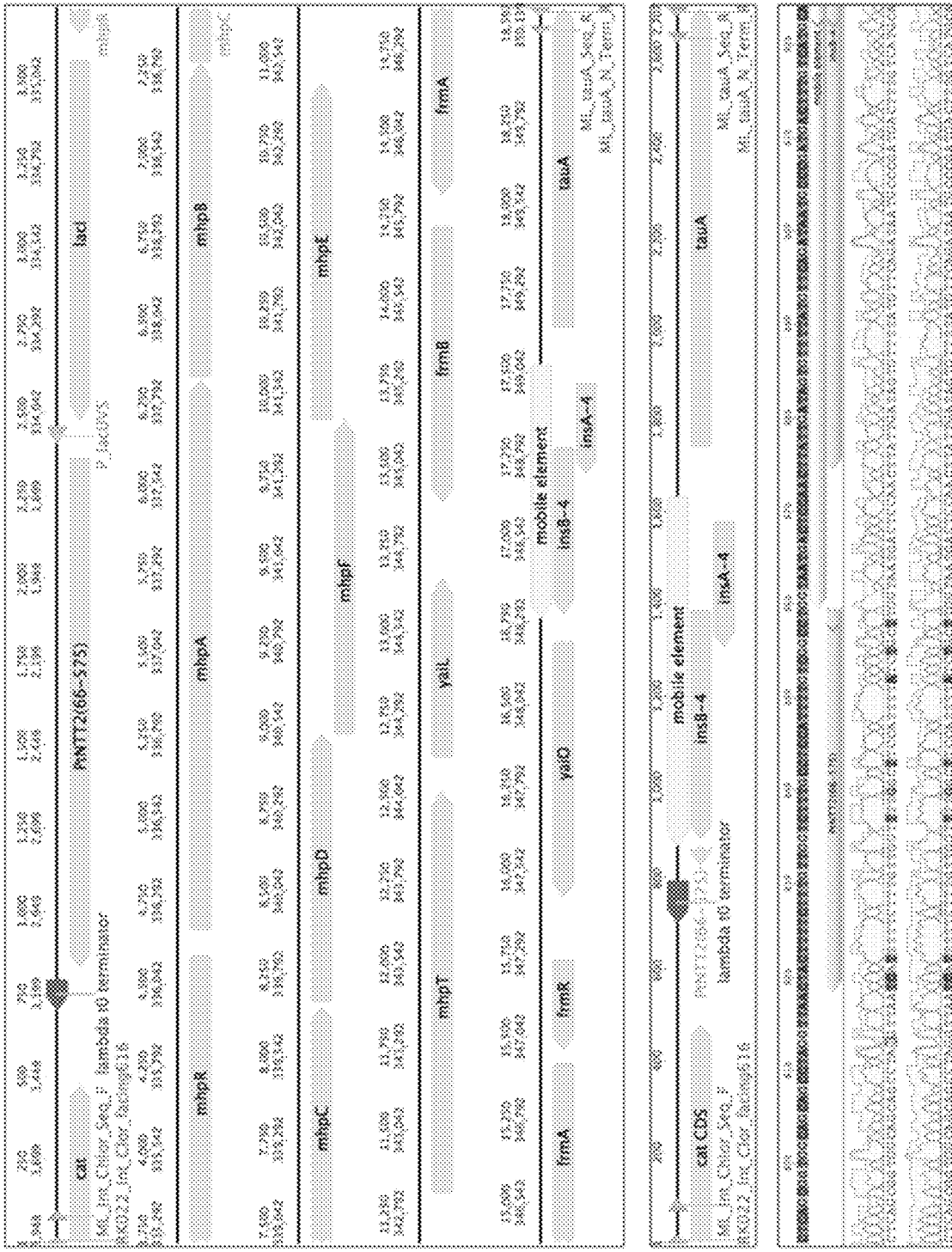
FIG. 10A-FIG. 10B illustrates WT-Opt chromosomal UBP integrants PtNTT2(66-575) mutation during passaging. A depiction of PtNTT2(66-575) mutation during passaging of WT-Opt and its characterization.
Figure 10B:
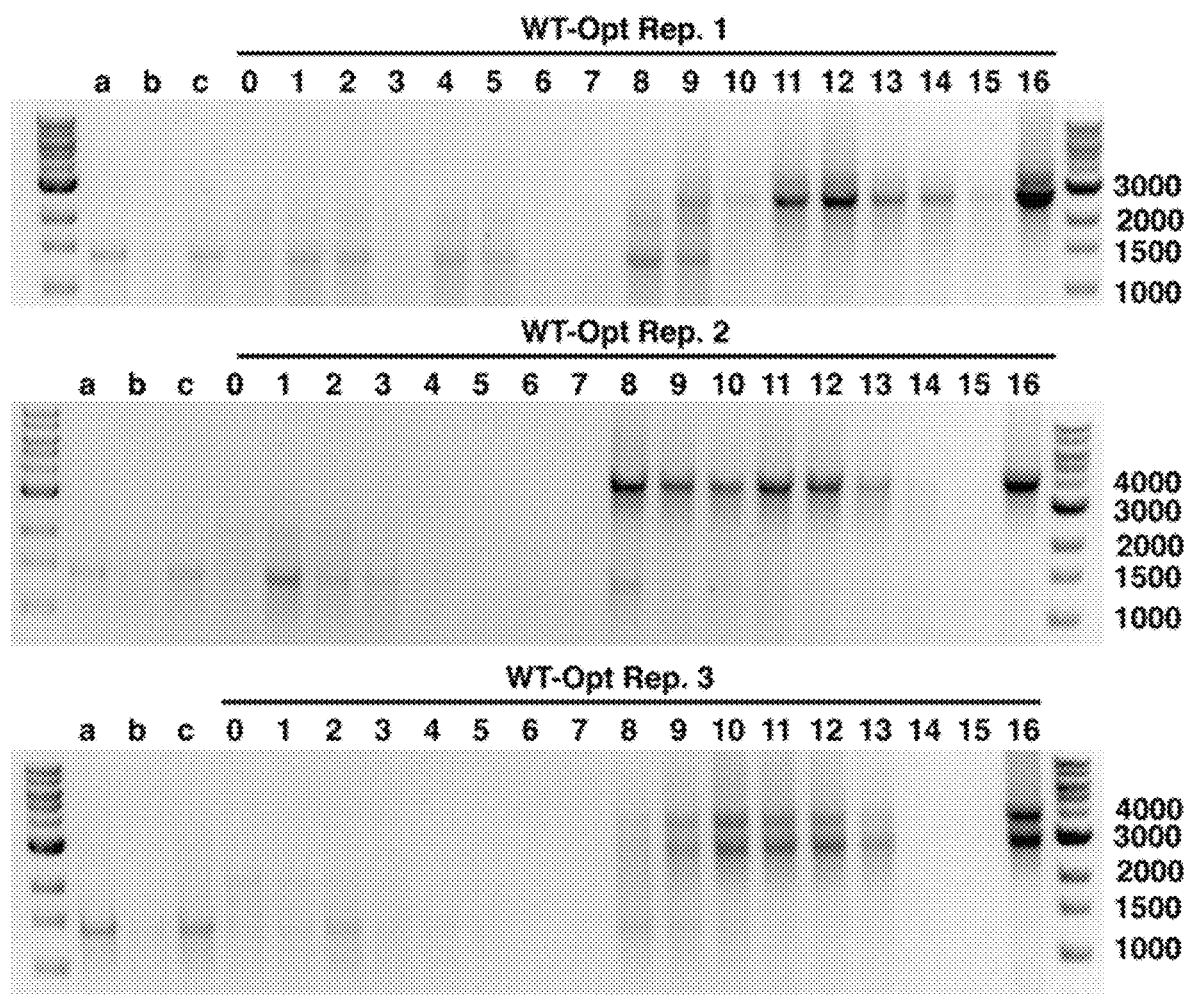

Finally, whether the genetically optimized strains facilitate the long-term stability of the chromosomally integrated UBP was evaluated. Previous studies have demonstrated that without Cas9-mediated selection for retention, a plasmid-borne UBP is lost during extended growth. The WT-Opt, ΔrecA-Opt, and Pol II$^+$ΔrecA integrants were serially passaged over many generations of growth and UBP retention characterized. With WT-Opt, the UBP was slowly lost until approximately the 40$^{th}$ generation, and then lost more rapidly with complete loss observed by the 90$^{th}$ generation. The apparently biphasic kinetics of loss suggest that at least one additional process contributes in addition to RER. Indeed, sequencing revealed a gross chromosomal rearrangement that eliminated the PtNTT2 gene at the time of the precipitous drop in UBP retention (FIGS. 10A-10B). In contrast to WT-Opt, both the ΔrecA-Opt and Pol II$^+$ΔrecA SSOs, the PtNTT2 remained intact and retention of the genomic UBP remained high, especially with the Pol II$^+$ΔrecA SSO, where it remained >55% after 137 generations.

These results demonstrate that not only does recA deletion facilitate UBP retention during replication, it significantly increases transporter stability during extended growth. The observed retention corresponds to a fidelity per doubling in excess of 99.6%, which in turn corresponds to loss of the chromosomal UBP in only a small fraction of the cells (<0.4%) per doubling. Thus, along with the Cas9-error elimination system, which was not employed in the current work, this error prevention system should allow for the retention of the UBP in a wide range of sequence contexts, which in turn should enable the storage of the entirety of the new information made possible by the UBP.

Since the last common ancestor of all life on earth, biological information has been stored in a four-letter alphabet. The reprogrammed replisome of the Pol II+ΔrecA SSO represents significant progress toward the unrestricted expansion of this alphabet, and the first progress mediated through the optimization of the cell itself. While the primary goals of the research were to understand how the UBP is replicated and to use that information to optimize the SSO, the results also provide a novel route to the study of how challenging replication is normally managed. For example, while the data suggests that a significant fraction of the DNA containing the UBP is replicated by Pol III, it also clearly reveals that a significant amount is not, and in these cases, the data reveal an interesting competition between Pol II-mediated replication restart and RecA-mediated RER. Such competitions may be common during challenging replication, which may have contributed to the challenges in identifying the normal roles of Pol II. Moreover, the inability of MMR to recognize the UBP suggests that helix distortions alone are insufficient and that the process requires specific interactions with the nucleobases that are not available with the unnatural nucleotides. Finally, the increased genetic stability afforded by deletion of recA may also have significant implications for methods directed at expansion of the genetic code via amber suppression, as these methods also suffer from genetic instability with extended growth. Regardless of these interesting issues, the reprogrammed SSO now allows for the more stable retention of increased biological information, including within its chromosome, and with the previous demonstration that this information can be retrieved in the form of proteins with non-canonical amino acids, should provide a platform to achieve the central goal of synthetic biology—the creation of life with new forms and functions.

Example 2. Methods and Materials pINF/UBP Containing DNA Construction pINFs were constructed through Golden Gate assembly of pUCX2 and insert dsDNA containing a dNaM-dTPT3 pair as described previously[3] with the following modifications. UBP containing dsDNA was produced with a 50-μL PCR with chemically synthesized UBP containing oligonucleotides (0.025 ng/μL), primers introducing BsaI sites and vector homology (1 μM), dTPT3TP (100 μM), dNaMTP (100 μM), dNTPs (200 μM), MgSO$_4$ (1.2 mM), OneTaq DNA Polymerase (0.025 U/μL), and OneTaq Standard Reaction Buffer (1x, New England Biolabs). The reaction was cycled through the following temperature regime on an MJ Research PTC-200 system (time in mm:ss): [94° C. 00:30|25 (94° C. 00:30|47° C. 00:30|68° C. 04:00)]. The resulting UBP containing dsDNA was purified using a DNA Clean & Concentrator-5 (Zymo Research) according to manufacturer recommendations. For pINF assembly, pUCX2 (1 μg) and insert DNA were combined at a 1:4 molar ratio in a 80 μL reaction with ATP (1 mM), T4 DNA ligase (6.65 U/μL, New England Biolabs), BsaI-HF (0.66 U/μL, New England Biolabs), and CutSmart Buffer (1x, New England Biolabs) and subjected to the following temperature regime: [37° C. 20 min|40x(37° C. 5 min|16° C. 10 min|22° C. 5 min)|37° C. 20 min|50° C. 15 min|70° C. 30 min]. BsaI-HF (0.33 U/μL) and T5 exonuclease (0.16 U/μL, New England Biolabs) were then added, and the reaction was incubated at 37° C. for 1 h to remove any pUCX2 without an insert. This reaction was purified using a DNA Clean & Concentrator-5 according to manufacturer recommendations except that reactions were mixed with 3 volumes of 1:1 DNA Wash:DNA Binding Buffer before binding to the silica column.

The UBP knock-in cassette for the arsB locus (FIGS. 7A-7C) was produced through overlapping PCR of a 150-bp dsDNA containing a UBP and the kanamycin resistance gene of pKD13. The 150 bp DNA was produced with a 50-μL PCR using the same reaction solution conditions as above and the following temperature regime (time in mm:ss): [98° C. 02:00|5x(98° C. 00:10|50° C. 00:10|68° C. 04:00)|15x(98° C. 00:10|58° C. 00:10|68° C. 04:00)]. The kanamycin resistance gene amplicon was produced through PCR amplification off pKD13 using Q5 DNA polymerase as per manufacturer recommendations. The amplification of long DNAs (approximately 200 bp or longer) is inhibited by the presence of dTPT3TP. Therefore, the overlap assembly PCR of the UBP containing amplicon and kanamycin resistance gene amplicon was performed on large-scale (2 mL of reaction mixture split into 40 individual 50-μL reactions) with the following solution conditions: UBP containing amplicon (0.02 ng/μL), kanamycin resistance gene amplicon (0.02 ng/μL), primers (1 μM), dTPT3TP (5 μM), dNaMTP (100 μM), dNTPs (200 μM), MgSO$_4$ (1.2 mM), OneTaq DNA Polymerase (0.025 U/μL), and OneTaq Standard Reaction Buffer (1 x). The reactions were subjected to the following temperature regime (time in mm:ss): [98° C. 02:00|5x(98° C. 00:10|50° C. 00:10|68° C. 04:00)|15x(98° C. 00:10|58° C. 00:10|68° C. 04:00)]. These reactions were pooled and concentrated using a DNA Clean & Concentrator-5 according to manufacturer recommendations.

In Vivo UBP Replication in Genetic Knockouts

All genetic knockouts (FIG. 1A-1E and FIG. 5) were assayed for their ability to replicate pINF-borne UBPs according to the following protocol. Electrocompetent cells were prepared from a 45-mL culture of mid-log phase cells (OD600 0.35-0.7) by pelleting cells and washing twice with 50 mL of 4° C. sterile diH$_2$O. Washed cells were resuspended in 4° C. sterile diH$_2$O at a final OD600 of 40-60. 50 μL of cells were mixed with 2 ng of a Golden Gate assembled pINF and transferred to an electroporation cuvette (2 mm gap, Cat. #FB102, Fisher Scientific). Electroporation was performed using a Gene Pulser II (BioRad) according to manufacturer recommendations (voltage 25 kV, capacitor 2.5 μF, resistor 200Ω). Transformed cells were diluted in 950 μL of 2xYT containing chloramphenicol (33 μg/mL) and potassium phosphate (50 mM, pH 7). 40 μL of diluted cells were further diluted into a final volume of 200 μL of 2xYT containing chloramphenicol (33 μg/mL), dTPT3TP (37.5 μM), dNaMTP (150 μM), and KPi (50 mM, pH 7), transferred to a 1.5 mL tube and allowed to recover for 1 h at 37° C. and 230 RPM. 10 μL of recovered cells were diluted into a final volume of 100 μL of 2xYT containing chloramphenicol (33 μg/mL) and ampicillin (100 μg/mL), dTPT3TP (37.5 μM), dNaMTP (150 μM) and potassium phosphate (50 mM, pH 7) in the well of a 96-well plate (Ref. #655161, Greiner Bio-One). Additionally, recovered cells were plated on 2xYT Agar (2%) containing ampicillin (100 μg/mL) and potassium phosphate (50 mM, pH 7) to estimate transformation efficiency. The 96-well and transformation efficiency plates were kept at 4° C. and 37° C. overnight (approximately 12 h), respectively. The transformation efficiency plate was inspected to ensure that all samples in the 96-well plate received at least 50 colony forming units before refrigeration. The 96-well plate was then transferred to 37° C. and 230 RPM. Cells were pelleted, decanted, and frozen after reaching 0.6-0.92 OD600. In vivo replicated pINFs were isolated using a ZR Plasmid Miniprep-Classic kit (Zymo Research) and a 5-µg silica column (Cat. #D4003, Zymo Research) according to manufacturer recommendations and advanced to biotin-shift PCR analysis. This procedure was performed in at least triplicate for each knockout strain starting from preparation of electrocompetent cells.

It should be noted that under these conditions replicates and strains undergo a similar but not identical number of cell doublings during the pINF replication experiment. However due to the pINFs unregulated origin of replication, matching cell doublings between replicates and strains does correspond to matching the number of pINF replication events. Therefore, the data in FIGS. 1A-1E and 2A are reported as % Retention values as opposed to estimated fidelities and should be interpreted as such.

Examination of Clonal pINFs

The ability of the optimized strains to clone pINFs was assessed (FIG. 2A) as described above with the following modifications. After recovery, dilutions of the recovered culture were plated on 2×YT containing agar (2%), carbenicillin (100 µg/mL), chloramphenicol (5 µg/mL), dTPT3TP (37.5 µM), dNaMTP (150 µM), and KPi (50 mM, pH 7). Plates were incubated at 37° C. for approximately 12 h. Individual colonies were picked and transferred to 100 µL of 2×YT containing carbenicillin (100 µg/mL), chloramphenicol (5 µg/mL), dTPT3TP (37.5 µM), dNaMTP (150 µM), and KPi (50 mM, pH 7) in the well of a 96-well plate. The 96-well plate was kept at 4° C. for approximately 12 h and then transferred to 37° C. and 230 RPM. Cells were pelleted, decanted, and frozen after reaching an $OD_{600}$ of 0.6-0.9. In vivo replicated pINFs were isolated using a ZR Plasmid Miniprep-Classic kit according to manufacturer recommendations and advanced to biotin-shift PCR analysis.

It should be noted that the Pol II$^+$ΔrecA strain used in these experiments (FIG. 2A) had a neo cassette at the former recA locus (P_polB(−)lexA-polB+FRT+ΔrecA+KanR+lacZYA::P_lacUV5-ΔΔ(CoOp)).

UBP Integration at arsB

The UBP integration cassette for the arsB locus was constructed as described above and depicted in FIGS. 7A-7C. Integration of this cassette was performed using standard lambda red recombineering with the following modifications. Overnight cultures of strains (WT-Opt, ΔrecA-Opt, and Pol II$^+$ΔrecA-Opt in 2×YT containing chlorampenicol (5 µg/mL), and KPi (50 mM, pH 7)) possessing pKD46 were diluted to 0.03 OD600 in 2×YT containing ampicillin (100 µg/mL), chloramphenicol (5 µg/mL), and KPi (50 mM, pH 7). Cultures were grown to approximately 0.1 $OD_{600}$ then induced with 0.4% L-(+)-arabinose and allowed to continue to grow to approximately 0.4 $OD_{600}$. Electrocompetent cells were prepared from these cultures as described above. 50 µL of electrocompetent cells were mixed with 960 ng (5 µL at 192 ng/µL) of the integration cassette described above and electroporated as described above. Transformed cells were diluted to a final volume of 1 mL of 2×YT containing chloramphenicol (5 µg/mL), dTPT3TP (37.5 µM), dNaMTP (150 µM), and KPi (50 mM, pH 7), transferred to a 1.5 mL tube, and allowed to recover for 2 h at 37° C. and 230 RPM. Cells were pelleted and resuspended in 115 µL of 2×YT containing chloramphenicol (5 µg/mL), dTPT3TP (37.5 µM), dNaMTP (150 µM), KPi (50 mM, pH 7). 15 µL samples of this cell suspension were plated on 2×YT containing agar (2%), kanamycin (50 µg/mL), chloramphenicol (5 µg/mL), dTPT3TP (37.5 µM), dNaMTP (150 µM), and KPi (50 mM, pH 7). Plates were incubated for 14-24 h at 37° C. Colonies were picked and transferred to 500 µL of 2×YT containing kanamycin (50 µg/mL), chloramphenicol (5 µg/mL), dTPT3TP (37.5 µM), dNaMTP (150 µM), KPi (50 mM, pH 7) in a 48-well plate (Ref. #677180, Greiner Bio-One). Plates were either refrigerated at 4° C. for ~12 h followed by incubation at 37° C. at 230 RPM or advanced directly to incubation. After reaching 0.6-1 $OD_{600}$ cultures were sampled as follows: 100 µL was combined with 100 µL glycerol (50%) and frozen at −80° C.; 350 µL was pelleted and frozen for later isolation of genomic DNA; 50 µL was pelleted, washed once with 200 µL diH$_2$O, pelleted, and resuspended in 200 µL.

The cell suspensions were analyzed by colony biotin-shift PCR. Genomic DNA was isolated from saved frozen cell pellets for samples that displayed high colony biotin-shift PCR percent shift values (≥80%) with a PureLink Genomic DNA Mini Kit (Thermo Fisher Scientific) according to manufacturer recommendations. Genomic DNA was analyzed by biotin-shift PCR. This analysis revealed high retention clones (Retention$_B$≥90%) for all genetic backgrounds. While these results confirmed successful chromosomal integration of the UBP and remarkably high retention of the UBP in chromosomal DNA, it was suspected that the cells depleted their media of dTPT3TP and dNaMTP during the integration protocol given the protocol's requirement to incubate cells at high cell density. Actively growing cultures of E. coli are known to degrade extracellular dTPT3TP and dNaMTP to their corresponding di- and mono-phosphate and nucleoside species. To address this possibility the glycerol stocks of the highest retention samples were used to inoculate 100 µL of 2×YT containing kanamycin (50 µg/mL), chloramphenicol (5 µg/mL), dTPT3TP (37.5 µM), dNaMTP (150 µM), and KPi (50 mM, pH 7) in a 96-well plate. Cultures were grown to approximately 0.6 $OD_{600}$ at 37° C. at 230 RPM. Cells from this culture were plated, picked, grown, and sampled as described above. This "replating" procedure quickly revealed clones for the ΔrecA-Opt and Pol II$^+$ΔrecA-Opt SSOs with undetectable chromosomal UBP loss (Retention$_B$=100%). However despite screening 12 clones for the WT-Opt SSO, no clones with Retention$_B$>91% were discovered. Therefore, we chose to use a WT-Opt integrant (Retention$_B$=91%) that did not undergo the replating procedure for the doubling time and passaging experiments. For ΔrecA-Opt and Pol II$^+$ΔrecA-Opt we selected one clone each with Retention$_B$=100% for the doubling time and passaging experiments.

It should be noted that the Pol II$^+$ΔrecA strain used in these experiments (FIG. 2A and FIG. 2C) did not have a neo cassette at the former recA locus (P_polB(−)lexA-polB+ΔrecA+FRT+lacZYA::P_lacUV5-ΔΔ(CoOp)).

Determination of Strain Doubling Time

Mid-log phase cells WT-Opt, ΔrecA-Opt, and Pol II$^+$ΔrecA-Opt SSOs and their corresponding chromosomal UBP integrants (described above) were prepared using the following procedure. Saturated overnight cultures were prepared by inoculation of 2×YT containing chloramphenicol (5 µg/mL), dTPT3TP (37.5 µM), dNaMTP (150 µM), and KPi (50 mM, pH 7) from glycerol stock stabs and overnight growth (approximately 14 h) at 37° C. at 230 RPM. These cells were diluted to 0.03 $OD_{600}$ in 500 µL 2×YT containing chloramphenicol (5 µg/mL), dTPT3TP (37.5 µM), dNaMTP (150 µM), and KPi (50 mM, pH 7) and grown at 37° C. at 230 RPM. Growth was monitored by $OD_{600}$. Once cells reached mid-log phase (0.3-0.5 $OD_{600}$), they were diluted to 0.013 $OD_{600}$ in 500 µL 2×YT containing chloramphenicol (5 µg/mL), dTPT3TP (37.5 µM), dNaMTP (150 µM), and KPi (50 mM, pH 7) or 2×YT containing chloramphenicol (5 µg/mL) and KPi (50 mM, pH 7) in a 48-well plate and grown at 37° C. at 230 RPM. $OD_{600}$ was measured every 30 min. This procedure was performed in triplicate for each strain starting from inoculation of overnight cultures.

$OD_{600}$ data from each experiment was analyzed to obtain a theoretical cell doubling time (FIG. 2B and FIGS. 8A-8B). $OD_{600}$ measurements corresponding to the exponential growth phase (0.01-0.9) were fit to the following exponential growth model using R version 3.2.4:

$$OD_i = OD_0 * 2^{C_{Growth}*t}$$

Where $OD_i$ is the $OD_{600}$ at time (t), $OD_0$ is minimum $OD_{600}$ value for a given data set, and $C_{Growth}$ is the growth constant. $C_{Growth}$ was fit using the "nls( )" command. Doubling times (DT) were calculated using the following equation:

$$DT = \frac{1}{C_{Growth}}$$

Passaging of Strains Bearing a Genomic UBP

Glycerol stock stabs of chromosomal UBP integrants from the WT-Opt, ΔrecA-Opt, and Pol II⁺ΔrecA-Opt SSOs (described above) were used to inoculate 500 µL of 2×YT containing kanamycin (50 µg/mL), chloramphenicol (5 µg/mL), dTPT3TP (37.5 µM), dNaMTP (150 µM), and KPi (50 mM, pH 7). Cells were grown to mid log phase (0.5-0.8 $OD_{600}$) at 37° C. at 230 RPM and then diluted to 0.03 $OD_{600}$ in 500 µL of 2×YT containing kanamycin (50 µg/mL), chloramphenicol (5 µg/mL), dTPT3TP (37.5 µM), dNaMTP (150 µM), and KPi (50 mM, pH 7) in a 48-well plate and grown at 37° C. at 230 RPM. The cultures inoculated at 0.03 $OD_{600}$ were considered the starting point (Doublings=0) for passaging. The cultures were grown to 1-1.5 $OD_{600}$ corresponding to approximately 5 cell doublings. This growth from 0.03 to 1-1.5 $OD_{600}$ was considered one "passage" with one passage corresponding to approximately 5 cell doublings. After these samples reached 1-1.5 $OD_{600}$, another passage was started by diluting cells to 0.03 $OD_{600}$ in fresh media of the same composition. After dilution, the 1-1.5 $OD_{600}$ culture was sampled as follows: 100 µL was combined with 100 µL glycerol (50%) and frozen at −80° C.; 350 µL was pelleted and frozen for later isolation of genomic DNA; and 50 µL was pelleted, washed once with 200 µL $diH_2O$, pelleted, and resuspended in 200 µL. The passaging process was repeated for a total of 15 passages, corresponding to approximately 80 cell doublings for all three strains.

Throughout passaging, colony biotin-shift PCR analysis was performed on the cell suspension samples. This revealed that retention had declined to <10% in WT-Opt after 15 passages. Therefore, this strain was no longer passaged. In contrast, retention remained at 60-80% in ΔrecA-Opt and Pol II⁺ΔrecA-Opt. Therefore, an additional passage was performed as above for these strains. Retention remained unchanged now a total 16 passages. Therefore, these strains were subjected to 4 additional passages at a higher dilution factor that corresponded to approximately 13 cell doublings per passage (growth from approximately 0.0001 to 1-1.5 $OD_{600}$). At this point ΔrecA-Opt and Pol II⁺ΔrecA-Opt integrants had experience approximately 130 cell doublings and UBP retention remained >40% according to colony biotin-shift PCR analysis. Further passaging was deemed unnecessary and the experiment was stopped for more rigorous analysis of the genomic DNA samples gathered during passaging. This experiment was performed in triplicate starting from inoculation of media with the genomic integrant glycerol stock stabs.

Figure 2C:
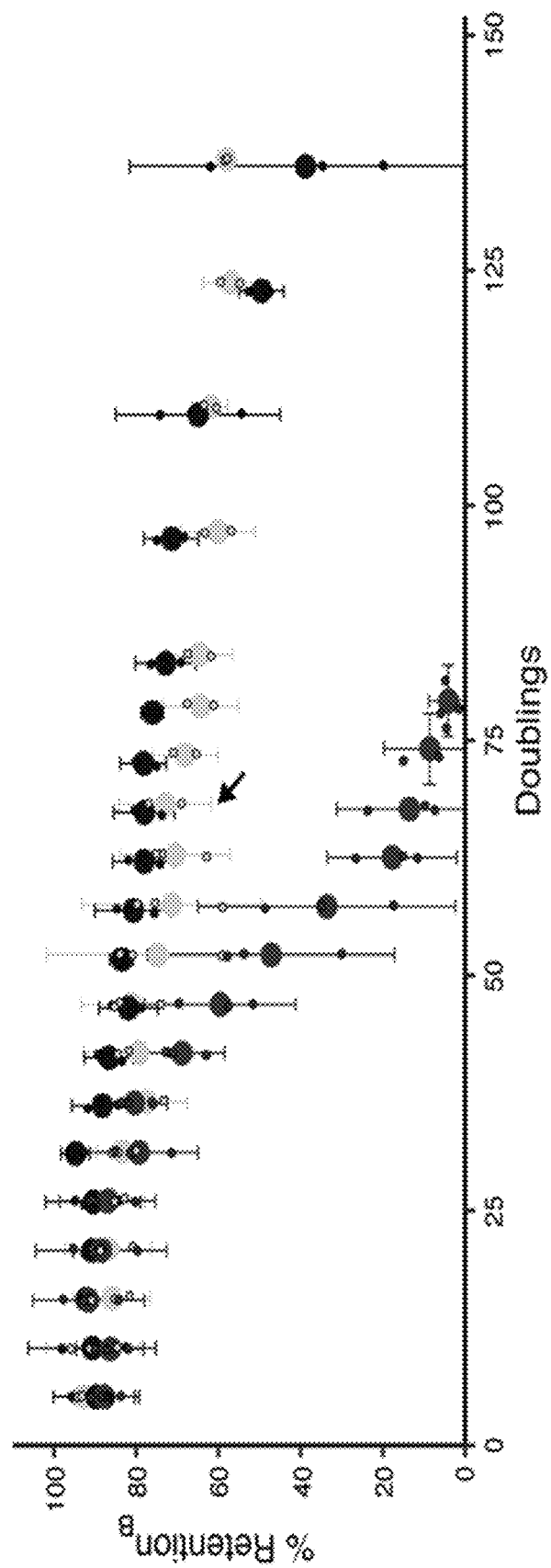
Figure 3:
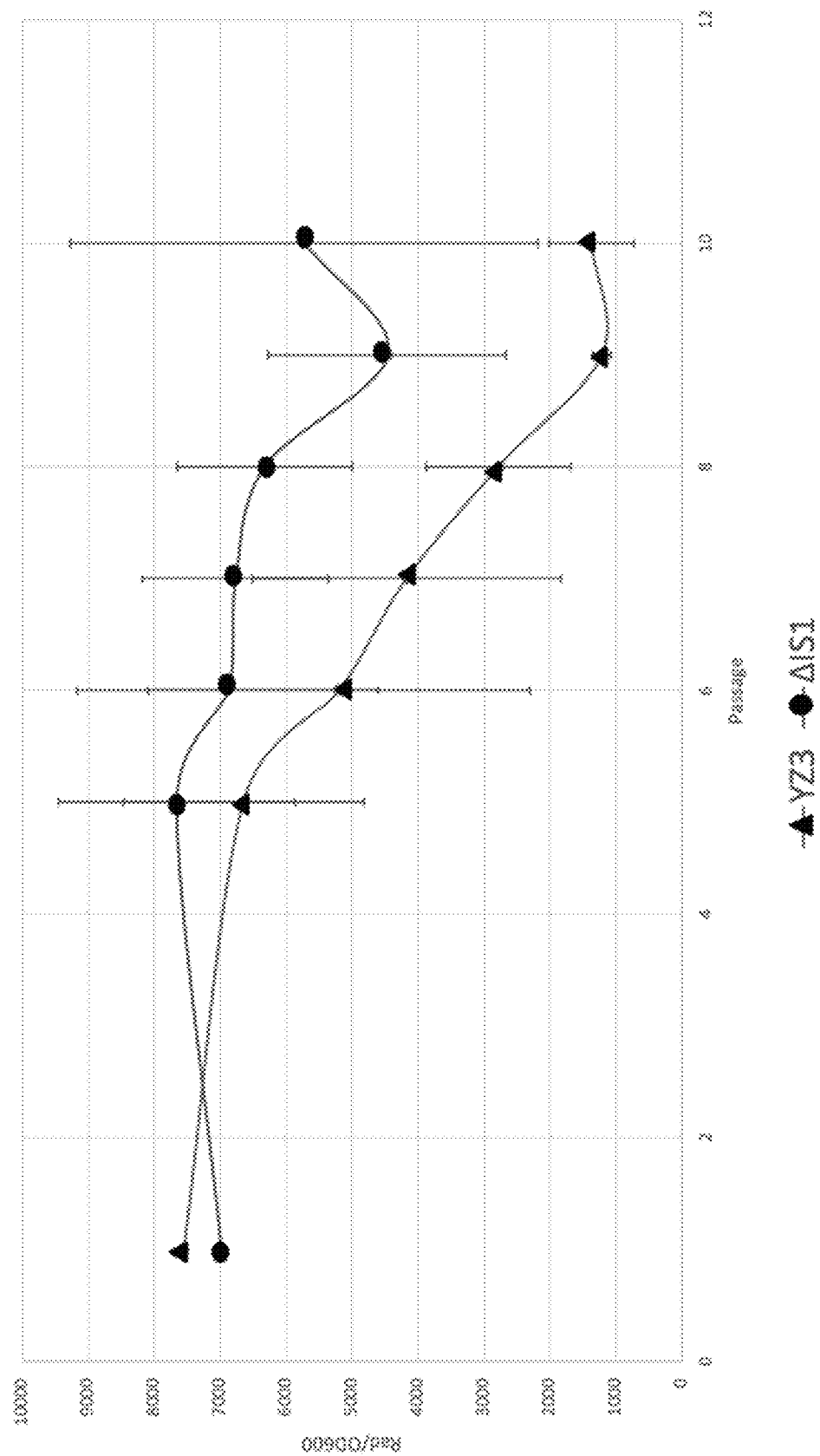
FIG. 3 illustrates increased PtNTT2 activity over long-term growth (10 passages) in strains containing a knockout of IS1, as compared to YZ3 strain that has been engineered to constitutively express a modified PtNTT2 nucleotide transporter gene from the chromosomal lacZYA locus.

After completing the passaging experiment, genomic DNA was isolated and analyzed by biotin-shift PCR (FIG. 2C). The slow, then rapid loss of the UBP in WT-Opt suggested that multiple processes contributed to UBP loss. It was suspected that the $P_{lacUV5}$-PtNTT2(66-575) may have been mutated during the experiment, as expression of PtNTT2 causes a slight growth defect. Thus, cells that inactivate the transporter through mutation gain a fitness advantage and can rapidly dominate the experimental population. This hypothesis was explored through isolation of individual clones from the end of WT-Opt passaging and PCR analysis of purified genomic DNA (see FIGS. 10A-10B). Primer walking for several clones revealed that all genes between cat and insB-4 including PtNTT2(66-575) had been deleted in these cells. The insB-4 gene encodes one of two proteins required for the transposition of the IS1 transposon. Sequencing of one clone confirmed that IS1 inserted at PtNTT2(66-575)(T1495) corresponding to a 15890 base pair deletion.

After confirmation of the PtNTT2(66-575) mutation event, the emergence of deletion mutants was assessed by PCR analysis of genomic DNA samples from WT-Opt integrant passaging (see FIG. 10B). This analysis revealed that several amplicons of sizes corresponding to IS1-mediated PtNTT2(66-575) deletion events appear in passaging samples during the rapid phase of UBP loss.

Figure 9A:
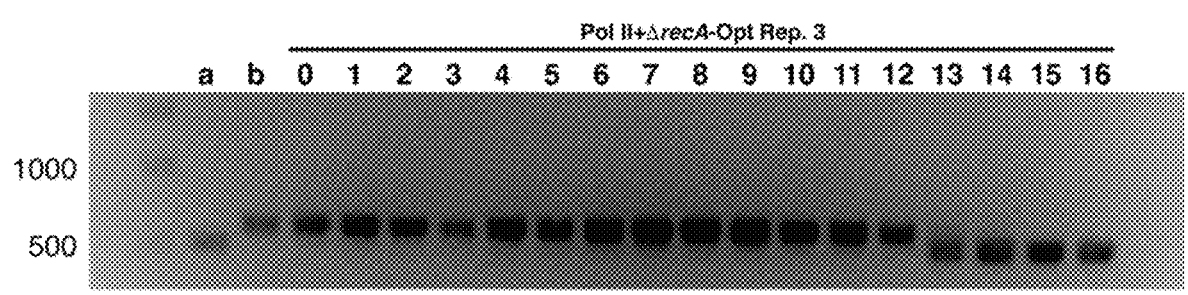
FIG. 9A-FIG. 9B shows Pol II+ ΔrecA-Opt chromosomal UBP integrant contamination with WT-Opt cells. Replicate 3 of the Pol II+ ΔrecA-Opt integrant was contaminated with WT-Opt cells at passage 13.
Figure 9B:
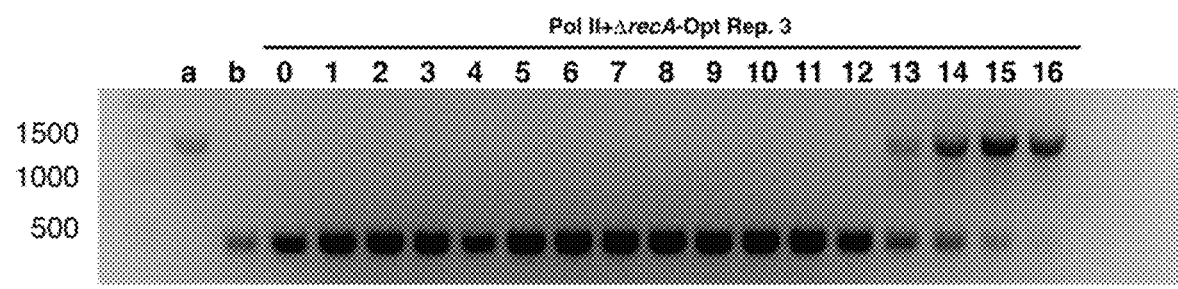

It was also observed that one replicate of the Pol II⁺ΔrecA-Opt integrant rapidly lost the UBP at the same time as the WT-Opt integrants, strongly suggesting that this replicate may have been contaminated with WT-Opt cells during the passaging. This possibility was confirmed using colony PCR analysis, which revealed that this replicate became contaminated with WT-Opt cells at passages corresponding rapid loss of the UBP (see FIGS. 9A-9B). Therefore, data from this replicate was only used from samples without WT-Opt cell contamination.

Bacterial Strains and Plasmids

All strains used in this study were constructed from E. coli-BL21(DE3) through lambda red recombineering unless otherwise indicated. Gene knock-out cassettes were obtained through PCR amplification (using either OneTaq or Q5 according to manufacturer recommendations (New England Biolabs)) of either genomic DNA of Keio collection strains or pKD13 with the relevant primers. Functional genetic knock-in cassettes, polA(D424A,K890R) and Pol 11+(FIGS. 7A-7C) were constructed through overlapping PCR. Strains were made competent for dXTP import through either transformation with pACS2 or pACS2-dnaQ (D12N) or integration of the PlacUV5⁻PtNTT2(66-575)+cat cassette at the lacZYA locus (FIGS. 4A-4C). The construction of pACS2 and $P_{lacUV5}$-PtNTT2(66-575)+cat has been described previously. pACS2-dnaQ(D12N) was constructed through Gibson assembly of PCR amplicons. PtNTT2 function was confirmed in every relevant strain using a radioactive dATP uptake assay.

Exonuclease Deficient Pol I and III.

DNA Pol I and III are conditionally essential and essential genes, respectively. Therefore, unlike the SOS-regulated polymerases they could not be examined by genetic knockout. Instead we constructed 3'-5' exonuclease deficient mutants for these enzymes. Pol I (polA) was made 3'-5' exonuclease deficient by mutating the active site of its exonuclease domain (D424A). This was accomplished through two phases of lambda red recombineering (FIGS. 7A-7C). First polA was truncated to its 5'-3' exonuclease domain (removing both polymerase and 3'-5' exonuclease domains). Second polymerase and 3'-5' exonuclease domains were reintroduced with the D424A mutation. Due to the length of the gene, PCR mutations were generated in the amplicon used for integrations. This resulted in the K890R mutation. However, since K890 is a surface exposed residue on a disordered loop of the protein its mutation to arginine was expected to have minimal effect on protein function. Moreover, a lysine to arginine maintains approximate charge and size of the residue.

DNA Pol III holoenzyme is a multi-enzyme complex with separate polymerase and 3'-5' exonuclease enzymes. The exonuclease enzyme (dnaQ) is thought to play a structural role in the Pol III holoenzyme in addition to its editing activity. Therefore, deletion of dnaQ removes Pol III editing activity but also prevents cell growth unless compensatory mutations are added to other parts of the holoenzyme. Therefore, we chose to examine Pol III's role in UBP replication through expression of a mutator dnaQ mutant (D12N) from the plasmid, pACS2+dnaQ(D12N) (FIGS. 4A-4C). The expression of dnaQ(D12N) from a multicopy plasmid has been previously demonstrated to produce a dominant mutator phenotype in E. coli despite the expression of wild-type DnaQ from the chromosomal copy of the gene. pACS2+dnaQ(D12N) expresses dnaQ(D12N) with both of the native gene promoters.

Fitness Costs from Genetic Optimization of the SSO.

Deletion of recA clearly leads to greatly improved retention of the UBP in many sequences. While this is highly desirable, recA deletion does carry some fitness costs. Strains deficient in recA are known to have lower tolerance for DNA damage. However given that all near-term applications of the SSO will take place in highly controlled environments, we do not expect this to be problematic. Additionally, recA deletion increases the doubling time as measured in FIGS. 8A-8B. However, these experiments were performed primarily to illustrate the difference in growth rate for strains bearing a chromosomal UBP growing in the presence or absence of dNaMTP and dTPT3TP. Several factors complicate directly relating strain fitness to the measured doubling times. The main complication is that cells in solution can increase OD600 by altering their morphology rather than actually increasing cell number. Regardless, the measured doubling time for L recA-Opt (~18 min longer than WT-Opt) suggests that deletion of recA leads to a significantly reduced growth rate. However given the benefits of this modification, this reduced growth rate is an acceptable trade-off. It should also be noted that some data points in FIGS. 8A-8B are difficult to rationalize. For example, the presence of the chromosomal UBP appears to decrease the doubling time in L recA-Opt and Pol II⁺L recA-Opt.

Biotin-Shift Analysis

Retention of UBPs in pINFs and chromosomal DNA was measured as described previously with the following modifications. All biotin-shift PCRs were run in a 15-μL volume with primers (1 μM), d5SICSTP (65 μM), dMMO2bioTP (65 μM), dNTPs (400 μM), MgSO₄ (2.2 mM), OneTaq DNA Polymerase (0.018 U/μL), DeepVent DNA Polymerase (0.007 U/μL, New England Biolabs), SYBR Green I (1×, Thermo Fisher Scientific) and OneTaq Standard Reaction Buffer (1×). The amount of sample DNA added to a biotin-shift PCR and the temperature regime varied depending on the nature of the sample.

For in vivo replicated pINFs (FIGS. 1A-1E) from the genetic knockout experiments, the exact concentration of pINF DNA could not be determined as pINF and pACS2 DNA were both captured by the ZR Plasmid Miniprep-Classic kit. Therefore, 0.5 μL (approximately 3 ng total DNA) of the purified sample was used as template DNA for biotin shift PCR. Reactions were subjected to the following temperature regime (time in mm:ss) in a CFX Connect Real-Time PCR Detection System (BioRad): [96° C. 02:00|2-18×(96° C. 00:15|48° C. 00:15|68° C. 04:00)]. Reaction progression was monitored by SYBR Green I fluorescence and reactions were stopped and stored at 4° C. at the end of the 68° C. step just after the reaction exited the exponential phase of PCR (typically 17 cycles). For clonal pINF experiments (FIG. 2A), 3 ng of purified plasmid DNA was used as template DNA for biotin-shift PCR analysis. Reactions were subjected to the same temperature regime and monitoring as above.

Golden Gate constructed pINFs and UBP containing oligonucleotides were amplified as described above using 1 ng and 7.5 μg, respectively, of sample as template DNA for the biotin-shift PCR.

For the chromosomal UBP experiments, both colony biotin shift PCR and biotin shift PCR amplification of purified genomic DNA was performed. For colony biotin shift PCR, 2 μL of cell suspension (see above) was added to biotin shift PCR as template. Reactions were subjected to the following temperature regime and monitored as above (time in mm:ss): [96° C. 02:00|5×(96° C. 00:15|60° C. 00:15|68° C. 04:00)|20-22×(96° C. 00:15|48° C. 00:15|68° C. 04:00)]. For biotin shift PCR amplification of purified genomic DNA, 30-125 ng of purified genomic DNA was used as template for biotin shift PCR. These reactions were subjected to the following temperature regime and monitored as above (time in mm:ss): [96° C. 02:00|5×(96° C. 00:15|60° C. 00:15|68° C. 04:00)|10-16×(96° C. 00:15|48° C. 00:15|68° C. 04:00)].

The percentage of biotin labeled amplicons from any of the biotin shift PCRs described above was determined by mixing 1 μL of biotin-shift PCR with 2.5 μL of streptavidin (2 μg/μL, Promega) and 1 μL of Purple Loading Dye (6×, New England Biolabs) and resolving streptavidin-DNA complexes on a native 6% polyacrylamide gel. Gels were stained in 50 mL TBE with 1×SYBR Gold (Thermo Fisher Scientific). Gels were imaged on a Molecular Imager Gel Doc XR System (Bio-Rad, Hercules, CA) with a 520DF30 62 mm (Bio-Rad) filter. Image exposure time was limited to prevent saturation of the CCD for pixels in the bands of interests. The fluorescence intensity of DNA and streptavidin-DNA bands was quantified using Quantity One software v4.6.9 (Bio-Rad) using local background subtraction. The percent shift (S) was then calculated for each sample based on the pixel volume of the DNA (VDNA) and streptavidin-DNA(VSA-DNA) bands.

Quantification of UBP retention by biotin-shift PCR analysis requires normalization of sample shift values to the shift value of an in vitro constructed UBP containing DNA. For the in vivo replication experiments in genetic knockouts (FIGS. 1A-1E) sample percent shift values ($S_S$) were normalized to the percent shift of the Golden Gate assembled $pINF_{(SGG)}$ used to initiate the in vivo replication experiment ($Retention_A$).

While dTPT3-dNaM and related analogs have been demonstrated to be replicated in PCR with high fidelity and with limited sequence context bias, the UBP is mutated with some frequency in PCR. Therefore, pINF production by Golden Gate assembly of PCR-generated UBP containing DNA results in the production of some mutant, fully natural pINFs. Given that the experiments presented in FIGS. 1A-1E did not isolate individual pINF transformants, these fully natural pINFs will be transformed into experimental cells and replicated alongside UBP-containing pINFs. This places an upper bound on the theoretical maximum percent shift value for a given sample. If no UBP loss occurs in vivo, the percent shift of an in vivo sample will equal that of the Golden Gate assembled pINF used to initiate the experiment (Retention$_A$=100%). Some replicates (particularly in the ΔrecA backgrounds) displayed over 100% Retention$_A$. This likely results from sampling of the Golden Gate assembled pINFs. If the transformation happens to result in transformation of only UBP containing plasmids and the cells replicate these plasmids with no UBP loss, normalization of $S_S$ to $S_{GG}$ will result in a value greater than 100%. If UBP replication occurs with perfect fidelity, the same logic applies to any sampling of the Golden Gate assembled pINFs that results in a higher percentage of UBP containing pINFs in the cells than the Golden Gate products. Thus, this is most apparent in the ΔrecA strains due to their high UBP retention.

The clonal pINF and chromosomal UBP experiments (FIGS. 2A-2C) did examine individual pINF transformants. Therefore, PCR-mutated fully natural pINFs can produce individual clones that display no UBP content ($S_S$=0%), but they do not impact the retention of other clones that received a UBP-containing pINF. Thus, SSOs that receive and faithfully replicate a UBP-containing pINF can be expected to have shift values that match the shift value of biotin-shift PCR analysis of a chemically synthesized UBP-containing oligonucleotide (assumed to have 100% UBP content). To convert sample shift values to retention values (Retention$_B$) for the experiments shown in FIGS. 2A-2C, sample shift values ($S_S$) were normalized to the shift values of chemically synthesized UBP-containing oligonucleotides ($S_O$). If no UBP loss occurs in vivo, the percent shift of the in vivo sample will equal that of the chemically synthesized UBP containing oligonucleotide (Retention$_B$=100%).

Outlier and Low Golden Gate Assembled pINF Removal

All data gathered is presented with the following exceptions. One outlier (by Grubbs test) was removed from FIG. 1B. This data point showed no retention for the ΔuvrC mutant replicating the TCAXAGT sequence. As described above, UBP retention in the Golden Gate assembled pINFs used to initiate FIGS. 1A-1E experiments places an upper bound on retention achievable after in vivo replication. Some Golden Gate assembled pINFs preparations showed very low retention. In vivo replication data gathered with these constructs is not presented. Specifically, data was discarded if the Golden Gate assembled pINF's % Shift values were below the following cut-offs for each sequence: GTAXAGA-60%, TCAXAGT-70%, TCGXGGT-55%, TCTXGGT-50%, TCCXCGT-55%, and TCCXGGT-55%.

Example 3. Knockout of IS1 Increases Stability of Nucleoside Triphosphate Transporter PtNTT2

To assess whether deflection of the transposable element, IS1, contributed to increased stability (evidenced by activity) of the nucleoside triphosphate transporter, PtNTT$_2$, during long-term growth, YZ3 and ΔIS1 were serially passaged in triplicate on 2×YT+50 mM KPi+5 ug/mL Chlor (Media) and assayed for PtNTT2 activity (Rad/OD600). Passage 1 was started through inoculation of 700 uL of Media with a glycerol stock stab. Cultures were grown overnight (~15 hrs) to saturation. Cells were diluted 350-fold into 700 uL of fresh media. This was repeated for 6 total passages. Cells were then passaged 4 additional times with the dilution factor increased to 350,000-fold. Assessment of passaged populations PtNTT2 activity demonstrates that the ΔIS1 strain maintains greater PtNTT2 activity during long-term growth, presumably through elimination of the IS1-mediated PtNTT2 deletion pathway. Since the deletion of PtNTT2 contributed to the loss of unnatural base pairs (UBPs), these results suggest that an engineered host cell or semi-synthetic organism lacking in the IS1-mediated PtNTT2 deletion pathway will show increased retention of unnatural base pairs, and thus an increase in the production of polypeptides comprising unnatural amino acids, as well as the nucleic acid molecules encoding them.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the invention and that methods and structures within the scope of these claims and their equivalents be covered thereby.

What is claimed is:

1. An engineered host cell comprising:
   a) a first nucleic acid molecule comprising an unnatural nucleotide;
   b) a second nucleic acid molecule comprising:
      i) a deletion of a gene encoding a transposition-associated protein or transposable element, wherein the transposition-associated protein comprises InsB and/or InsA, wherein the transposable element comprises IS1, wherein the deletion is an N-terminal deletion, a C-terminal deletion, a truncation at both termini, an internal deletion, and/or a deletion of the entire gene; or
      ii) a gene encoding a mutated transposition-associated protein or transposable element, wherein the transposition-associated protein comprises InsB and/or InsA, wherein the transposable element comprises IS1, wherein the mutated transposition-associated protein or transposable element is not expressed, or is expressed at reduced levels; and
   c) a third nucleic acid molecule encoding a modified nucleoside triphosphate transporter that imports unnatural nucleic acids into the cell, wherein the modified nucleoside triphosphate transporter comprises a nucleoside triphosphate transporter from *Phaeodactylum tricornutum* and further comprises an N-terminal truncation, a C-terminal truncation, or a truncation of both termini, wherein the third nucleic acid molecule is incorporated in a genomic sequence of the engineered host cell, or comprises a plasmid encoding the modified nucleoside triphosphate transporter.

2. The engineered host cell of claim 1, wherein the nucleoside triphosphate transporter exhibits increased stability of expression in the engineered host cell relative to expression in an equivalent engineered host cell that does not comprise the second nucleic acid molecule.

3. The engineered host cell of claim 1, wherein the nucleoside triphosphate transporter comprises PtNTT2.

4. The engineered host cell of claim 3, wherein the PtNTT2 is under the control of a promoter selected from a pSC plasmid or a promoter from a lac operon.

5. The engineered host cell of claim 1, further comprising:
   a) a Cas9 polypeptide or variants thereof, and
   b) a single guide RNA (sgRNA) comprising a crRNA-tracrRNA scaffold, wherein the combination of the Cas9 polypeptide or variants thereof and the sgRNA modulates replication of the first nucleic acid molecule comprising the unnatural nucleotide.

6. The engineered host cell of claim 1, wherein the engineered host cell is a prokaryotic cell comprising an *Escherichia coli* cell or an *Escherichia coli* BL21 (DE3) cell.

7. The engineered host cell of claim 1, wherein the unnatural nucleotide comprises an unnatural base selected from the group consisting of:

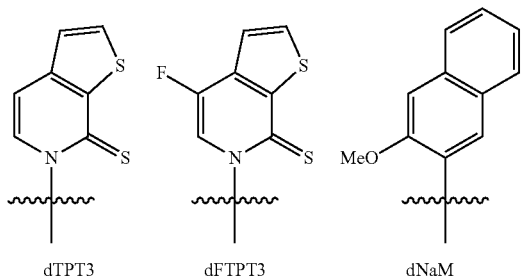

dTPT3    dFTPT3    dNaM

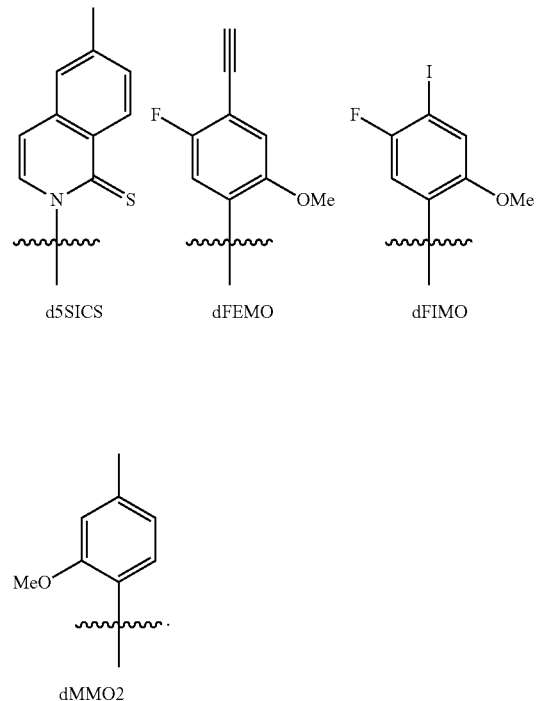

d5SICS    dFEMO    dFIMO dMMO2

8. The engineered host cell of claim 1, wherein the second nucleic acid molecule comprises a deletion of a gene encoding a transposition-associated protein, wherein the transposition-associated protein comprises InsB, or the second nucleic acid comprises a gene encoding a mutated transposition-associated protein, wherein the transposition-associated protein comprises InsB.

9. The engineered host cell of claim 1, wherein the second nucleic acid molecule comprises a deletion of a gene encoding a transposable element, wherein the transposable element comprises IS1.

10. The engineered host cell of claim 1, wherein the second nucleic acid molecule comprises a deletion of a gene encoding a transposition-associated protein, wherein the transposition-associated protein comprises InsB-4, and wherein the deletion comprises an N-terminal deletion, a C-terminal deletion, a truncation at both termini, an internal deletion, and/or a deletion of the entire gene.

11. The engineered host cell of claim 1, further comprising a derepressed polB gene.

12. The engineered host cell of claim 1, wherein the engineered host cell constitutively expresses or overexpresses DNA polymerase II.

13. The engineered host cell of claim 1, wherein the transposition-associated protein comprises InsB-4 and/or InsA-4.

14. The engineered host cell of claim 1, further comprising a deletion of the gene encoding RecA.

* * * * *

SEQUENCE LISTING

```
<160> NUMBER OF SEQ ID NOS: 32

<210> SEQ ID NO 1
<211> LENGTH: 2540
<212> TYPE: DNA
<213> ORGANISM: Escherichia coli

<400> SEQUENCE: 1
aaaccaggct cccccaagcc tggttgtagg ctggagctgc ttcgaagttc ctatactttc      60
tagagaatag gaacttcgaa ctgcaggtcg acggatcccc ggaattttt tataaataca     120 cagccaatca aacgaaacca ggctataatc aagcctggtt ttttgatgga attacagcgt     180
ggcgcaggca ggttttatct taacccgaca ctggcgggac accccgcaag ggacagaagt     240
ctccttctgg ctggcgacgg acaacgggcc gttgcaggtt acgcttgcac cgcaagagtc     300
cgtggcgttt attcccgccg atcaggttcc ccgcgctcag catatttgc agggtgaaca      360 aggcgttcgc ctgacaccgc tggcgttaaa ggatttcac cgccagccgg tgtatggcct      420
```

```
ttactgtcgc gcccatcgcc aattgatgaa ttacgaaaag cgcctgcgtg aaggtggcgt      480
taccgtctac gaggccgatg tgcgcccgcc agaacgctat ctgatggagc ggtttatcac      540
ctcaccggtg tgggtcgagg gtgatatgca caatggcgct atcgttaatg cccgtctgaa      600
accgcatccc gactatcgtc cgccgctcaa gtgggtttct attgatattg aaaccacccg      660
ccacggtgag ctgtactgca tcggcctgga aggctgcggg cagcgcatcg tttatatgct      720
ggggccagag aatggcgacg cctccgcgct cgattttgaa ctggaatacg tcgccagccg      780
cccgcagcta ctggaaaaac tcaacgcctg gtttgccaac tacgatcctg atgtgatcat      840
cggttggaac gtggtgcagt tcgatctgcg aatgctgcaa aaacatgccg agcgttaccg      900
tattccgctg cggctggggc gcgataacag tgagctggag tggcgcgagc acggctttaa      960
aaacggcgtc ttttttgccc aggctaaagg tcggctaatt atcgacggta tcgaggcgct     1020
gaaatccgcg ttctggaatt tctcttcatt ctcgctggaa accgtcgctc aggagttatt     1080
aggcgaagga aaatctatcg ataacccgtg ggatcgaatg gacgaaattg accgccgttt     1140
cgccgaagat aaacctgcgc tggcgactta taacctgaaa gattgcgagc tggtgacgca     1200
gattttccat aaaactgaaa tcatgccatt tttactcgaa cgagcgacgg tgaacggcct     1260
gccggtagac cgccacgggg atcggtggc ggcgtttggt catctctatt ttcctcgtat      1320
gcaccgcgct ggttatgtcg cgcctaatct cggcgaagtg ccgccacacg ccagccctgg     1380
cggctacgtg atggattcac ggccagggct ttatgattcg gtactggtgc tggactataa     1440
aagcctgtac ccgtcgatca tccgcacctt tctgattgat cccgtcgggc tggtggaagg     1500
catggcgcag cctgatccag agcacagtac cgaaggtttt ctcgatgcct ggttctcgcg     1560
agaaaaacat tgcctgccgg agattgtgac taacatctgg cacgggcgcg atgaagccaa     1620
acgccagggt aacaaaccgc tgtcgcaggc gctgaaaatc atcatgaatg ccttttatgg     1680
cgtgctcggc accaccgcct gccgcttctt cgatccgcgg ctggcatcgt cgatcaccat     1740
gcgtggtcat cagatcatgc ggcaaaccaa agcgttgatt gaagcacagg gctacgacgt     1800
tatctacggc gataccgact caacgtttgt ctggctgaaa ggcgcacatt cggaagaaga     1860
agcggcgaaa atcggtcgtg cactggtgca gcacgttaac gcctggtggg cggaaacgct     1920
gcaaaaacaa cggctgacca gcgcattaga actggagtat gaaacccatt tctgccgttt     1980
tctgatgcca accattcgcg gagccgatac cggcagtaaa aagcgttatg ccggactgat     2040
tcaggagggc gacaagcagc ggatggtgtt taaagggctg gaaaccgtgc gcaccgactg     2100
gacgccgctg gcccagcagt ttcagcagga gctatacctg cgcatcttcc gcaacgagcc     2160
atatcaggaa tatgtacgcg aaaccatcga caaactgatg gcgggtgaac tggatgcgcg     2220
actggtttac cgtaaacgcc ttcgccgtcc gctgagcgag tatcagcgta atgtgccgcc     2280
tcatgtacgc gccgctcgcc ttgccgatga agaaaaccaa aagcgtggtc gcccccttgca    2340 atatcagaat cgcggcacca ttaagtacgt atggaccacc aacggcccgg agccgctgga     2400
ctaccaacgt tcaccactgg attacgaaca ctatctgacc cgccagctac aacccgtggc     2460
ggagggaata ctcccttta ttgaggataa ttttgctaca cttatgaccg gcaacttgg      2520 gctatttga gcaaaaaaaa                                                  2540
```

<210> SEQ ID NO 2
<211> LENGTH: 2436
<212> TYPE: DNA
<213> ORGANISM: Escherichia coli

```
<400> SEQUENCE: 2
tgactgtata aaaccacagc caatcaaacg aaaccaggct ataatcaagc ctggtttttt      60
gatggaatta cagcgtggcg caggcaggtt ttatcttaac ccgacactgg cgggacaccc     120
cgcaagggac agaagtctcc ttctggctgg cgacggacaa cgggccgttg caggttacgc     180
ttgcaccgca agagtccgtg gcgtttattc ccgccgatca ggttcccgc gctcagcata      240
ttttgcaggg tgaacaaggc gttcgcctga caccgctggc gttaaaggat tttcaccgcc     300
agccggtgta tggcctttac tgtcgcgccc atcgccaatt gatgaattac gaaaagcgcc     360
tgcgtgaagg tggcgttacc gtctacgagg ccgatgtgcg cccgccagaa cgctatctga     420
tggagcggtt tatcacctca ccggtgtggg tcgagggtga tatgcacaat ggcgctatcg     480
ttaatgcccg tctgaaaccg catcccgact atcgtccgcc gctcaagtgg gtttctattg     540
atattgaaac cacccgccac ggtgagctgt actgcatcgg cctggaaggc tgcgggcagc     600
gcatcgttta tgctggggg ccagagaatg gcgacgcctc cgcgctcgat tttgaactgg      660
aatacgtcgc cagccgcccg cagctactgg aaaaactcaa cgcctggttt gccaactacg     720
atcctgatgt gatcatcggt tggaacgtgg tgcagttcga tctgcgaatg ctgcaaaaac     780
atgccgagcg ttaccgtatt ccgctgcggc tggggcgcga taacagtgag ctggagtggc     840
gcgagcacgg ctttaaaaac ggcgtctttt ttgcccaggc taaaggtcgg ctaattatcg     900
acggtatcga ggcgctgaaa tccgcgttct ggaatttctc ttcattctcg ctggaaaccg     960
tcgctcagga gttattaggc gaaggaaaat ctatcgataa cccgtgggat cgaatggacg    1020
aaattgaccg ccgtttcgcc gaagataaac ctgcgctggc gacttataac ctgaaagatt    1080
gcgagctggt gacgcagatt ttccataaaa ctgaaatcat gccatttta ctcgaacgag     1140
cgacggtgaa cggcctgccg gtagaccgcc acggggatc ggtggcggcg tttggtcatc      1200
tctattttcc tcgtatgcac cgcgctggtt atgtcgcgcc taatctcggc gaagtgccgc    1260
cacacgccag ccctggcggc tacgtgatgg attcacggcc agggctttat gattcggtac    1320
tggtgctgga ctataaaagc ctgtacccgt cgatcatccg caccttctg attgatcccg      1380
tcgggctggt ggaaggcatg gcgcagcctg atccagagca cagtaccgaa ggttttctcg    1440
atgcctggtt ctcgcgagaa aaacattgcc tgccggagat tgtgactaac atctggcacg    1500
ggcgcgatga agccaaacgc cagggtaaca aaccgctgtc gcaggcgctg aaaatcatca    1560
tgaatgcctt ttatggcgtg ctcggcacca ccgcctgccg cttcttcgat ccgcggctgg    1620
catcgtcgat caccatgcgt ggtcatcaga tcatgcggca aaccaaagcg ttgattgaag    1680
cacagggcta cgacgttatc tacggcgata ccgactcaac gtttgtctgg ctgaaaggcg    1740
cacattcgga agaagaagcg gcgaaaatcg gtcgtgcact ggtgcagcac gttaacgcct    1800
ggtgggcgga aacgctgcaa aaacaacggc tgaccagcgc attagaactg gagtatgaaa    1860
cccatttctg ccgttttctg atgccaacca ttcgcggagc cgataccggc agtaaaaagc    1920
gttatgccgg actgattcag gagggcgaca agcagcggat ggtgtttaaa gggctggaaa    1980
ccgtgcgcac cgactggacg ccgctggccc agcagtttca gcaggagcta tacctgcgca    2040
tcttccgcaa cgagccatat caggaatatg tacgcgaaac catcgacaaa ctgatggcgg    2100
gtgaactgga tgcgcgactg gtttaccgta acgccttcg ccgtccgctg agcgagtatc      2160
agcgtaatgt gccgcctcat gtacgcgccg ctcgccttgc cgatgaagaa aaccaaaagc    2220
gtggtcgccc cttgcaatat cagaatcgcg gcaccattaa gtacgtatgg accaccaacg    2280
gcccggagcc gctggactac caacgttcac cactggatta cgaacactat ctgacccgcc    2340
```
agctacaacc cgtggcggag ggaatactcc cttttattga ggataatttt gctacactta    2400
tgaccgggca acttgggcta ttttgagcaa aaaaaa    2436

<210> SEQ ID NO 3
<211> LENGTH: 2008
<212> TYPE: DNA
<213> ORGANISM: Escherichia coli

<400> SEQUENCE: 3
ttattgcacg aagcgcgagg taacgtactg gctgtaatca ttcgctacag ccgggacctt      60
gccctgctct ttcaaaaact gcgcggtgtc gatgatcgct ttgttcaccg gtccggtcag     120
ttctgccgtt tgttgctgcg cgtcagata ggtattcccc ttcaccagcc ccggaacgtc     180
accttcaggc acgccgctta accgcgccag tttgctgatg ttttccggct gtttcagcca     240
cgcgtctggg ttagcaatgt acggttgctg agcatcgatg gcgcttttgg cgaacgcttt     300
caccacctca ggatgtttct cggcaaaatc tttgcgcacc acccagacgt ccagcgttgg     360
cgcaccccac tgcccgacct gttcagaatc ggtcagcact ttgccgtctt tttccagggc     420
gttaaccgcc ggtgcccaga cataagcacc atcaatatct ccccgctgcc atgcagcgat     480
aatcgcgggc ggctgcaggt tcacaatctc cacttgccca ggtttaatgc cccagtgttt     540
cagcgctgcc agcaggctgt agtgggtggt agagataaac ggtacggcga tgcgtttgcc     600
aatcagatct tccggtttgc tgatagtttt ctttaccacc agcgcttctg agttacccag     660
ttttgacgcc agcaagaaga cttcaatcgg cacctgttgg ctggctgcaa ccgctaacgg     720
gctggaacca aggttgccga tttgcacgtc gccagaagcc agcgcccgca cgatgctggc     780
tccgctgtca aacttacgcc agtccacggt tgctccgctt tctttagcaa aggtgttgtc     840
ggcctgagcc actttcgccg gttcggctga ggtttgatac gccacggtga cgttcaccgc     900
ctgtgcctga aaagcgatga atgccagtgc ggcaagaagt gtgtttcgcg atgaaattgc     960
catgattgtc tgctcccctg tcttgttatg ggagcagtat tcaggaataa aaacattcat    1020
taaaagaatt agtcgttatc gcacagatga ttttattctt agcaaaaaaa cggtgatgct    1080
gccaacttac tgatttagtg tatgatggtg ttttgaggt gctccagtgg cttctgtttc    1140
tatcagctgt ccctcctgtt cagctactga cggggtggtg cgtaacggca aaagcaccgc    1200
cggacatcag cgctatctct gctctcactg ccgtaaaaca tggcaactgc agttcactta    1260
caccgcttct caacccggta cgcaccagaa atcattgat atggccatga atggcgttgg    1320
atgccgggca actgccgca ttatgggcgt tggcctcaac acgatttac gtcacttaaa    1380 aaactcaggc cgcagtcggt aacctcgcgc atacagccgg gcagtgacgt catcgtctgc    1440
gcggaaatgg acgaacagtg gggctatgtc ggggctaaat cgcgccagcg ctggctgttt    1500
tacgcgtatg acaggctccg gaagacggtt gttgcgcacg tattcggtga acgcactatg    1560
gcgacgctgg ggcgtcttat gagcctgatg tcacccttg acgtggtgat atggatgacg    1620
gatggctggc cgctgtatga atcccgcctg aagggaaagc tgcacgtaat cagcaagcga    1680
tatacgcagc gaattgagcg gcataacctg aatctgaggc agcacctggc acggctggga    1740
cggaagtcgc tgtcgttctc aaaatcggtg gagctgcatg acaaagtcat cgggcattat    1800
ctgaacataa aacactatca ataagttgga gtcattacca ggccgacaaa atggaggcaa    1860
agaccaacaa agaaaagtag ttaacctagg ctgctgccac cgctgagcaa taagactcct    1920

|  |  |  |  |  |
|---|---|---|---|---|
| gttgatagat | ccagtaatga | cctcagaact | ccatctggat | tgttcagaa cgctcggttg | 1980 |
| ccgccgggcg | ttttttattg | gtgagaat |  |  | 2008 |

<210> SEQ ID NO 4
<211> LENGTH: 17210
<212> TYPE: DNA
<213> ORGANISM: Escherichia coli

<400> SEQUENCE: 4

|  |  |  |  |  |  |
|---|---|---|---|---|---|
| ttattgcacg | aagcgcgagg | taacgtactg | gctgtaatca | ttcgctacag ccgggacctt | 60 |
| gccctgctct | ttcaaaaact | gcgcggtgtc | gatgatcgct | tgttcaccg gtccggtcag | 120 |
| ttctgccgtt | tgttgctgcg | gcgtcagata | ggtattcccc | ttcaccagcc ccggaacgtc | 180 |
| accttcaggc | acgccgctta | accgcgccag | tttgctgatg | ttttccggct gtttcagcca | 240 |
| cgcgtctggg | ttagcaatgt | acggttgctg | agcatcgatg | gcgcttttgg cgaacgcttt | 300 |
| caccacctca | ggatgtttct | cggcaaaatc | tttgcgcacc | acccagacgt ccagcgttgg | 360 |
| cgcaccccac | tgcccgacct | gttcagaatc | ggtcagcact | tgccgtctt tttccagggc | 420 |
| gttaaccgcc | ggtgcccaga | cataagcacc | atcaatatct | ccccgctgcc atgcagcgat | 480 |
| aatcgcgggc | ggctgcaggt | tcacaatctc | cacttgccca | ggtttaatgc cccagtgttt | 540 |
| cagcgctgcc | agcaggctgt | agtgggtggt | agagataaac | ggtacggcga tgcgtttgcc | 600 |
| aatcagatct | tccggtttgc | tgatagtttt | ctttaccacc | agcgcttctg agttacccag | 660 |
| ttttgacgcc | agcaagaaga | cttcaatcgg | cacctgttgg | ctggctgcaa ccgctaacgg | 720 |
| gctggaacca | aggttgccga | tttgcacgtc | gccagaagcc | agcgcccgca cgatgctggc | 780 |
| tccgctgtca | aacttacgcc | agtccacggt | tgctccgctt | tctttagcaa aggtgttgtc | 840 |
| ggcctgagcc | actttcgccg | gttcggctga | ggtttgatac | gccacggtga cgttcaccgc | 900 |
| ctgtgcctga | aaagcgatga | atgccagtgc | ggcaagaagt | gtgtttcgcg atgaaattgc | 960 |
| catgattgtc | tgctcccctg | tcttgttatg | ggagcagtat | tcaggaataa aaacattcat | 1020 |
| taaaagaatt | agtcgttatc | gcacagatga | ttttattctt | agcaaaaaaa ctgtaggctg | 1080 |
| gagctgcttg | aagttcctat | actttctaga | aataggaac | ttcgaactgc aggtcgacgg | 1140 |
| atccccggaa | ttagaacgta | atttacctgc | cggaacttat | tcactccgac aagaacttat | 1200 |
| ccgtacagga | gattaaaatg | ataaaacgga | cgttattagc | ggcggccatt tttagcgcat | 1260 |
| tgcccgctta | tgccgggtta | acttccatta | ccgcgggcta | cgattttacc gattattctg | 1320 |
| gcgatcatgg | caaccgtaat | ttagcgtatg | ctgaactggt | ggcgaaagtt gaaaacgcaa | 1380 |
| cgctgctttt | taatctttcc | caggggcgtc | gtgattatga | aactgaacat ttcaatgcca | 1440 |
| ctcgcggtca | gggtgcggtc | tggtataaat | ggaataactg | gctgacaacc cgaacgggta | 1500 |
| ttgcctttgc | ggataatacg | ccggtctttg | cccgccagga | ttttcgtcag gatattaacc | 1560 |
| tggccctgtt | gccaaaaacg | cttttcacga | ccggttatcg | ctacactaaa tattacgatg | 1620 |
| atgtcgaagt | cgatgcctgg | caaggcggcg | tatcactcta | tactggcccg gtgatcacca | 1680 |
| gctaccgcta | tacccattat | gactccagcg | atgcaggtgg | tagttatagc aatatgattt | 1740 |
| ccgtgcgtct | gaatgacccg | cgcggcactg | gttatacgca | actatggcta agccgcggaa | 1800 |
| caggcgctta | cacctatgac | tggacgccag | aaacacgcta | cggcagcatg aagagcgtca | 1860 |
| gtctgcaacg | tattcaaccg | ctgactgagc | aacttaatct | cggctgacg gcaggtaaag | 1920 |
| tgtggtacga | caccccaacc | gatgattata | acggtctgca | acttgcagcc catctgacct | 1980 |

```
ggaaattctg attccttctg ccgcccgcta tccggggcgg ccttccctgc cgattagccc      2040
ccccctttcc tctttgtttt ccgaccacat tcaccggata aatttttattc tccagtgtta    2100 tatactatag gggggtatgc attgacatat agcatacccc cctatagtat attgcgtgca    2160
gataatgagg tgcgaaatgc ccagtactcc ggaagagaag aaaaaggtcc ttactcgagt    2220
tcgtcgtatt cgagggcaga ttgatgctct ggaacggtcg ctggagggtg atgccgaatg    2280
ccgtgccata ctccaacaga tcgctgccgt tcggggcgcg gctaatgggc tgatggcaga    2340
agtgcttgaa agccatatcc gggaaacgtt tgaccgaaat gactgctaca gccgcgaagt    2400
cagccaatcc gttgacgaca ctattgaact ggttcgagcc tatcttaaat agctgaatct    2460
attaccatat tgaggaagag cgagagatga aatcacgtgc tgccgttgca tttgctcccg    2520
gtaaaccgct ggaaatcgtt gaaattgacg ttgcaccacc gaaaaaaggt gaagtgctga    2580
ttaaagtcac ccataccggc gtttgccata ccgacgcatt taccctctcc ggggatgacc    2640
cggaaggtgt attcccggtg gttctcggtc acgaagggc cggcgttgtg gttgaagtcg    2700
gtgaaggcgt aaccagcgtc aaacctggcg accatgtgat cccgctttac accgcggagt    2760
gcggcgagtg tgagttctgt cgttctggca aaactaacct ctgtgttgcg gttcgcgaaa    2820
cccagggtaa aggcttgatg ccagacggca ccacccgttt ttcttacaac gggcagccgc    2880
tttatcacta catgggatgc tcaacattca gtgaatacac cgtggtcgcg gaagtgtctc    2940
tggccaaaat taatccagaa gcaaaccatg aacacgtctg cctgctgggc tgtggcgtga    3000
ccaccggtat tggcgcggtg cacaacacag ctaaagtcca gccaggtgat tctgttgccg    3060
tgtttggtct tggcgcgatt ggtctggcag tggttcaggg cgcgcgtcag gcgaaagcgg    3120
gacggattat cgctatcgat accaacccga agaaattcga tctggctcgt cgcttcggtg    3180
ctaccgactg cattaacccg aatgactacg acaaaccgat taaagatgtc ctgctggata    3240
tcaacaaatg gggtatcgac catacctttg aatgcatcgg taacgtcaac gtgatgcgtg    3300
cggcgctgga aagtgcgcac cgcggctggg gtcagtcggt gatcatcggg gtagcaggtg    3360
ccggtcagga atctccaccc gaccattcc agttggtcac cggtcgcgta tggaaaggtt    3420 ccgcgttttgg cggcgtgaaa ggtcgttccc agttaccggg tatggttgaa gatgcgatga    3480 aggtgatat cgatctggaa ccgtttgtca cgcataccat gagccttgat gaaattaatg    3540
acgccttcga cctgatgcat gaaggcaaat ccattcgaac cgtaattcgt tactgatttc    3600
ccgcaggtat accccgtcca cttcagacgg ggttcttaat actctccctg ggcagccgtc    3660
cgggggatta accgtgagat aatgactgat ggaactcatt gaaaaacatg ccagctttgg    3720
cggctggcaa aatgtgtatc ggcattattc ccaatcactg aaatgtgaaa tgaatgtcgg    3780
cgtctatctc ccaccaaaag ccgcgaatga aaaattgccg gtgttgtact ggctttcagg    3840
cctgacttgc aacgagcaga atttcattac taaatcgggg atgcagcgtt acgcggctga    3900
gcacaacatt attgttgttg cgccggacac cagtccgcga ggcagtcatg tcgcagatgc    3960
tgaccgttac gatctcgggc aaggtgccgg gttttacctg aacgcgacgc aagcgccgtg    4020
gaatgaacat tacaaaatgt atgactatat ccgcaacgag ctgccggatt tagtgatgca    4080
tcattttccg gcaacggcca aaagtctat ctctggtcat tctatgggcg ggctgggcgc    4140
gctggtgctg gcgttacgta acccagatga atatgtcagc gtctcggcgt tttcgcccat    4200
tgtctcccca tcgcaagtgc cgtggggaca gcaagccttt gctgcatatc ttgctgaaaa    4260
taaagatgcc tggttggatt acgacccggt gagtcttatt tcacaaggtc aacgcgttgc    4320
ggaaatcatg gttgatcagg ggttgagtga tgatttttac gcagaacagc tgcggactcc    4380
```

| | | | | | |
|---|---|---|---|---|---|
| aaatcttgaa | aagatctgcc | aggagatgaa | tatcaagacg | ttaatccgtt | atcacgaggg | 4440 |
| ttatgatcac | agctattatt | ttgtctccag | ttttattggc | gagcatattg | cctaccacgc | 4500 |
| caataaactg | aatatgcgtt | gataatagtg | cacgactgcc | ggatgcggcg | tgaacgcctt | 4560 |
| atccggccta | cacttcgccc | gtaaaccgta | ggcctgataa | gacgcgcaaa | gcgtcgcatc | 4620 |
| aggcatggcg | cacgactgcc | ggatgcggcg | tgaacgcctt | atccggtcta | cacttcgccc | 4680 |
| ataaaccgta | ggcctgataa | gacgcgcata | gcgtcgcatc | aggcatctgc | gcacgactta | 4740 |
| tctatgttta | ccacatcaaa | tcatcaggca | ctttgaagtc | ggcatacggg | tcgtcttcat | 4800 |
| cctgctcttc | ggcgctgagc | gcgctgtgca | acactatact | gctggcatcg | cgctgagcaa | 4860 |
| ttttatcggc | aacgctggcg | ggaataatgg | cgtattcacc | ttcgctattg | ttatcgacca | 4920 |
| acaagcgggc | aatcgccaga | cgaccattaa | tcaactgcgc | ctgtgtgagc | ttatcgacaa | 4980 |
| aaatcttctt | aatcagattg | ccgtcagtga | agttaaaacc | aatatcgcca | ttggcaatgg | 5040 |
| tgattcggtt | catttcaata | agctgcttca | cctgagcttt | atattctttc | gccaacgccg | 5100 |
| cttgtttttg | ctgttcgcta | agctgtttat | cacgctcaag | ctgtgccttt | ttattttctt | 5160 |
| ctaccgccgc | ccgagcttca | cgcgcctgaa | cgcgcgattt | tttcgccgtt | ctctccacct | 5220 |
| tcgccgcttt | tttgctggtg | actaatcctg | ctttgagcaa | ctgctcttgt | aaggtaagtt | 5280 |
| ttgccatctt | tgtttccaaa | cccgctgaat | aatttttagc | gagtatacct | gtaaacgccg | 5340 |
| taggtgtatt | ggggtgaagt | cccttcgcc | cctgcctaat | aaggcacgtc | aggcatcggc | 5400 |
| gcacggctgt | attcgtgatc | tccggctcat | caaaataaac | accgccaacc | cagcaacaag | 5460 |
| aatacccggt | gcagaagcgg | ccattacgcc | gaccgtgcca | gtgcctaatg | ccagcatttt | 5520 |
| cccggccagt | aacggaccgc | tcatagcccc | cagacgccct | accgcacgg | ctgttcccac | 5580 |
| acctgttgcg | cggatctgcg | aactgtaaaa | caacggtgcc | agggcataca | aaacgctttg | 5640 |
| cccacctgtc | gcaaacaacc | ccgcgacaaa | tcccgccagc | aacataccgt | taaatgacga | 5700 |
| caccgttcca | agcgccagca | gcgaagctaa | catgccgcta | taaatcagta | gcgacatggt | 5760 |
| tactggacgc | agcttatcca | tcaatgcgcc | caacattaac | gtcccgcttg | ccgcccccat | 5820 |
| ttgcagggca | aacatcaccc | ctgccgcctg | cgatggctgg | aatccttgct | ccaccaaaag | 5880 |
| tagcggtagc | cagttgatca | acatgtagac | caccagcaga | gtgaagaaat | aacacaacca | 5940 |
| cagcagcagc | gtcgcggttg | ccgtttctgg | cgcaaataag | gcacgcagtg | gtggcgcaga | 6000 |
| ctgttttcg | ccagcgaaaa | ccgccgactc | cggcagccag | cgcattaata | gcggcaccag | 6060 |
| aatcaacggc | accacaccac | ctacccaaaa | caccgtttgc | catgctaagt | ttgccccgc | 6120 |
| gaaacccagt | gtcgccgcca | gcgccgcgcc | aatgggaaca | ccgcaataca | tcaggctcac | 6180 |
| tgccgtccca | cgaaaacgtg | gacccgcggc | ttcagacgtc | agggcgataa | gattcggcaa | 6240 |
| cgccgccccc | agcccgacac | cggtcatcag | ccgcgcaaag | accagtgagg | gaaatcccca | 6300 |
| ggcaatcgcc | gttgccagtg | agaacaaacc | aaacagcgca | actgagccaa | tcaaaatacg | 6360 |
| cttacgacca | taacggtccg | ccagcattcc | gccaaccaac | gcgccgggta | gcaaaccgag | 6420 |
| tattccggcg | ctaaatatcc | agcccatttg | catttatcg | agtgcgaaag | cctgggcgat | 6480 |
| gccacccgcc | gcaatgccag | ccgcctgaag | atccagcccc | tccatcagag | cgaccaaaaa | 6540 |
| acaaagcccg | atggtcagca | tcaggcggga | tgaagatgat | gaaggggtac | gagtcgacat | 6600 |
| aagatgaacc | tcattgcgag | tgcaggtgaa | tcgcgactga | tacattgcca | gccgcgtaat | 6660 |
| cagaactatt | gaatgactgc | ctacgggcga | aatgtaggcc | ggataaggcg | ttcacgccgc | 6720 |

```
atccggcagt cgtgtgcaga tgcctgatgc gacgcttgcg cgtcttatca ggcctacaaa    6780
ttcccgcgcc atccgtaggc cggataaggc gtttacgccg catccggcag tcgtgcgcag    6840
atgcctgatg cgacgctaac gcgtcttatc aggcctacaa attctcgcgc catccgtagg    6900
ccggacaaga cgttcacgcc gcatccggca gtcgtgctgg gatgggcata caaaatgcac    6960
attctcggca gtcaatatta tttgttgttg cgcagatcca gcgccacgtc gacgatcata    7020
tcctcctggc cgccaaccat ccggcgtttg cccagctcaa cgagaatatc caccgcgctt    7080
aagccataac gcgccgccgc cgtttcacag tgacgcagga agctggagta acaccagcg     7140
tatcccagcg ccagcgtttc gcgatcgact cgtaccggtc gatcctgcaa cggacgcacc    7200
aggtcgtcag cggcatccat taacgcatag agatcggtcc catgctgcca gcccagttta    7260
tccgcggcgg caataaatac ttccagcggc gcgttacctg cgcccgcgcc cattcccgcg    7320
aggctggcgt cgattcggtc gcagccctct tccaccgcct cgatagagtt cgccacgcca    7380
agactcaggt tatggtgagc gtgcatgccg gtttgcgttt ctggtttcaa cactgctttc    7440
agggcgcgga aacggtcacg gatatcgctc atgttcatcg caccgccaga atccaccaca    7500
taaatacagg tcgcaccgta gccttccatc agctttgcct gctttgcgag attctctggc    7560
gtggtcatat ggctcatcat cagaaaacca acggtgtcca ttccgagctc gcgggcatac    7620
tgaatatgct gggcggaaac atcagcttcg gtacagtgcg tagccacacg aaccacccgc    7680
gcgccagctt gccaggcatt tttcagatcg tgaatagtgc cgattcctgg cagcaacaac    7740
gtcgcgattt tggcgtgctt caccacatcc gccgctgctt caatccattc aaggtcgcta    7800
tgtgcgccga aaccatagtt aaagctggaa ccctgcaaac cgtcgccgtg ggccacttca    7860
atcgaatcca cgtgggcatc gtccagtgct ttggcaatct ggcgaacgtt ttccagcgaa    7920
tactgatgac gaatggcgtg cataccgtca cgcaacgtga cgtccgagat ataaagtttt    7980
ttaccgttca tgccgcttct cctgccttgc gcgccagtga ctgggccatt ttttccgctg    8040
tcgccagcgc actggaagtc ataatgtcga ggttgcccgc ataggcaggc agataatgcg    8100
ctgcgccttc gacttccagc cagaccgctg ttttcagtcc ggagaattgc cccacgcccg    8160
gtaaattgac cggtttatcc tgcgggataa cttcaaactg cacgcgctgt ttcaggcgat    8220
aacccggtac gtaagcctgc accgcctcag ccatttcatt gattgaggct cgatatcat    8280
cttgtgaagc ttcgtcgctc aatacataca ccgtgtcacg catcatcaac ggtggctctg    8340
ctgggttaag cacaataatc gccttcccct ttgccgcgcc gcccaccact tcaatggctc    8400
gggaagtggt ttccgtaaat tcatcgatat tggcacgcgt gccaggtccg gcagatttac    8460
tggcgataga agcgataatt tcggcgtaat gaacacgcgc cacgcgtgaa actgccgcca    8520
ccattggaat ggtggcctgg ccgccgcagg tgaccatgtt gacgttcagt tgatcgacgt    8580
tcgcctcgag gttaaccacc ggcacgcagt aagggccgat ggcagcaggc gtcaggtcaa    8640
ttaagcgaat atccggtttc gcttcgcgta aagcggcatc gttttcaca tgagcaccgg     8700
cgctggtcgc atcaaataca atgtcgatat cagcaaattc aggcatgttc atcagtccga    8760
tcacccctttc atgggtggtg gcgacgccca tacgtctggc gcgcgccaga ccgtcggact    8820
gaggatcaat gccaaccatc accgccatct ccagatgctg accgtgacgc aaaattttaa    8880
tcatcagatc ggtgccaatg ttgccagaac cgataatggc gactttacgc ttactcatga    8940
cagacttcct tttggggctg cgcttgaaaa tgtcgcagca actgaaccta tgccttcaat    9000
atgggcttca aaacgatcgc ccgcattcac cgccaccatc ggacctaatg ccccggtaag    9060
aatgatatct ccggtgcgca gcggttcacc cagactggcc attttgcgtg ccagccagac    9120
```

```
ggccgcatta agcggatgtc ccaggcattc gctgccgcgc ccgctagaaa cctcttcgtt    9180
attacgcgtc atcttcatgg cgcagttttt caggtctaac cccgccggac gttgcgccgg    9240
accgccgatg acatacaccc cacaggaggc gttatctgcc acggtatcga caaactgaat    9300
cgaccagtcg cgaatgcggc tccccaccac ttcagcgcc ggaagtaccc attcaatggc     9360
gttatacaat tcgtcgaagg tgatatcggt tgcgggcaaa tcgcggttca acaccagtgc    9420
gatctccgct tcaatgcggg gttgcagaac acgggaaaaa ggaatgattt cgttatcgcc    9480
ataacacatg tcggcaaata atgtcccgaa atccggttga tcaacgccca gttgttgctg    9540
cactttcgga tgcgtcaggc ccactttacg ccctaccacg cgacgcccct gcgcaacgtc    9600
atattgcaca tttatgtgct gaatggcgta ggccgcttca gcgttatcga taccaatcag    9660
atcgcgcagc ggcgcaatcg cttcgccctg ctctgcggcg cggcgtaaat ccgccgccag    9720
ttgctcaaga gtatgcttcg tcatgaccat tccttaaggg cgtgcgagga aattcagcac    9780
caattgattg aaagcgtcgg catgttccca ctgcgcccag tgaccacagt cgcggaagat    9840
atgcagttca gaaccggcaa tgccggacag cagacgcaga cccgcatcca tcggcacaaa    9900
gcggtcgttg cgcccccaga caatcagggt ttgcgctttg atttccgcca gacgtgggcc    9960
aaaatccggg aactgtttcg gattagcttc caggctctta acgaagtttt ccaggtgatc    10020
gcggcgcgac agcatattat tcaggcgcgc ttcaaacagg cgtcggtca aatcgctggt     10080 atcgaaaacg aagatatcca tcatcagctt caggttttcg atagtcggct gacgataaag    10140
ctgattcagt cgcttaatac cttcggttgg catcggcgta acaaactca tgccgcccgt     10200 accgccgccc atcagcacca gtttgccgac gcgctccggc cagttaaggg tgaacgccac    10260
agaactatgg ccgcccatcg agttgcccag caggtggatt ttggcgatat ccagttgatc    10320
caccacgctt ttcaggattc gtgcattaag atccgatcgt gaaccactat taacgatcga    10380
atcgcttttg ccccaacccg gacaatccag caggatcacc cgatagcccg cctctaccag    10440
cggatcgata ttgcggctga agttcgccca gccagtagca cccgggccgg aaccatgcag    10500
caggacaacg gtttcgtcgc cttgtccgca gtcattaaaa tggatgcgca gcgttttacc    10560
cgcttcttct acattcagaa aacggctggt ggcggcttcg gtttgtggct gataactcat    10620
catcttctcc tgcatattca gttctctgtt ctggcgctta acgagccaaa tccggcaatc    10680
cactccggga ttgggcggta ataacgcct tcgctacgcc agttgccaaa tgcagaaata     10740
gcggcaaaag cggcgaccca ggttttgatt tcatgtgtcg actttccggc aatggcggaa    10800
agctcttcgt tactgacggc atccagttcc tgtatgcgtc cctgctccag caaagtcatg    10860
aactggttat cccaaatcgg gttgagcgga tgcagagttc tctgatcctc aacaaacttc    10920
tcagcggcgc taatcacccg ttgctgacgc aattcgcgct cactggcggg taaatctttc    10980
ccgctcccca acagacggtc gcgcatatgg gcatcggctt cgccagttc gggcaccggc     11040 ggctgatggg aaagcccacc ggaacccagg aacagcacgc gtttattgag agtgctggtg    11100
aaacgtccaa tggcttcacc caacatgcgg gtacgctgga aaccgggcag cggcgtggcg    11160
acaccgttga tgaacacagg cagaactggc accttatcca gcccgccgag caggaactcc    11220
agtggctggg cgaacccgtg gtccacctgc atacagtaag aaacggcaag atcgatcccg    11280
ctcttcatga cggcatgcgc acaggcctcc gccagctcca caggcacggg cagctctcct    11340
gccgcactgc cgaaatcacc aattgccgtc gccccaacgc ctaaacagaa cggtggcatc    11400
acgtcataga aaaagccgtt gtagtgatct ggcgcaaaca gcaccaccag ttcaggggag    11460
```

```
aaagccgcaa tacgctcgcg ggcgctggca atcacgccat tgacctcatc gagtacctct    11520
tgcgccgggt cgacatatcc caccagcggc gagtgggaaa gacagtgaag ataagcgtgc    11580
atatcaggct accttttcga cagaaacgtc ggcatcaggg cgggtcagcg tcatcaccga    11640
cgccagttta ttcagcgtat tacccagggt ttgcggaatg gcggtggcgg caacaaagcg    11700
atccgggcgc atcaccacca gcgaagcatt atgttgtgcg aaccagctac gcaggcgacc    11760
ttgcgtatcc cccacgcgta gtacgccgtc gtggttatcc tgtgcggtat gaatttgcac    11820
ttccggcacc acctgaatga agcgggtgcc caacgcgcgc cactgctgga tttgctcgtc    11880
gctcatcccc cacagtggat tgcatcccca gccaattacc gcgaagttcg cgccgatcgc    11940
gttatcgagc agcgtcacgt cgccgttttc cagcgtgact ttcggctgaa taaacatctt    12000
gccgaccgga gagtgcttcg cttcgccctc tcgcaccagc gcaccgccgt aatattgcgg    12060
catcggcttg aagcgcattt cgaggaagta gcgttttact ggcggcagat aattcaacag    12120
ccaggaaacg ccgtcacgta acgtaccctg ccagcgtttc ggcggagcca gcacgttgcc    12180
cgccgtcacg gacaggtcaa tcatcgcttt ggcgtgatcg cgtcgttctt gttgataggt    12240
atcgagcagc gcatcacggg cttteccctg gataaccaac gccagtttcc aggcgaggtt    12300
aaaggcgtcg cgcataccgc tgttatagcc ctgcccctgc cataccggca tgatgtgcgc    12360
ggcatcgccc gccagcagta cgcgatcaat acggaaacgt tgcgccagtc gcgcgttgtg    12420
ggtgtagaca cgctggcgaa tcaattcaac attgtccgga ttaggcagca cttttgcttaa   12480 cagcttgcgc atatttttgcg gctcacgcag ctgttcttcg gtttctcctg gcatcaccat    12540
aaattcaaag cgacgtaccg catgaggtag cgcggcagaa acatacgggc gcaccggatc    12600
gcaacacaaa tagatatgcg gcgtacttaa cggatcgttg gcgatatcta ccacaatcca    12660
ctgatttggc gcagttttac cttcaaacgg cacattcagg gtgcgacgga caaaacttgc    12720
cccaccatca caggccacca gccactgggc tttgactatt tcccgctgcc cttctgccgt    12780
tttcaggtgc aaggtcactt cgtcatcttg ctgactgaag gcctccagct cgcgggaaaa    12840
caagcagcgc acattcggaa aacgcgacac cccttccagc atcaccgcat cgacctgcgg    12900
ctgaataaag gcgttacggc gcggccagcc aaattcatcg gtcattggct gaatatcagc    12960
aaaacagcgg ccttttcgggg tgagaaaacg catcgcgtgc cacggcgtag tgtgcggcag    13020
aacatcatcg accaggccga ccgactgcat ggtgcgcagc gcctcgtcat caataccaat    13080
cgcacgcggg tagtcgatca acttatcgag tttctccacc accagcacgt caatgcccat    13140
ctggccgaga tagttcgcca tcatcagccc aaccgggccg gcaccagcga tcgccacctg    13200
aacgctatgg ttaacagcag gctggatgtc agggtgttgt attgccatt cagtacctca    13260 cgactcggac aaaatgtcgt tgcgcgcaca gtacagcgca acttattttg ttaaaaacat    13320
gtaaatgatt ttttattgtg cgctcagtat aggaagggtg ttttcggcta caatcaaaac    13380
atgcccgaat gtgcaccagg tgcaccacgt tgttttaact atagaaatgt caattaatat    13440
gcagaacaat gagcagacgg aatacaaaac cgtgcgcggc ttaacccgcg gtctaatgtt    13500
attaaatatg ttaaataaac ttgatggcgg tgccagcgtc gggctgctgg cggaactcag    13560
cggcctgcat cgcaccactg tgcggcgact gctggagacg ctgcaggaag agggatatgt    13620
ccgccgtagc ccctccgatg atagttttcg actgaccatc aaagtgcggc aattaagcga    13680
aggatttcgt gacgaacagt ggatttctgc actggcggcc ccactgctgg gcgatctgtt    13740
gcgcgaagtg gtatggccga cagatgtgtc cacgctggat gttgatgcaa tggtggtacg    13800
cgaaaccact caccgtttca gccgcttatc cttcaccgg gcaatggtcg ggcgacgttt    13860
```

```
gccgcttctg aaaaccgcct cgggcctgac ctggctggcc ttttgcccgg aacaagaccg    13920
caaggaatta atcgaaatgt tagcctcccg ccccggtgat gactatcaac tggcacggga    13980
accgttaaag ctggaagcca ttctggcgcg cgcgcgcaaa gagggttacg gacagaacta    14040
ccgcggctgg gatcaggagg agaagatcgc ctctatcgcc gtaccgctgc gcagtgaaca    14100
acgggtgatt ggctgtctga atctggtgta tatggcgagc gcaatgacca ttgaacaggc    14160
agcggaaaag catcttccgg cgctacaacg ggtagcaaaa cagatcgaag aagggggttga   14220 atcgcaggct attctggtgg ccggaaggcg aagcggcatg catttacgtt gacaccatcg    14280
aatggcgcaa aacctttcgc ggtatggcat gatagcgccc ggaagagagt caattcaggg    14340
tggtgaatgt gaaaccagta acgttatacg atgtcgcaga gtatgccggt gtctcttatc    14400
agaccgtttc ccgcgtggtg aaccaggcca gccacgtttc tgcgaaaacg cgggaaaaag    14460
tggaagcggc gatggcggag ctgaattaca ttcccaaccg cgtggcacaa caactggcgg    14520
gcaaacagtc gttgctgatt ggcgttgcca cctccagtct ggccctgcac gcgccgtcgc    14580
aaattgtcgc ggcgattaaa tctcgcgccg atcaactggg tgccagcgtg gtggtgtcga    14640
tggtagaacg aagcggcgtc gaagcctgta agcggcggt gcacaatctt ctcgcgcaac    14700
gcgtcagtgg gctgatcatt aactatccgc tggatgacca ggatgccatt gctgtggaag    14760
ctgcctgcac taatgttccg gcgttatttc ttgatgtctc tgaccagaca cccatcaaca    14820
gtattatttt ctcccatgaa gacggtacgc gactgggcgt ggagcatctg gtcgcattgg    14880
gtcaccagca aatcgcgctg ttagcgggcc cattaagttc tgtctcggcg cgtctgcgtc    14940
tggctggctg gcataaatat ctcactcgca atcaaattca gccgatagcg gaacgggaag    15000
gcgactggag tgccatgtcc ggttttcaac aaaccatgca aatgctgaat gagggcatcg    15060
ttcccactgc gatgctggtt gccaacgatc agatggcgct gggcgcaatg cgcgccatta    15120
ccgagtccgg gctgcgcgtt ggtgcggata tctcggtagt gggatacgac gataccgaag    15180
acagctcatg ttatatcccg ccgttaacca ccatcaaaca ggattttcgc ctgctggggc    15240
aaaccagcgt ggaccgcttg ctgcaactct ctcagggcca ggcggtgaag gcaatcagc    15300 tgttgcccgt ctcactggtg aaaagaaaaa ccaccctggc gcccaatacg caaaccgcct    15360
ctccccgcgc gttggccgat tcattaatgc agctggcacg acaggtttcc cgactggaaa    15420
gcgggcagtg agcgcaacgc aattaatgta actaggcacc ccaggcttta cactttatgc    15480
ttccggctgg tataatgtgt ggacctgtag aaataatttt gtttaacttt aataaggaga    15540
tataccatgg gaggcagtac tgttgcacca actacaccgt tggcaaccgg cggtgcgctc    15600
cgcaaagtgc gacaagccgt ctttcccatc tacggaaacc aagaagtcac caaatttctg    15660
ctcatcggat ccattaaatt ctttataatc ttggcactca cgctcacgcg tgataccaag    15720
gacacgttga ttgtcacgca atgtggtgcc gaagcgattg cctttctcaa aatatacggg    15780
gtgctacccg cagcgaccgc atttatcgcg ctctattcca aaatgtccaa cgccatgggc    15840
aaaaaaatgc tattttattc cacttgcatt cctttctta cctttttcgg gctgtttgat    15900
gttttcattt acccgaacgc ggagcgactg caccctagtt tggaagccgt gcaggcaatt    15960
ctcccgggcg gtgccgcatc tggcggcatg gcggttctgg ccaagattgc gacacactgg    16020
acatcggcct tattttacgt catggcggaa atatattctt ccgtatcggt ggggctattg    16080
ttttggcagt ttgcgaacga cgtcgtcaac gtggatcagg ccaagcgctt ttatccatta    16140
tttgctcaaa tgagtggcct cgctccagtt ttagcgggcc agtatgtggt acggtttgcc    16200
```

-continued

| | |
|---|---|
| agcaaagcgg tcaactttga ggcatccatg catcgactca cggcggccgt aacatttgct | 16260 |
| ggtattatga tttgcatctt ttaccaactc agttcgtcat atgtggagcg aacggaatca | 16320 |
| gcaaagccag cggcagataa cgagcagtct atcaaaccga aaagaagaa acccaaaatg | 16380 |
| tccatggttg aatcggggaa atttctcgcg tcaagtcagt acctgcgtct aattgccatg | 16440 |
| ctggtgctgg gatacggcct cagtattaac tttaccgaaa tcatgtggaa aagcttggtg | 16500 |
| aagaaacaat atccagaccc gctagattat caacgattta tgggtaactt ctcgtcagcg | 16560 |
| gttggtttga gcacatgcat tgttattttc ttcggtgtgc acgtgatccg tttgttgggg | 16620 |
| tggaaagtcg gagcgttggc tacacctggg atcatggcca ttctagcgtt acccttttt | 16680 |
| gcttgcattt tgttgggttt ggatagtcca gcacgattgg gatcgccgt aatctttgga | 16740 |
| acaattcaga gtttgctgag caaaacctcc aagtatgccc ttttcgaccc taccacacaa | 16800 |
| atggcttata ttcctctgga cgacgaatca aaggtcaaag gaaaagcggc aattgatgtt | 16860 |
| ttgggatcgc ggattggcaa gagtggaggc tcactgatcc agcagggctt ggtctttgtt | 16920 |
| tttgaaaata tcattaatgc cgcacctgta gtaggggttg tctactacag tgtccttgtt | 16980 |
| gcgtggatga gcgcagctgg ccgactaagt gggcttttc aagcacaaac agaaatggat | 17040 |
| aaggccgaca aaatggaggc aaagaccaac aaagaaaagt agttaaccta ggctgctgcc | 17100 |
| accgctgagc aataagactc ctgttgatag atccagtaat gacctcagaa ctccatctgg | 17160 |
| atttgttcag aacgctcggt tgccgccggg cgttttttat tggtgagaat | 17210 |

<210> SEQ ID NO 5
<211> LENGTH: 17898
<212> TYPE: DNA
<213> ORGANISM: Escherichia coli

<400> SEQUENCE: 5

| | |
|---|---|
| ttattgcacg aagcgcgagg taacgtactg gctgtaatca ttcgctacag ccgggacctt | 60 |
| gccctgctct ttcaaaaact gcgcggtgtc gatgatcgct tgttcaccg gtccggtcag | 120 |
| ttctgccgtt tgttgctgcg cgtcagata ggtattcccc ttcaccagcc ccggaacgtc | 180 |
| accttcaggc acgccgctta accgcgccag tttgctgatg ttttccggct gtttcagcca | 240 |
| cgcgtctggg ttagcaatgt acggttgctg agcatcgatg gcgcttttgg cgaacgcttt | 300 |
| caccaccctca ggatgtttct cggcaaaatc tttgcgcacc acccagacgt ccagcgttgg | 360 |
| cgcaccccac tgcccgacct gttcagaatc ggtcagcact ttgccgtctt tttccagggc | 420 |
| gttaaccgcc ggtgcccaga cataagcacc atcaatatct ccccgctgcc atgcagcgat | 480 |
| aatcgcgggc ggctgcaggt tcacaatctc cacttgccca ggtttaatgc cccagtgttt | 540 |
| cagcgctgcc agcaggctgt agtgggtggt agagataaac ggtacggcga tgcgtttgcc | 600 |
| aatcagatct tccggtttgc tgatagtttt ctttaccacc agcgcttctg agttacccag | 660 |
| ttttgacgcc agcaagaaga cttcaatcgg cacctgttgg ctggctgcaa ccgctaacgg | 720 |
| gctggaacca aggttgccga tttgcacgtc gccagaagcc agcgcccgca cgatgctggc | 780 |
| tccgctgtca aacttacgcc agtccacggt tgctccgctt tctttagcaa aggtgttgtc | 840 |
| ggcctgagcc actttcgccg gttcggctga ggtttgatac gccacggtga cgttcaccgc | 900 |
| ctgtgcctga aaagcgatga atgccagtgc ggcaagaagt gtgtttcgcg atgaaattgc | 960 |
| catgattgtc tgctcccctg tcttgttatg ggagcagtat tcaggaataa aaacattcat | 1020 |
| taaaagaatt agtcgttatc gcacagatga ttttattctt agcaaaaaaa cggtgatgct | 1080 |
| gccaacttac tgatttagtg tatgatggtg ttttgaggt gctccagtgg cttctgtttc | 1140 |

```
tatcagctgt ccctcctgtt cagctactga cggggtggtg cgtaacggca aaagcaccgc    1200
cggacatcag cgctatctct gctctcactg ccgtaaaaca tggcaactgc agttcactta    1260
caccgcttct caacccggta cgcaccagaa atcattgat atggccatga atggcgttgg    1320
atgccgggca actgcccgca ttatgggcgt tggcctcaac acgatttta cgtcacttaaa    1380 aaactcaggc cgcagtcggt aacctcgcgc atacagccgg gcagtgacgt catcgtctgc    1440
gcggaaatgg acgaacagtg gggctatgtc ggggctaaat cgcgccagcg ctggctgttt    1500
tacgcgtatg acaggctccg gaagacggtt gttgcgcacg tattcggtga acgcactatg    1560
gcgacgctgg ggcgtcttat gagcctgatg tcacccttg acgtggtgat atggatgacg    1620
gatggctggc cgctgtatga atcccgcctg aagggaaagc tgcacgtaat cagcaagcga    1680
tatacgcagc gaattgagcg gcataacctg aatctgaggc agcacctggc acggctggga    1740
cggaagtcgc tgtcgttctc aaaatcggtg gagctgcatg acaaagtcat cgggcattat    1800
ctgaacataa aacactatca ataagttgga gtcattacct agaacgtaat ttacctgccg    1860
gaacttattc actccgacaa gaacttatcc gtacaggaga ttaaaatgat aaaacggacg    1920
ttattagcgg cggccatttt tagcgcattg cccgcttatg ccgggttaac ttccattacc    1980
gcgggctacg atttaccga ttattctggc gatcatggca accgtaattt agcgtatgct    2040
gaactggtgg cgaaagttga aaacgcaacg ctgcttttta atctttccca ggggcgtcgt    2100
gattatgaaa ctgaacattt caatgccact cgcggtcagg gtgcggtctg gtataaatgg    2160
aataactggc tgacaacccg aacgggtatt gcctttgcgg ataatacgcc ggtctttgcc    2220
cgccaggatt ttcgtcagga tattaacctg gccctgttgc caaaaacgct tttcacgacc    2280
ggttatcgct acactaaata ttacgatgat gtcgaagtcg atgcctggca aggcggcgta    2340
tcactctata ctggcccggt gatcaccagc taccgctata cccattatga ctccagcgat    2400
gcaggtggta gttatagcaa tatgatttcc gtgcgtctga atgacccgcg cggcactggt    2460
tatacgcaac tatggctaag ccgcggaaca ggcgcttaca cctatgactg gacgccagaa    2520
acacgctacg gcagcatgaa gagcgtcagt ctgcaacgta ttcaaccgct gactgagcaa    2580
cttaatctcg ggctgacggc aggtaaagtg tggtacgaca ccccaaccga tgattataac    2640
ggtctgcaac ttgcagccca tctgacctgg aaattctgat tccttctgcc gcccgctatc    2700
cggggcggcc ttccctgccg attagccccc ccctttcctc tttgttttcc gaccacattc    2760
accggataaa ttttattctc cagtgttata tactataggg gggtatgcat tgacatatag    2820
catacccccc tatagtatat tgcgtgcaga taatgaggtg cgaaatgccc agtactccgg    2880
aagagaagaa aaaggtcctt actcgagttc gtcgtattcg agggcagatt gatgctctgg    2940
aacggtcgct ggagggtgat gccgaatgcc gtgccatact ccaacagatc gctgccgttc    3000
ggggcgcggc taatgggctg atggcagaag tgcttgaaag ccatatccgg gaaacgtttg    3060
accgaaatga ctgctacagc cgcgaagtca gccaatccgt tgacgacact attgaactgg    3120
ttcgagccta tcttaaatag ctgaatctat taccatattg aggaagagcg agagatgaaa    3180
tcacgtgctg ccgttgcatt tgctcccggt aaaccgctgg aaatcgttga aattgacgtt    3240
gcaccaccga aaaaggtga agtgctgatt aaagtcaccc ataccggcgt ttgccatacc    3300
gacgcattta ccctctccgg ggatgacccg gaaggtgtat tcccggtggt tctcggtcac    3360
gaaggggccg cgcgttgtgg tgaagtcggt gaaggcgtaa ccagcgtcaa acctggcgac    3420
catgtgatcc cgctttacac cgcggagtgc ggcgagtgtg agttctgtcg ttctggcaaa    3480
```

```
actaacctct gtgttgcggt tcgcgaaacc cagggtaaag gcttgatgcc agacggcacc    3540
acccgttttt cttacaacgg gcagccgctt tatcactaca tgggatgctc aacattcagt    3600
gaatacaccg tggtcgcgga agtgtctctg gccaaaatta atccagaagc aaaccatgaa    3660
cacgtctgcc tgctgggctg tggcgtgacc accggtattg gcgcggtgca caacacagct    3720
aaagtccagc caggtgattc tgttgccgtg tttggtcttg gcgcgattgg tctggcagtg    3780
gttcagggcg cgcgtcaggc gaaagcggga cggattatcg ctatcgatac caacccgaag    3840
aaattcgatc tggctcgtcg cttcggtgct accgactgca ttaacccgaa tgactacgac    3900
aaaccgatta agatgtcct gctggatatc aacaaatggg gtatcgacca tacctttgaa    3960
tgcatcggta acgtcaacgt gatgcgtgcg gcgctggaaa gtgcgcaccg cggctggggt    4020
cagtcggtga tcatcggggt agcaggtgcc ggtcaggaaa tctccacccg accattccag    4080
ttggtcaccg gtcgcgtatg gaaaggttcc gcgtttggcg gcgtgaaagg tcgttcccag    4140
ttaccgggta tggttgaaga tgcgatgaaa ggtgatatcg atctggaacc gtttgtcacg    4200
cataccatga gccttgatga aattaatgac gccttcgacc tgatgcatga aggcaaatcc    4260
attcgaaccg taattcgtta ctgatttccc gcaggtatac cccgtccact tcagacgggg    4320
ttcttaatac tctccctggg cagccgtccg ggggattaac cgtgagataa tgactgatgg    4380
aactcattga aaacatgcc agctttggcg gctggcaaaa tgtgtatcgg cattattccc    4440
aatcactgaa atgtgaaatg aatgtcgcg tctatctccc accaaaagcc gcgaatgaaa    4500
aattgccggt gttgtactgg ctttcaggcc tgacttgcaa cgagcagaat tcattacta    4560 aatcggggat gcagcgttac gcggctgagc acaacattat tgttgttgcg ccggacacca    4620
gtccgcgagg cagtcatgtc gcagatgctg accgttacga tctcgggcaa ggtgccgggt    4680
tttacctgaa cgcgacgcaa gcgccgtgga atgaacatta caaatgtat gactatatcc    4740 gcaacgagct gccggattta gtgatgcatc attttccggc aacggccaaa aagtctatct    4800
ctggtcattc tatgggcggg ctgggcgcgc tggtgctggc gttacgtaac ccagatgaat    4860
atgtcagcgt ctcggcgttt tcgcccattg tctccccatc gcaagtgccg tggggacagc    4920
aagcctttgc tgcatatctt gctgaaaata aagatgcctg gttggattac gacccggtga    4980
gtcttatttc acaaggtcaa cgcgttgcgg aaatcatggt tgatcagggg ttgagtgatg    5040 attttttacgc agaacagctg cggactccaa atcttgaaaa gatctgccag gagatgaata    5100
tcaagacgtt aatccgttat cacgagggtt atgatcacag ctattatttt gtctccagtt    5160
ttattggcga gcatattgcc taccacgcca ataaactgaa tatgcgttga taatagtgca    5220
cgactgccgg atgcggcgtg aacgccttat ccggcctaca cttcgcccgt aaaccgtagg    5280
cctgataaga cgcgcaaagc gtcgcatcag gcatggcgca cgactgccgg atgcggcgtg    5340
aacgccttat ccggtctaca cttcgcccat aaaccgtagg cctgataaga cgcgcatagc    5400
gtcgcatcag gcatctgcgc acgacttatc tatgtttacc acatcaaatc atcaggcact    5460
ttgaagtcgg catacgggtc gtcttcatcc tgctcttcgg cgctgagcgc gctgtgcaac    5520
actatactgc tggcatcgcg ctgagcaatt ttatcggcaa cgctggcggg aataatggcg    5580
tattcacctt cgctattgtt atcgaccaac aagcgggcaa tcgccagacg accattaatc    5640
aactgcgcct gtgtgagctt atcgacaaaa atcttcttaa tcagattgcc gtcagtgaag    5700
ttaaaaccaa tatcgccatt ggcaatggtg attcggttca tttcaataag ctgcttcacc    5760
tgagctttat attcctttcgc caacgccgct tgttttgct gttcgctaag ctgttatca    5820 cgctcaagct gtgcctttt attttcttct accgccgccc gagcttcacg cgcctgaacg    5880
```

```
cgcgattttt tcgccgttct ctccaccttc gccgctttt tgctggtgac taatcctgct    5940
ttgagcaact gctcttgtaa ggtaagtttt gccatctttg tttccaaacc cgctgaataa    6000
tttttagcga gtatacctgt aaacgccgta ggtgtattgg ggtgaagtcc ctttcgcccc    6060
tgcctaataa ggcacgtcag gcatcggcgc acggctgtat tcgtgatctc cggctcatca    6120
aaataaacac cgccaaccca gcaacaagaa tacccggtgc agaagcggcc attacgccga    6180
ccgtgccagt gcctaatgcc agcatttttcc cggccagtaa cggaccgctc atagccccca    6240
gacgccctac cgccacggct gttcccacac ctgttgcgcg gatctgcgaa ctgtaaaaca    6300
acggtgccag ggcatacaaa cgctttgcc cacctgtcgc aaacaacccc gcgacaaatc    6360
ccgccagcaa cataccgtta aatgacgaca ccgttccaag cgccagcagc gaagctaaca    6420
tgccgctata aatcagtagc gacatggtta ctggacgcag cttatccatc aatgcgccca    6480
acattaacgt cccgcttgcc gccccatttt gcagggcaaa catcaccccct gccgcctgcg    6540 atggctggaa tccttgctcc accaaaagta gcggtagcca gttgatcaac atgtagacca    6600
ccagcagagt gaagaaataa cacaaccaca gcagcagcgt cgcggttgcc gtttctggcg    6660
caaataaggc acgcagtggt ggcgcagact gttttttcgcc agcgaaaacc gccgactccg    6720
gcagccagcg cattaatagc ggcaccagaa tcaacggcac cacaccacct acccaaaaca    6780
ccgtttgcca tgctaagttt gcccccgcga aacccagtgt cgccgccagc gccgcgccaa    6840
tgggaacacc gcaatacatc aggctcactg ccgtcccacg aaaacgtgga cccgcggctt    6900
cagacgtcag ggcgataaga ttcggcaacg ccgccccag cccgacaccg gtcatcagcc    6960
gcgcaaagac cagtgagggg aaatcccagg caatcgccgt tgccagtgag aacaaaccaa    7020
acagcgcaac tgagccaatc aaaatacgct tacgaccata acggtccgcc agcattccgc    7080
caaccaacgc gccgggtagc aaaccgagta ttccggcgct aaatatccag cccatttgca    7140
ttttatcgag tgcgaaagcc tgggcgatgc caccccgccgc aatgccagcc gcctgaagat    7200
ccagcccttc catcagagcg accaaaaaac aaagcccgat ggtcagcatc aggcgggatg    7260
aagatgatga aggggtacga gtcgacataa gatgcaactc attgcgagtg caggtgaatc    7320
gcgactgata cattgccagc cgcgtaatca gaactattga atgactgcct acgggcgaaa    7380
tgtaggccgg ataaggcgtt cacgccgcat ccggcagtcg tgtgcagatg cctgatgcga    7440
cgcttgcgcg tcttatcagg cctacaaatt cccgcgccat ccgtaggccg gataaggcgt    7500
ttacgccgca tccggcagtc gtgcgcagat gcctgatgcg acgctaacgc gtcttatcag    7560
gcctacaaat tctcgcgcca tccgtaggcc ggacaagacg ttcacgccgc atccggcagt    7620
cgtgctggga tgggcataca aaatgcacat tctcggcagt caatattatt tgttgttgcg    7680
cagatccagc gccacgtcga cgatcatatc ctcctggccg ccaaccatcc ggcgtttgcc    7740
cagctcaacg agaatatcca ccgcgcttaa gccataacgc gccgccgccg tttcacagtg    7800
acgcaggaag ctggagtaaa caccagcgta tcccagcgcc agcgtttcgc gatcgactcg    7860
taccggtcga tcctgcaacg gacgcaccag gtcgtcagcg gcatccatta acgcatagag    7920
atcggtccca tgctgccagc ccagtttatc cgcggcggca ataaatactt ccagcggcgc    7980
gttacctgcg cccgcgccca ttcccgcgag gctggcgtcg attcggtcgc agccctcttc    8040
caccgcctcg atagagttcg ccacgccaag actcaggtta tggtgagcgt gcatgccggt    8100 ttgcgttct ggtttcaaca ctgctttcag ggcgcgaaa cggtcacgga tatcgctcat    8160
gttcatcgca ccgccagaat ccaccacata aatacaggtc gcaccgtagc cttccatcag    8220
```

```
ctttgcctgc tttgcgagat tctctggcgt ggtcatatgg ctcatcatca gaaaaccaac      8280
ggtgtccatt ccgagctcgc gggcatactg aatatgctgg gcggaaacat cagcttcggt      8340
acagtgcgta gccacacgaa ccacccgcgc gccagcttgc caggcatttt tcagatcgtg      8400
aatagtgccg attcctggca gcaacaacgt cgcgattttg gcgtgcttca ccacatccgc      8460
cgctgcttca atccattcaa ggtcgctatg tgcgccgaaa ccatagttaa agctggaacc      8520
ctgcaaaccg tcgccgtggg ccacttcaat cgaatccacg tgggcatcgt ccagtgcttt      8580
ggcaatctgg cgaacgtttt ccagcgaata ctgatgacga atggcgtgca taccgtcacg      8640
caacgtgacg tccagagatat aaagtttttt accgttcatg ccgcttctcc tgccttgcgc      8700
gccagtgact gggccatttt ttccgctgtc gccagcgcac tggaagtcat aatgtcgagg      8760
ttgcccgcat aggcaggcag ataatgcgct gcgccttcga cttccagcca gaccgctgtt      8820
ttcagtccgg agaattgccc cacgcccggt aaattgaccg gtttatcctg cgggataact      8880
tcaaactgca cgcgctgttt caggcgataa cccggtacgt aagcctgcac cgcctcagcc      8940
atttcattga ttgaggcttc gatatcatct tgtgaagctt cgtcgctcaa tacatacacc      9000
gtgtcacgca tcatcaacgg tggctctgct gggttaagca caataatcgc cttccctttt      9060
gccgcgccgc ccaccacttc aatggctcgg gaagtggttt ccgtaaattc atcgatattg      9120
gcacgcgtgc caggtccggc agatttactg gcgatagaag cgataatttc ggcgtaatga      9180
acacgcgcca cgcgtgaaac tgccgccacc attggaatgg tggcctggcc gccgcaggtg      9240
accatgttga cgttcagttg atcgacgttc gcctcgaggt taaccaccgg cacgcagtaa      9300
gggccgatgg cagcaggcgt caggtcaatt aagcgaatat ccggtttcgc ttcgcgtaaa      9360
gcggcatcgt ttttcacatg agcaccggcg ctggtcgcat caaatacaat gtcgatatca      9420
gcaaattcag gcatgttcat cagtccgatc accccttcat gggtggtggc gacgcccata      9480
cgtctggcgc gcgccagacc gtcggactga ggatcaatgc caaccatcac cgccatctcc      9540
agatgctgac cgtgacgcaa aattttaatc atcagatcgg tgccaatgtt gccagaaccg      9600
ataatggcga cttacgcgtt actcatgaca gacttccttt tggggctgcg cttgaaaatg      9660
tcgcagcaac tgaacctatg ccttcaatat gggcttcaaa acgatcgccc gcattcaccg      9720
ccaccatcgg acctaatgcc ccggtaagaa tgatatctcc ggtgcgcagc ggttcaccca      9780
gactggccat tttgcgtgcc agccagacgg ccgcattaag cggatgtccc aggcattcgc      9840
tgccgcgccc gctagaaacc tcttcgttat tacgcgtcat cttcatggcg cagttttca      9900
ggtctaaccc cgccggacgt tgcgccggac cgccgatgac atacacccca caggaggcgt      9960
tatctgccac ggtatcgaca aactgaatcg accagtcgcg aatgcggctc cccaccactt     10020
ccagcgccgg aagtacccat tcaatggcgt tatacaattc gtcgaaggtg atatcggttg     10080
cgggcaaatc gcggttcaac accagtgcga tctccgcttc aatgcggggt tgcagaacac     10140
gggaaaaagg aatgatttcg ttatcgccat aacacatgtc ggcaaataat gtcccgaaat     10200
ccggttgatc aacgcccagt tgttgctgca ctttcggatg cgtcaggccc actttacgcc     10260
ctaccacgcg acgcccctgc gcaacgtcat attgcacatt tatgtgctga atggcgtagg     10320
ccgcttcagc gttatcgata ccaatcagat cgcgcagcgg cgcaatcgct tcgccctgct     10380
ctgcggcgcg gcgtaaatcc gccgccagtt gctcaagagt atgcttcgtc atgaccattc     10440
cttaagggcg tgcgaggaaa ttcagcacca attgattgaa agcgtcggca tgttcccact     10500
gcgcccagtg accacagtcg cggaagatat gcagttcaga accggcaatg ccggacagca     10560
gacgcagacc cgcatccatc ggcacaaagc ggtcgttgcg cccccagaca atcagggttt     10620
```

```
gcgctttgat tccgccaga cgtgggccaa aatccgggaa ctgtttcgga ttagcttcca    10680
ggctcttaac gaagttttcc aggtgatcgc ggcgcgacag catattattc aggcgcgctt    10740
caaacagggc gtcggtcaaa tcgctggtat cgaaaacgaa gatatccatc atcagcttca    10800
ggttttcgat agtcggctga cgataaagct gattcagtcg cttaatacct tcggttggca    10860
tcggcgtaaa caaactcatg ccgcccgtac cgccgcccat cagcaccagt ttgccgacgc    10920
gctccggcca gttaagggtg aacgccacag aactatggcc gcccatcgag ttgcccagca    10980
ggtggatttt ggcgatatcc agttgatcca ccacgctttt caggattcgt gcattaagat    11040
ccgatcgtga accactatta acgatcgaat cgcttttgcc ccaacccgga caatccagca    11100
ggatcacccg atagcccgcc tctaccagcg gatcgatatt gcggctgaag ttcgcccagc    11160
cagtagcacc cggccggaa ccatgcagca ggacaacggt ttcgtcgcct tgtccgcagt    11220
cattaaaatg gatgcgcagc gttttacccg cttcttctac attcagaaaa cggctggtgg    11280
cggcttcggt ttgtggctga taactcatca tcttctcctg catattcagt tctctgttct    11340
ggcgcttaac gagccaaatc cggcaatcca ctccgggatt gggcggtaat aacgcccttc    11400
gctacgccag ttgccaaatg cagaaatagc ggcaaaagcg gcgacccagg ttttgatttc    11460
atgtgtcgac tttccggcaa tggcggaaag ctcttcgtta ctgacggcat ccagttcctg    11520
tatgcgtccc tgctccagca aagtcatgaa ctggttatcc caaatcgggt tgagcggatg    11580
cagagttctc tgatcctcaa caaacttctc agcggcgcta atcacccgtt gctgacgcaa    11640
ttcgcgctca ctggcgggta aatctttccc gctccccaac agacggtcgc gcatatgggc    11700
atcggctttc gccagttcgg gcaccggcgg ctgatgggaa agcccaccgg aacccaggaa    11760
cagcacgcgt ttattgagag tgctggtgaa acgtccaatg gcttcaccca acatgcgggt    11820
acgctggaaa ccgggcagcg gcgtggcgac accgttgatg aacacaggca gaactggcac    11880
cttatccagc ccgccgagca ggaactccag tggctgggcg aacccgtggt ccacctgcat    11940
acagtaagaa acggcaagat cgatcccgct cttcatgacg gcatgcgcac aggcctccgc    12000
cagctccaca ggcacgggca gctctcctgc cgcactgccg aaatcaccaa ttgccgtcgc    12060
cccaacgcct aaacagaacg gtggcatcac gtcatagaaa aagccgttgt agtgatctgg    12120
cgcaaacagc accaccagtt caggggagaa agccgcaata cgctcgcggg cgctggcaat    12180
cacgccattg acctcatcga gtacctcttg cgccgggtcg acatatccca ccagcggcga    12240
gtgggaaaga cagtgaagat aagcgtgcat atcaggctac cttttcgaca gaaacgtcgg    12300
catcagggcg ggtcagcgtc atcaccgacg ccagtttatt cagcgtatta cccagggttt    12360
gcggaatggc ggtggcggca acaaagcgat ccgggcgcat caccaccagc gaagcattat    12420
gttgtgcgaa ccagctacgc aggcgacctt gcgtatcccc cacgcgtagt acgccgtcgt    12480
ggttatcctg tgcggtatga atttgcactt ccggcaccac ctgaatgaag cgggtgccca    12540
acgcgcgcca ctgctggatt tgctcgtcgc tcatccccca cagtggattg catcccagc    12600 caattaccgc gaagttcgcg ccgatcgcgt tatcgagcag cgtcacgtcg ccgttttcca    12660
gcgtgacttt cggctgaata acatcttgc cgaccggaga gtgcttcgct tcgccctctc    12720
gcaccagcgc accgccgtaa tattgcggca tcggcttgaa gcgcatttcg aggaagtagc    12780
gttttactgg cggcagataa ttcaacagcc aggaaacgcc gtcacgtaac gtaccctgcc    12840
agcgtttcgg cggagccagc acgttgcccg ccgtcacgga caggtcaatc atcgctttgg    12900
cgtgatcgcg tcgttcttgt tgataggtat cgagcagcgc atcacgggct ttcccctgga    12960
```

```
taaccaacgc cagtttccag gcgaggttaa aggcgtcgcg cataccgctg ttatagccct    13020 gccoctgcca taccggcatg atgtgcgcgg catcgcccgc cagcagtacg cgatcaatac    13080
ggaaacgttg cgccagtcgc gcgttgtggg tgtagacacg ctggcgaatc aattcaacat    13140
tgtccggatt aggcagcact ttgcttaaca gcttgcgcat attttgcggc tcacgcagct    13200
gttcttcggt ttctcctggc atcaccataa attcaaagcg acgtaccgca tgaggtagcg    13260
cggcagaaac atacgggcgc accggatcgc aacacaaata gatatgcggc gtacttaacg    13320
gatcgttggc gatatctacc acaatccact gatttggcgc agttttacct tcaaacggca    13380
cattcagggt gcgacggaca aaacttgccc caccatcaca ggccaccagc cactgggctt    13440
tgactatttc ccgctgccct tctgccgttt tcaggtgcaa ggtcacttcg tcatcttgct    13500
gactgaaggc ctccagctcg cgggaaaaca agcagcgcac attcggaaaa cgcgacaccc    13560
cttccagcat caccgcatcg acctgcggct gaataaaggc gttacggcgc ggccagccaa    13620
attcatcggt cattggctga atatcagcaa aacagcggcc tttcggggtg agaaaacgca    13680
tcgcgtgcca cggcgtagtg tgcggcagaa catcatcgac caggccgacc gactgcatgg    13740
tgcgcagcgc ctcgtcatca ataccaatcg cacgcgggta gtcgatcaac ttatcgagtt    13800
tctccaccac cagcacgtca atgcccatct ggccgagata gttcgccatc atcagcccaa    13860
ccgggccggc accagcgatc gccacctgaa cgctatggtt aacagcaggc tggatgtcag    13920
ggtgttgtat tgccatttca gtacctcacg actcggacaa aatgtcgttg cgcgcacagt    13980
acagcgcaac ttattttgtt aaaaacatgt aaatgatttt ttattgtgcg ctcagtatag    14040
gaagggtgtt ttcggctaca atcaaaacat gcccgaatgt gcaccaggtg caccacgttg    14100
ttttaactat agaaatgtca attaatatgc agaacaatga gcagacggaa tacaaaaccg    14160
tgcgcggctt aacccgcggt ctaatgttat taaatatgtt aaataaactt gatggcggtg    14220
ccagcgtcgg gctgctggcg gaactcagcg gcctgcatcg caccactgtg cggcgactgc    14280
tggagacgct gcaggaagag ggatatgtcc gccgtagccc ctccgatgat agttttcgac    14340
tgaccatcaa agtgcggcaa ttaagcgaag gatttcgtga cgaacagtgg atttctgcac    14400
tggcggcccc actgctgggc gatctgttgc gcgaagtggt atggccgaca gatgtgtcca    14460
cgctggatgt tgatgcaatg gtggtacgcg aaaccactca ccgtttcagc cgcttatcct    14520
ttcaccgggc aatggtcggg cgacgtttgc cgcttctgaa aaccgcctcg ggcctgacct    14580
ggctggcctt ttgcccggaa caagaccgca aggaattaat cgaaatgtta gcctcccgcc    14640
ccggtgatga ctatcaactg gcacgggaac cgttaaagct ggaagccatt ctggcgcgcg    14700
cgcgcaaaga gggttacgga cagaactacc gcggctggga tcaggaggag aagatcgcct    14760
ctatcgccgt accgctgcgc agtgaacaac gggtgattgg ctgtctgaat ctggtgtata    14820
tggcgagcgc aatgaccatt gaacaggcag cggaaaagca tcttccggcg ctacaacggg    14880
tagcaaaaca gatcgaagaa ggggttgaat cgcaggctat tctggtggcc ggaaggcgaa    14940
gcggcatgca tttacgttga caccatcgaa tggcgcaaaa cctttcgcgg tatggcatga    15000
tagcgcccgg aagagagtca attcaggtgtg gtgaatgtga accagtaac gttatacgat    15060 gtcgcagagt atgccggtgt ctcttatcag accgtttccc gcgtggtgaa ccaggccagc    15120
cacgtttctg cgaaaacgcg ggaaaaagtg gaagcggcga tggcggagct gaattacatt    15180
cccaaccgcg tggcacaaca actggcgggc aaacagtcgt tgctgattgg cgttgccacc    15240
tccagtctgg ccctgcacgc gccgtcgcaa attgtcgcgg cgattaaatc tcgcgccgat    15300
caactgggtg ccagcgtggt ggtgtcgatg gtagaacgaa gcggcgtcga agcctgtaaa    15360
```

```
gcggcggtgc acaatcttct cgcgcaacgc gtcagtgggc tgatcattaa ctatccgctg    15420
gatgaccagg atgccattgc tgtggaagct gcctgcacta atgttccggc gttatttctt    15480
gatgtctctg accagacacc catcaacagt attattttct cccatgaaga cggtacgcga    15540
ctgggcgtgg agcatctggt cgcattgggt caccagcaaa tcgcgctgtt agcgggccca    15600
ttaagttctg tctcggcgcg tctgcgtctg gctggctggc ataaatatct cactcgcaat    15660
caaattcagc cgatagcgga acgggaaggc gactggagtg ccatgtccgg ttttcaacaa    15720
accatgcaaa tgctgaatga gggcatcgtt cccactgcga tgctggttgc caacgatcag    15780
atggcgctgg gcgcaatgcg cgccattacc gagtccgggc tgcgcgttgg tgcggatatc    15840
tcggtagtgg atacgacga taccgaagac agctcatgtt atatcccgcc gttaaccacc    15900
atcaaacagg attttcgcct gctggggcaa accagcgtgg accgcttgct gcaactctct    15960
cagggccagg cggtgaaggg caatcagctg ttgcccgtct cactggtgaa agaaaaaacc    16020
accctggcgc ccaatacgca aaccgcctct ccccgcgcgt tggccgattc attaatgcag    16080
ctggcacgac aggtttcccg actggaaagc gggcagtgag cgcaacgcaa ttaatgtaac    16140
taggcacccc aggcttttaca ctttatgctt ccggctggta taatgtgtgg acctgtagaa    16200
ataattttgt ttaactttaa taaggagata taccatggga ggcagtactg ttgcaccaac    16260
tacaccgttg gcaaccggcg gtgcgctccg caaagtgcga caagccgtct ttcccatcta    16320
cggaaaccaa gaagtcacca aatttctgct catcggatcc attaaattct ttataatctt    16380
ggcactcacg ctcacgcgtg ataccaagga cacgttgatt gtcacgcaat gtggtgccga    16440
agcgattgcc tttctcaaaa tatacggggt gctacccgca gcgaccgcat ttatcgcgct    16500
ctattccaaa atgtccaacg ccatgggcaa aaaaatgcta ttttattcca cttgcattcc    16560
tttctttacc tttttcgggc tgtttgatgt tttcatttac ccgaacgcgg agcgactgca    16620
ccctagtttg gaagccgtgc aggcaattct cccgggcggt gccgcatctg gcggcatggc    16680
ggttctggcc aagattgcga cacactggac atcggcctta ttttacgtca tggcggaaat    16740
atattcttcc gtatcggtgg ggctattgtt ttggcagttt gcgaacgacg tcgtcaacgt    16800
ggatcaggcc aagcgctttt atccattatt tgctcaaatg agtggcctcg ctccagtttt    16860
agcgggccag tatgtggtac ggtttgccag caaagcggtc aactttgagg catccatgca    16920
tcgactcacg gcgccgtaa catttgctgg tattatgatt tgcatctttt accaactcag    16980
ttcgtcatat gtggagcgaa cggaatcagc aaagccagcg gcagataacg agcagtctat    17040
caaaccgaaa aagaagaaac ccaaaatgtc catggttgaa tcggggaaat ttctcgcgtc    17100
aagtcagtac ctgcgtctaa ttgccatgct ggtgctggga tacggcctca gtattaactt    17160
taccgaaatc atgtggaaaa gcttggtgaa gaaacaatat ccagaccgcc tagattatca    17220
acgatttatg ggtaacttct cgtcagcggt tggtttgagc acatgcattg ttatttttctt    17280 cggtgtgcac gtgatccgtt tgttggggtg gaaagtcgga gcgttggcta cacctgggat    17340
catggccatt ctagcgttac ccttttttgc ttgcatttg ttgggtttgg atagtccagc    17400
acgattggag atcgccgtaa tctttggaac aattcagagt ttgctgagca aaacctccaa    17460
gtatgccctt ttcgacccta ccacacaaat ggcttatatt cctctggacg acgaatcaaa    17520
ggtcaaagga aaagcggcaa ttgatgtttt gggatcgcgg attggcaaga gtggaggctc    17580
actgatccag cagggcttgg tctttgtttt tggaaatatc attaatgccg cacctgtagt    17640
aggggttgtc tactacagtg tccttgttgc gtggatgagc gcagctggcc gactaagtgg    17700
```

```
gctttttcaa gcacaaacag aaatggataa ggccgacaaa atggaggcaa agaccaacaa    17760
agaaaagtag ttaacctagg ctgctgccac cgctgagcaa taagactcct gttgatagat    17820
ccagtaatga cctcagaact ccatctggat ttgttcagaa cgctcggttg ccgccgggcg    17880 tttttttattg gtgagaat                                                 17898
```

<210> SEQ ID NO 6
<211> LENGTH: 125
<212> TYPE: DNA
<213> ORGANISM: Escherichia coli

<400> SEQUENCE: 6

```
aggagtaaaa atgattccgg ggatccgtcg acctgcagtt cgaagttcct attctctaga     60
aagtatagga acttcgaagc agctccagcc tacagaaact aacgaagatt tttaatcgtc    120
ttgtt                                                                125
```

<210> SEQ ID NO 7
<211> LENGTH: 1082
<212> TYPE: DNA
<213> ORGANISM: Escherichia coli

<400> SEQUENCE: 7

```
aggagtaaaa atggctatcg acgaaaacaa acagaaagcg ttggcggcag cactgggcca     60
gattgagaaa caatttggta aaggctccat catgcgcctg ggtgaagacc gttccatgga    120
tgtggaaacc atctctaccg gttcgctttc actggatatc gcgcttgggg caggtggtct    180
gccgatgggc cgtatcgtcg aaatctacgg accggaatct tccggtaaaa ccacgctgac    240
gctgcaggtg atcgccgcag cgcagcgtga aggtaaaacc tgtgcgttta tcgatgctga    300
acacgcgctg gacccaatct acgcacgtaa actgggcgtc gatatcgata acctgctgtg    360
ctcccagccg acaccggcg agcaggcact ggaaatctgt gacgccctgg cgcgttctgg    420
cgcagtagac gttatcgtcg ttgactccgt ggcggcactg acgccgaaag cggaaatcga    480
aggcgaaatc ggcgactctc acatgggcct tgcggcacgt atgatgagcc aggcgatgcg    540
taagctggcg ggtaacctga agcagtccaa cacgctgctg atcttcatca accagatccg    600
tatgaaaatt ggtgtgatgt tcggtaaccc ggaaaccact accggtggta acgcgctgaa    660
attctacgcc tctgttcgtc tcgacatccg tcgtatcggc gcggtgaaag agggcgaaaa    720
cgtggtgggt agcgaaaccc gcgtgaaagt ggtgaagaac aaaatcgctg cgccgtttaa    780
acaggctgaa ttccagatcc tctacggcga aggtatcaac ttctacgcg aactggttga    840 cctgggcgta aaagagaagc tgatcgagaa agcaggcgcg tggtacagct acaaaggtga    900
gaagatcggt cagggtaaag cgaatgcgac tgcctggctg aaagataacc cggaaaccgc    960
gaaagagatc gagaagaaag tacgtgagtt gctgctgagc aacccgaact caacgccgga   1020
tttctctgta gatgatagcg aaggcgtagc agaaactaac gaagattttt aatcgtcttg   1080
tt                                                                   1082
```

<210> SEQ ID NO 8
<211> LENGTH: 783
<212> TYPE: PRT
<213> ORGANISM: Escherichia coli

<400> SEQUENCE: 8

```
Met Ala Gln Ala Gly Phe Ile Leu Thr Arg His Trp Arg Asp Thr Pro
1               5                   10                  15
```

```
Gln Gly Thr Glu Val Ser Phe Trp Leu Ala Thr Asp Asn Gly Pro Leu
                20                  25                  30

Gln Val Thr Leu Ala Pro Gln Glu Ser Val Ala Phe Ile Pro Ala Asp
            35                  40                  45

Gln Val Pro Arg Ala Gln His Ile Leu Gln Gly Glu Gln Gly Val Arg
        50                  55                  60

Leu Thr Pro Leu Ala Leu Lys Asp Phe His Arg Gln Pro Val Tyr Gly
65                  70                  75                  80

Leu Tyr Cys Arg Ala His Arg Gln Leu Met Asn Tyr Glu Lys Arg Leu
                85                  90                  95

Arg Glu Gly Gly Val Thr Val Tyr Glu Ala Asp Val Arg Pro Pro Glu
            100                 105                 110

Arg Tyr Leu Met Glu Arg Phe Ile Thr Ser Pro Val Trp Val Glu Gly
        115                 120                 125

Asp Met His Asn Gly Ala Ile Val Asn Ala Arg Leu Lys Pro His Pro
    130                 135                 140

Asp Tyr Arg Pro Pro Leu Lys Trp Val Ser Ile Asp Ile Glu Thr Thr
145                 150                 155                 160

Arg His Gly Glu Leu Tyr Cys Ile Gly Leu Glu Gly Cys Gly Gln Arg
                165                 170                 175

Ile Val Tyr Met Leu Gly Pro Glu Asn Gly Asp Ala Ser Ala Leu Asp
            180                 185                 190

Phe Glu Leu Glu Tyr Val Ala Ser Arg Pro Gln Leu Leu Glu Lys Leu
        195                 200                 205

Asn Ala Trp Phe Ala Asn Tyr Asp Pro Asp Val Ile Ile Gly Trp Asn
    210                 215                 220

Val Val Gln Phe Asp Leu Arg Met Leu Gln Lys His Ala Glu Arg Tyr
225                 230                 235                 240

Arg Ile Pro Leu Arg Leu Gly Arg Asp Asn Ser Glu Leu Glu Trp Arg
                245                 250                 255

Glu His Gly Phe Lys Asn Gly Val Phe Phe Ala Gln Ala Lys Gly Arg
            260                 265                 270

Leu Ile Ile Asp Gly Ile Glu Ala Leu Lys Ser Ala Phe Trp Asn Phe
        275                 280                 285

Ser Ser Phe Ser Leu Glu Thr Val Ala Gln Glu Leu Leu Gly Glu Gly
    290                 295                 300

Lys Ser Ile Asp Asn Pro Trp Asp Arg Met Asp Glu Ile Asp Arg Arg
305                 310                 315                 320

Phe Ala Glu Asp Lys Pro Ala Leu Ala Thr Tyr Asn Leu Lys Asp Cys
                325                 330                 335

Glu Leu Val Thr Gln Ile Phe His Lys Thr Glu Ile Met Pro Phe Leu
            340                 345                 350

Leu Glu Arg Ala Thr Val Asn Gly Leu Pro Val Asp Arg His Gly Gly
        355                 360                 365

Ser Val Ala Ala Phe Gly His Leu Tyr Phe Pro Arg Met His Arg Ala
    370                 375                 380

Gly Tyr Val Ala Pro Asn Leu Gly Glu Val Pro Pro His Ala Ser Pro
385                 390                 395                 400

Gly Gly Tyr Val Met Asp Ser Arg Pro Gly Leu Tyr Asp Ser Val Leu
                405                 410                 415

Val Leu Asp Tyr Lys Ser Leu Tyr Pro Ser Ile Ile Arg Thr Phe Leu
            420                 425                 430
```

```
Ile Asp Pro Val Gly Leu Val Glu Gly Met Ala Gln Pro Asp Pro Glu
        435                 440                 445

His Ser Thr Glu Gly Phe Leu Asp Ala Trp Phe Ser Arg Glu Lys His
        450                 455                 460

Cys Leu Pro Glu Ile Val Thr Asn Ile Trp His Gly Arg Asp Glu Ala
465                 470                 475                 480

Lys Arg Gln Gly Asn Lys Pro Leu Ser Gln Ala Leu Lys Ile Met
                485                 490                 495

Asn Ala Phe Tyr Gly Val Leu Gly Thr Thr Ala Cys Arg Phe Phe Asp
                500                 505                 510

Pro Arg Leu Ala Ser Ser Ile Thr Met Arg Gly His Gln Ile Met Arg
        515                 520                 525

Gln Thr Lys Ala Leu Ile Glu Ala Gln Gly Tyr Asp Val Ile Tyr Gly
        530                 535                 540

Asp Thr Asp Ser Thr Phe Val Trp Leu Lys Gly Ala His Ser Glu Glu
545                 550                 555                 560

Glu Ala Ala Lys Ile Gly Arg Ala Leu Val Gln His Val Asn Ala Trp
                565                 570                 575

Trp Ala Glu Thr Leu Gln Lys Gln Arg Leu Thr Ser Ala Leu Glu Leu
        580                 585                 590

Glu Tyr Glu Thr His Phe Cys Arg Phe Leu Met Pro Thr Ile Arg Gly
        595                 600                 605

Ala Asp Thr Gly Ser Lys Lys Arg Tyr Ala Gly Leu Ile Gln Glu Gly
        610                 615                 620

Asp Lys Gln Arg Met Val Phe Lys Gly Leu Glu Thr Val Arg Thr Asp
625                 630                 635                 640

Trp Thr Pro Leu Ala Gln Gln Phe Gln Gln Glu Leu Tyr Leu Arg Ile
                645                 650                 655

Phe Arg Asn Glu Pro Tyr Gln Glu Tyr Val Arg Glu Thr Ile Asp Lys
                660                 665                 670

Leu Met Ala Gly Glu Leu Asp Ala Arg Leu Val Tyr Arg Lys Arg Leu
        675                 680                 685

Arg Arg Pro Leu Ser Glu Tyr Gln Arg Asn Val Pro Pro His Val Arg
        690                 695                 700

Ala Ala Arg Leu Ala Asp Glu Glu Asn Gln Lys Arg Gly Arg Pro Leu
705                 710                 715                 720

Gln Tyr Gln Asn Arg Gly Thr Ile Lys Tyr Val Trp Thr Thr Asn Gly
                725                 730                 735

Pro Glu Pro Leu Asp Tyr Gln Arg Ser Pro Leu Asp Tyr Glu His Tyr
                740                 745                 750

Leu Thr Arg Gln Leu Gln Pro Val Ala Glu Gly Ile Leu Pro Phe Ile
        755                 760                 765

Glu Asp Asn Phe Ala Thr Leu Met Thr Gly Gln Leu Gly Leu Phe
        770                 775                 780

<210> SEQ ID NO 9
<211> LENGTH: 320
<212> TYPE: PRT
<213> ORGANISM: Escherichia coli

<400> SEQUENCE: 9

Met Ala Ile Ser Ser Arg Asn Thr Leu Leu Ala Ala Leu Ala Phe Ile
1               5                   10                  15
```

```
Ala Phe Gln Ala Gln Ala Val Asn Val Thr Val Ala Tyr Gln Thr Ser
                20                  25                  30

Ala Glu Pro Ala Lys Val Ala Gln Ala Asp Asn Thr Phe Ala Lys Glu
            35                  40                  45

Ser Gly Ala Thr Val Asp Trp Arg Lys Phe Asp Ser Gly Ala Ser Ile
        50                  55                  60

Val Arg Ala Leu Ala Ser Gly Asp Val Gln Ile Gly Asn Leu Gly Ser
65                  70                  75                  80

Ser Pro Leu Ala Val Ala Ala Ser Gln Gln Val Pro Ile Glu Val Phe
                85                  90                  95

Leu Leu Ala Ser Lys Leu Gly Asn Ser Glu Ala Leu Val Val Lys Lys
            100                 105                 110

Thr Ile Ser Lys Pro Glu Asp Leu Ile Gly Lys Arg Ile Ala Val Pro
        115                 120                 125

Phe Ile Ser Thr Thr His Tyr Ser Leu Leu Ala Ala Leu Lys His Trp
130                 135                 140

Gly Ile Lys Pro Gly Gln Val Glu Ile Val Asn Leu Gln Pro Pro Ala
145                 150                 155                 160

Ile Ile Ala Ala Trp Gln Arg Gly Asp Ile Asp Gly Ala Tyr Val Trp
                165                 170                 175

Ala Pro Ala Val Asn Ala Leu Glu Lys Asp Gly Lys Val Leu Thr Asp
            180                 185                 190

Ser Glu Gln Val Gly Gln Trp Gly Ala Pro Thr Leu Asp Val Trp Val
        195                 200                 205

Val Arg Lys Asp Phe Ala Glu Lys His Pro Glu Val Val Lys Ala Phe
210                 215                 220

Ala Lys Ser Ala Ile Asp Ala Gln Gln Pro Tyr Ile Ala Asn Pro Asp
225                 230                 235                 240

Ala Trp Leu Lys Gln Pro Glu Asn Ile Ser Lys Leu Ala Arg Leu Ser
                245                 250                 255

Gly Val Pro Glu Gly Asp Val Pro Gly Leu Val Lys Gly Asn Thr Tyr
            260                 265                 270

Leu Thr Pro Gln Gln Gln Thr Ala Glu Leu Thr Gly Pro Val Asn Lys
        275                 280                 285

Ala Ile Ile Asp Thr Ala Gln Phe Leu Lys Glu Gln Gly Lys Val Pro
290                 295                 300

Ala Val Ala Asn Asp Tyr Ser Gln Tyr Val Thr Ser Arg Phe Val Gln
305                 310                 315                 320

<210> SEQ ID NO 10
<211> LENGTH: 91
<212> TYPE: PRT
<213> ORGANISM: Escherichia coli

<400> SEQUENCE: 10

Met Ala Ser Val Ser Ile Ser Cys Pro Ser Cys Ser Ala Thr Asp Gly
1               5                   10                  15

Val Val Arg Asn Gly Lys Ser Thr Ala Gly His Gln Arg Tyr Leu Cys
            20                  25                  30

Ser His Cys Arg Lys Thr Trp Gln Leu Gln Phe Thr Tyr Thr Ala Ser
        35                  40                  45

Gln Pro Gly Thr His Gln Lys Ile Ile Asp Met Ala Met Asn Gly Val
    50                  55                  60
```

Gly Cys Arg Ala Thr Ala Arg Ile Met Gly Val Gly Leu Asn Thr Ile
65                  70                  75                  80

Leu Arg His Leu Lys Asn Ser Gly Arg Ser Arg
                85                  90

<210> SEQ ID NO 11
<211> LENGTH: 167
<212> TYPE: PRT
<213> ORGANISM: Escherichia coli

<400> SEQUENCE: 11

Met Pro Gly Asn Cys Pro His Tyr Gly Arg Trp Pro Gln His Asp Phe
1               5                   10                  15

Thr Ser Leu Lys Lys Leu Arg Pro Gln Ser Val Thr Ser Arg Ile Gln
                20                  25                  30

Pro Gly Ser Asp Val Ile Val Cys Ala Glu Met Asp Glu Gln Trp Gly
            35                  40                  45

Tyr Val Gly Ala Lys Ser Arg Gln Arg Trp Leu Phe Tyr Ala Tyr Asp
    50                  55                  60

Arg Leu Arg Lys Thr Val Val Ala His Val Phe Gly Glu Arg Thr Met
65                  70                  75                  80

Ala Thr Leu Gly Arg Leu Met Ser Leu Met Ser Pro Phe Asp Val Val
                85                  90                  95

Ile Trp Met Thr Asp Gly Trp Pro Leu Tyr Glu Ser Arg Leu Lys Gly
            100                 105                 110

Lys Leu His Val Ile Ser Lys Arg Tyr Thr Gln Arg Ile Glu Arg His
        115                 120                 125

Asn Leu Asn Leu Arg Gln His Leu Ala Arg Leu Gly Arg Lys Ser Leu
130                 135                 140

Ser Phe Ser Lys Ser Val Glu Leu His Asp Lys Val Ile Gly His Tyr
145                 150                 155                 160

Leu Asn Ile Lys His Tyr Gln
                165

<210> SEQ ID NO 12
<211> LENGTH: 511
<212> TYPE: PRT
<213> ORGANISM: Escherichia coli

<400> SEQUENCE: 12

Met Gly Gly Ser Thr Val Ala Pro Thr Thr Pro Leu Ala Thr Gly Gly
1               5                   10                  15

Ala Leu Arg Lys Val Arg Gln Ala Val Phe Pro Ile Tyr Gly Asn Gln
                20                  25                  30

Glu Val Thr Lys Phe Leu Leu Ile Gly Ser Ile Lys Phe Phe Ile Ile
            35                  40                  45

Leu Ala Leu Thr Leu Thr Arg Asp Thr Lys Asp Thr Leu Ile Val Thr
    50                  55                  60

Gln Cys Gly Ala Glu Ala Ile Ala Phe Leu Lys Ile Tyr Gly Val Leu
65                  70                  75                  80

Pro Ala Ala Thr Ala Phe Ile Ala Leu Tyr Ser Lys Met Ser Asn Ala
                85                  90                  95

Met Gly Lys Lys Met Leu Phe Tyr Ser Thr Cys Ile Pro Phe Phe Thr
            100                 105                 110

Phe Phe Gly Leu Phe Asp Val Phe Ile Tyr Pro Asn Ala Glu Arg Leu
        115                 120                 125

His Pro Ser Leu Glu Ala Val Gln Ala Ile Leu Pro Gly Gly Ala Ala
    130                 135                 140

Ser Gly Gly Met Ala Val Leu Ala Lys Ile Ala Thr His Trp Thr Ser
145                 150                 155                 160

Ala Leu Phe Tyr Val Met Ala Glu Ile Tyr Ser Ser Val Ser Val Gly
                165                 170                 175

Leu Leu Phe Trp Gln Phe Ala Asn Asp Val Val Asn Val Asp Gln Ala
            180                 185                 190

Lys Arg Phe Tyr Pro Leu Phe Ala Gln Met Ser Gly Leu Ala Pro Val
        195                 200                 205

Leu Ala Gly Gln Tyr Val Val Arg Phe Ala Ser Lys Ala Val Asn Phe
210                 215                 220

Glu Ala Ser Met His Arg Leu Thr Ala Ala Val Thr Phe Ala Gly Ile
225                 230                 235                 240

Met Ile Cys Ile Phe Tyr Gln Leu Ser Ser Ser Tyr Val Glu Arg Thr
                245                 250                 255

Glu Ser Ala Lys Pro Ala Ala Asp Asn Glu Gln Ser Ile Lys Pro Lys
            260                 265                 270

Lys Lys Lys Pro Lys Met Ser Met Val Glu Ser Gly Lys Phe Leu Ala
        275                 280                 285

Ser Ser Gln Tyr Leu Arg Leu Ile Ala Met Leu Val Leu Gly Tyr Gly
290                 295                 300

Leu Ser Ile Asn Phe Thr Glu Ile Met Trp Lys Ser Leu Val Lys Lys
305                 310                 315                 320

Gln Tyr Pro Asp Pro Leu Asp Tyr Gln Arg Phe Met Gly Asn Phe Ser
                325                 330                 335

Ser Ala Val Gly Leu Ser Thr Cys Ile Val Ile Phe Phe Gly Val His
            340                 345                 350

Val Ile Arg Leu Leu Gly Trp Lys Val Gly Ala Leu Ala Thr Pro Gly
        355                 360                 365

Ile Met Ala Ile Leu Ala Leu Pro Phe Phe Ala Cys Ile Leu Leu Gly
370                 375                 380

Leu Asp Ser Pro Ala Arg Leu Glu Ile Ala Val Ile Phe Gly Thr Ile
385                 390                 395                 400

Gln Ser Leu Leu Ser Lys Thr Ser Lys Tyr Ala Leu Phe Asp Pro Thr
                405                 410                 415

Thr Gln Met Ala Tyr Ile Pro Leu Asp Asp Glu Ser Lys Val Lys Gly
            420                 425                 430

Lys Ala Ala Ile Asp Val Leu Gly Ser Arg Ile Gly Lys Ser Gly Gly
        435                 440                 445

Ser Leu Ile Gln Gln Gly Leu Val Phe Val Phe Gly Asn Ile Ile Asn
450                 455                 460

Ala Ala Pro Val Val Gly Val Val Tyr Tyr Ser Val Leu Val Ala Trp
465                 470                 475                 480

Met Ser Ala Ala Gly Arg Leu Ser Gly Leu Phe Gln Ala Gln Thr Glu
                485                 490                 495

Met Asp Lys Ala Asp Lys Met Glu Ala Lys Thr Asn Lys Glu Lys
            500                 505                 510

<210> SEQ ID NO 13
<211> LENGTH: 257
<212> TYPE: PRT
<213> ORGANISM: Escherichia coli -continued

```
<400> SEQUENCE: 13

Met Ile Lys Arg Thr Leu Leu Ala Ala Ile Phe Ser Ala Leu Pro
1               5                   10                  15

Ala Tyr Ala Gly Leu Thr Ser Ile Thr Ala Gly Tyr Asp Phe Thr Asp
            20                  25                  30

Tyr Ser Gly Asp His Gly Asn Arg Asn Leu Ala Tyr Ala Glu Leu Val
        35                  40                  45

Ala Lys Val Glu Asn Ala Thr Leu Leu Phe Asn Leu Ser Gln Gly Arg
50                  55                  60

Arg Asp Tyr Glu Thr Glu His Phe Asn Ala Thr Arg Gly Gln Gly Ala
65                  70                  75                  80

Val Trp Tyr Lys Trp Asn Asn Trp Leu Thr Thr Arg Thr Gly Ile Ala
                85                  90                  95

Phe Ala Asp Asn Thr Pro Val Phe Ala Arg Gln Asp Phe Arg Gln Asp
            100                 105                 110

Ile Asn Leu Ala Leu Leu Pro Lys Thr Leu Phe Thr Thr Gly Tyr Arg
        115                 120                 125

Tyr Thr Lys Tyr Tyr Asp Asp Val Glu Val Asp Ala Trp Gln Gly Gly
130                 135                 140

Val Ser Leu Tyr Thr Gly Pro Val Ile Thr Ser Tyr Arg Tyr Thr His
145                 150                 155                 160

Tyr Asp Ser Ser Asp Ala Gly Gly Ser Tyr Ser Asn Met Ile Ser Val
                165                 170                 175

Arg Leu Asn Asp Pro Arg Gly Thr Gly Tyr Thr Gln Leu Trp Leu Ser
            180                 185                 190

Arg Gly Thr Gly Ala Tyr Thr Tyr Asp Trp Thr Pro Glu Thr Arg Tyr
        195                 200                 205

Gly Ser Met Lys Ser Val Ser Leu Gln Arg Ile Gln Pro Leu Thr Glu
210                 215                 220

Gln Leu Asn Leu Gly Leu Thr Ala Gly Lys Val Trp Tyr Asp Thr Pro
225                 230                 235                 240

Thr Asp Asp Tyr Asn Gly Leu Gln Leu Ala Ala His Leu Thr Trp Lys
                245                 250                 255

Phe

<210> SEQ ID NO 14
<211> LENGTH: 91
<212> TYPE: PRT
<213> ORGANISM: Escherichia coli

<400> SEQUENCE: 14

Met Pro Ser Thr Pro Glu Glu Lys Lys Lys Val Leu Thr Arg Val Arg
1               5                   10                  15

Arg Ile Arg Gly Gln Ile Asp Ala Leu Glu Arg Ser Leu Glu Gly Asp
            20                  25                  30

Ala Glu Cys Arg Ala Ile Leu Gln Gln Ile Ala Ala Val Arg Gly Ala
        35                  40                  45

Ala Asn Gly Leu Met Ala Glu Val Leu Glu Ser His Ile Arg Glu Thr
50                  55                  60

Phe Asp Arg Asn Asp Cys Tyr Ser Arg Glu Ser Gln Ser Val Asp
65                  70                  75                  80

Asp Thr Ile Glu Leu Val Arg Ala Tyr Leu Lys
                85                  90
```

<210> SEQ ID NO 15
<211> LENGTH: 369
<212> TYPE: PRT
<213> ORGANISM: Escherichia coli

<400> SEQUENCE: 15

| Met | Lys | Ser | Arg | Ala | Ala | Val | Ala | Phe | Ala | Pro | Gly | Lys | Pro | Leu | Glu |
|---|---|---|---|---|---|---|---|---|---|---|---|---|---|---|---|
| 1 | | | | 5 | | | | | 10 | | | | | 15 | |

| Ile | Val | Glu | Ile | Asp | Val | Ala | Pro | Pro | Lys | Lys | Gly | Glu | Val | Leu | Ile |
| | | | 20 | | | | | 25 | | | | | 30 | | |

| Lys | Val | Thr | His | Thr | Gly | Val | Cys | His | Thr | Asp | Ala | Phe | Thr | Leu | Ser |
| | | | 35 | | | | | 40 | | | | | 45 | | |

| Gly | Asp | Asp | Pro | Glu | Gly | Val | Phe | Pro | Val | Val | Leu | Gly | His | Glu | Gly |
| | 50 | | | | | 55 | | | | | 60 | | | | |

| Ala | Gly | Val | Val | Glu | Val | Gly | Glu | Gly | Val | Thr | Ser | Val | Lys | Pro |
| 65 | | | | | 70 | | | | | 75 | | | | 80 |

| Gly | Asp | His | Val | Ile | Pro | Leu | Tyr | Thr | Ala | Glu | Cys | Gly | Glu | Cys | Glu |
| | | | | 85 | | | | | 90 | | | | | 95 | |

| Phe | Cys | Arg | Ser | Gly | Lys | Thr | Asn | Leu | Cys | Val | Ala | Val | Arg | Glu | Thr |
| | | | 100 | | | | | 105 | | | | | 110 | | |

| Gln | Gly | Lys | Gly | Leu | Met | Pro | Asp | Gly | Thr | Thr | Arg | Phe | Ser | Tyr | Asn |
| | | | 115 | | | | | 120 | | | | | 125 | | |

| Gly | Gln | Pro | Leu | Tyr | His | Tyr | Met | Gly | Cys | Ser | Thr | Phe | Ser | Glu | Tyr |
| | 130 | | | | | 135 | | | | | 140 | | | | |

| Thr | Val | Val | Ala | Glu | Val | Ser | Leu | Ala | Lys | Ile | Asn | Pro | Glu | Ala | Asn |
| 145 | | | | | 150 | | | | | 155 | | | | | 160 |

| His | Glu | His | Val | Cys | Leu | Leu | Gly | Cys | Gly | Val | Thr | Thr | Gly | Ile | Gly |
| | | | | 165 | | | | | 170 | | | | | 175 | |

| Ala | Val | His | Asn | Thr | Ala | Lys | Val | Gln | Pro | Gly | Asp | Ser | Val | Ala | Val |
| | | | 180 | | | | | 185 | | | | | 190 | | |

| Phe | Gly | Leu | Gly | Ala | Ile | Gly | Leu | Ala | Val | Val | Gln | Gly | Ala | Arg | Gln |
| | | | 195 | | | | | 200 | | | | | 205 | | |

| Ala | Lys | Ala | Gly | Arg | Ile | Ile | Ala | Ile | Asp | Thr | Asn | Pro | Lys | Lys | Phe |
| | 210 | | | | | 215 | | | | | 220 | | | | |

| Asp | Leu | Ala | Arg | Arg | Phe | Gly | Ala | Thr | Asp | Cys | Ile | Asn | Pro | Asn | Asp |
| 225 | | | | | 230 | | | | | 235 | | | | | 240 |

| Tyr | Asp | Lys | Pro | Ile | Lys | Asp | Val | Leu | Leu | Asp | Ile | Asn | Lys | Trp | Gly |
| | | | | 245 | | | | | 250 | | | | | 255 | |

| Ile | Asp | His | Thr | Phe | Glu | Cys | Ile | Gly | Asn | Val | Asn | Val | Met | Arg | Ala |
| | | | 260 | | | | | 265 | | | | | 270 | | |

| Ala | Leu | Glu | Ser | Ala | His | Arg | Gly | Trp | Gly | Gln | Ser | Val | Ile | Ile | Gly |
| | | | 275 | | | | | 280 | | | | | 285 | | |

| Val | Ala | Gly | Ala | Gly | Gln | Glu | Ile | Ser | Thr | Arg | Pro | Phe | Gln | Leu | Val |
| | 290 | | | | | 295 | | | | | 300 | | | | |

| Thr | Gly | Arg | Val | Trp | Lys | Gly | Ser | Ala | Phe | Gly | Gly | Val | Lys | Gly | Arg |
| 305 | | | | | 310 | | | | | 315 | | | | | 320 |

| Ser | Gln | Leu | Pro | Gly | Met | Val | Glu | Asp | Ala | Met | Lys | Gly | Asp | Ile | Asp |
| | | | | 325 | | | | | 330 | | | | | 335 | |

| Leu | Glu | Pro | Phe | Val | Thr | His | Thr | Met | Ser | Leu | Asp | Glu | Ile | Asn | Asp |
| | | | 340 | | | | | 345 | | | | | 350 | | |

| Ala | Phe | Asp | Leu | Met | His | Glu | Gly | Lys | Ser | Ile | Arg | Thr | Val | Ile | Arg |
| | | | 355 | | | | | 360 | | | | | 365 | | |

Tyr

-continued

```
<210> SEQ ID NO 16
<211> LENGTH: 277
<212> TYPE: PRT
<213> ORGANISM: Escherichia coli

<400> SEQUENCE: 16
```

| Met | Glu | Leu | Ile | Glu | Lys | His | Ala | Ser | Phe | Gly | Gly | Trp | Gln | Asn | Val |
|---|---|---|---|---|---|---|---|---|---|---|---|---|---|---|---|
| 1 | | | | 5 | | | | | 10 | | | | | 15 | |

| Tyr | Arg | His | Tyr | Ser | Gln | Ser | Leu | Lys | Cys | Glu | Met | Asn | Val | Gly | Val |
|---|---|---|---|---|---|---|---|---|---|---|---|---|---|---|---|
| | | | 20 | | | | | 25 | | | | | 30 | | |

| Tyr | Leu | Pro | Pro | Lys | Ala | Ala | Asn | Glu | Lys | Leu | Pro | Val | Leu | Tyr | Trp |
|---|---|---|---|---|---|---|---|---|---|---|---|---|---|---|---|
| | | | 35 | | | | | 40 | | | | | 45 | | |

| Leu | Ser | Gly | Leu | Thr | Cys | Asn | Glu | Gln | Asn | Phe | Ile | Thr | Lys | Ser | Gly |
|---|---|---|---|---|---|---|---|---|---|---|---|---|---|---|---|
| | 50 | | | | | 55 | | | | | 60 | | | | |

| Met | Gln | Arg | Tyr | Ala | Ala | Glu | His | Asn | Ile | Ile | Val | Val | Ala | Pro | Asp |
|---|---|---|---|---|---|---|---|---|---|---|---|---|---|---|---|
| 65 | | | | | 70 | | | | | 75 | | | | | 80 |

| Thr | Ser | Pro | Arg | Gly | Ser | His | Val | Ala | Asp | Ala | Asp | Arg | Tyr | Asp | Leu |
|---|---|---|---|---|---|---|---|---|---|---|---|---|---|---|---|
| | | | | 85 | | | | | 90 | | | | | 95 | |

| Gly | Gln | Gly | Ala | Gly | Phe | Tyr | Leu | Asn | Ala | Thr | Gln | Ala | Pro | Trp | Asn |
|---|---|---|---|---|---|---|---|---|---|---|---|---|---|---|---|
| | | | 100 | | | | | 105 | | | | | 110 | | |

| Glu | His | Tyr | Lys | Met | Tyr | Asp | Tyr | Ile | Arg | Asn | Glu | Leu | Pro | Asp | Leu |
|---|---|---|---|---|---|---|---|---|---|---|---|---|---|---|---|
| | | | 115 | | | | | 120 | | | | | 125 | | |

| Val | Met | His | His | Phe | Pro | Ala | Thr | Ala | Lys | Lys | Ser | Ile | Ser | Gly | His |
|---|---|---|---|---|---|---|---|---|---|---|---|---|---|---|---|
| | 130 | | | | | 135 | | | | | 140 | | | | |

| Ser | Met | Gly | Gly | Leu | Gly | Ala | Leu | Val | Leu | Ala | Leu | Arg | Asn | Pro | Asp |
|---|---|---|---|---|---|---|---|---|---|---|---|---|---|---|---|
| 145 | | | | | 150 | | | | | 155 | | | | | 160 |

| Glu | Tyr | Val | Ser | Val | Ser | Ala | Phe | Ser | Pro | Ile | Val | Ser | Pro | Ser | Gln |
|---|---|---|---|---|---|---|---|---|---|---|---|---|---|---|---|
| | | | | 165 | | | | | 170 | | | | | 175 | |

| Val | Pro | Trp | Gly | Gln | Gln | Ala | Phe | Ala | Ala | Tyr | Leu | Ala | Glu | Asn | Lys |
|---|---|---|---|---|---|---|---|---|---|---|---|---|---|---|---|
| | | | 180 | | | | | 185 | | | | | 190 | | |

| Asp | Ala | Trp | Leu | Asp | Tyr | Asp | Pro | Val | Ser | Leu | Ile | Ser | Gln | Gly | Gln |
|---|---|---|---|---|---|---|---|---|---|---|---|---|---|---|---|
| | | | 195 | | | | | 200 | | | | | 205 | | |

| Arg | Val | Ala | Glu | Ile | Met | Val | Asp | Gln | Gly | Leu | Ser | Asp | Asp | Phe | Tyr |
|---|---|---|---|---|---|---|---|---|---|---|---|---|---|---|---|
| | 210 | | | | | 215 | | | | | 220 | | | | |

| Ala | Glu | Gln | Leu | Arg | Thr | Pro | Asn | Leu | Glu | Lys | Ile | Cys | Gln | Glu | Met |
|---|---|---|---|---|---|---|---|---|---|---|---|---|---|---|---|
| 225 | | | | | 230 | | | | | 235 | | | | | 240 |

| Asn | Ile | Lys | Thr | Leu | Ile | Arg | Tyr | His | Glu | Gly | Tyr | Asp | His | Ser | Tyr |
|---|---|---|---|---|---|---|---|---|---|---|---|---|---|---|---|
| | | | | 245 | | | | | 250 | | | | | 255 | |

| Tyr | Phe | Val | Ser | Ser | Phe | Ile | Gly | Glu | His | Ile | Ala | Tyr | His | Ala | Asn |
|---|---|---|---|---|---|---|---|---|---|---|---|---|---|---|---|
| | | | 260 | | | | | 265 | | | | | 270 | | |

| Lys | Leu | Asn | Met | Arg |
|---|---|---|---|---|
| | | | | 275 |

```
<210> SEQ ID NO 17
<211> LENGTH: 179
<212> TYPE: PRT
<213> ORGANISM: Escherichia coli

<400> SEQUENCE: 17
```

| Met | Ala | Lys | Leu | Thr | Leu | Gln | Glu | Gln | Leu | Leu | Lys | Ala | Gly | Leu | Val |
|---|---|---|---|---|---|---|---|---|---|---|---|---|---|---|---|
| 1 | | | | 5 | | | | | 10 | | | | | 15 | |

| Thr | Ser | Lys | Lys | Ala | Ala | Lys | Val | Glu | Arg | Thr | Ala | Lys | Lys | Ser | Arg |
|---|---|---|---|---|---|---|---|---|---|---|---|---|---|---|---|
| | | | 20 | | | | | 25 | | | | | 30 | | |

| Val | Gln | Ala | Arg | Glu | Ala | Arg | Ala | Val | Glu | Glu | Asn | Lys | Lys | Ala |
|---|---|---|---|---|---|---|---|---|---|---|---|---|---|---|
| | | | 35 | | | | | 40 | | | | | 45 | |

```
Gln Leu Glu Arg Asp Lys Gln Leu Ser Glu Gln Gln Lys Gln Ala Ala
         50                  55                  60

Leu Ala Lys Glu Tyr Lys Ala Gln Val Lys Gln Leu Ile Glu Met Asn
 65                  70                  75                  80

Arg Ile Thr Ile Ala Asn Gly Asp Ile Gly Phe Asn Phe Thr Asp Gly
                 85                  90                  95

Asn Leu Ile Lys Lys Ile Phe Val Asp Lys Leu Thr Gln Ala Gln Leu
                100                 105                 110

Ile Asn Gly Arg Leu Ala Ile Ala Arg Leu Leu Val Asp Asn Asn Ser
            115                 120                 125

Glu Gly Glu Tyr Ala Ile Ile Pro Ala Ser Val Ala Asp Lys Ile Ala
        130                 135                 140

Gln Arg Asp Ala Ser Ser Ile Val Leu His Ser Ala Leu Ser Ala Glu
145                 150                 155                 160

Glu Gln Asp Glu Asp Asp Pro Tyr Ala Asp Phe Lys Val Pro Asp Asp
                165                 170                 175

Leu Met Trp

<210> SEQ ID NO 18
<211> LENGTH: 403
<212> TYPE: PRT
<213> ORGANISM: Escherichia coli

<400> SEQUENCE: 18

Met Ser Thr Arg Thr Pro Ser Ser Ser Ser Arg Leu Met Leu Thr
 1               5                  10                  15

Ile Gly Leu Cys Phe Leu Val Ala Leu Met Glu Gly Leu Asp Leu Gln
                 20                  25                  30

Ala Ala Gly Ile Ala Ala Gly Gly Ile Ala Gln Ala Phe Ala Leu Asp
             35                  40                  45

Lys Met Gln Met Gly Trp Ile Phe Ser Ala Gly Ile Leu Gly Leu Leu
 50                  55                  60

Pro Gly Ala Leu Val Gly Gly Met Leu Ala Asp Arg Tyr Gly Arg Lys
 65                  70                  75                  80

Arg Ile Leu Ile Gly Ser Val Ala Leu Phe Gly Leu Phe Ser Leu Ala
                 85                  90                  95

Thr Ala Ile Ala Trp Asp Phe Pro Ser Leu Val Phe Ala Arg Leu Met
                100                 105                 110

Thr Gly Val Gly Leu Gly Ala Ala Leu Pro Asn Leu Ile Ala Leu Thr
            115                 120                 125

Ser Glu Ala Ala Gly Pro Arg Phe Arg Gly Thr Ala Val Ser Leu Met
130                 135                 140

Tyr Cys Gly Val Pro Ile Gly Ala Ala Leu Ala Ala Thr Leu Gly Phe
145                 150                 155                 160

Ala Gly Ala Asn Leu Ala Trp Gln Thr Val Phe Trp Val Gly Gly Val
                165                 170                 175

Val Pro Leu Ile Leu Val Pro Leu Leu Met Arg Trp Leu Pro Glu Ser
            180                 185                 190

Ala Val Phe Ala Gly Glu Lys Gln Ser Ala Pro Pro Leu Arg Ala Leu
        195                 200                 205

Phe Ala Pro Glu Thr Ala Thr Ala Thr Leu Leu Leu Trp Leu Cys Tyr
    210                 215                 220

Phe Phe Thr Leu Leu Val Val Tyr Met Leu Ile Asn Trp Leu Pro Leu
225                 230                 235                 240
```

```
Leu Leu Val Glu Gln Gly Phe Gln Pro Ser Gln Ala Ala Gly Val Met
                245                 250                 255

Phe Ala Leu Gln Met Gly Ala Ala Ser Gly Thr Leu Met Leu Gly Ala
            260                 265                 270

Leu Met Asp Lys Leu Arg Pro Val Thr Met Ser Leu Leu Ile Tyr Ser
        275                 280                 285

Gly Met Leu Ala Ser Leu Leu Ala Leu Gly Thr Val Ser Ser Phe Asn
    290                 295                 300

Gly Met Leu Leu Ala Gly Phe Val Ala Gly Leu Phe Ala Thr Gly Gly
305                 310                 315                 320

Gln Ser Val Leu Tyr Ala Leu Ala Pro Leu Phe Tyr Ser Ser Gln Ile
                325                 330                 335

Arg Ala Thr Gly Val Gly Thr Ala Val Ala Val Gly Arg Leu Gly Ala
            340                 345                 350

Met Ser Gly Pro Leu Leu Ala Gly Lys Met Leu Ala Leu Gly Thr Gly
        355                 360                 365

Thr Val Gly Val Met Ala Ala Ser Ala Pro Gly Ile Leu Val Ala Gly
    370                 375                 380

Leu Ala Val Phe Ile Leu Met Ser Arg Arg Ser Arg Ile Gln Pro Cys
385                 390                 395                 400

Ala Asp Ala

<210> SEQ ID NO 19
<211> LENGTH: 337
<212> TYPE: PRT
<213> ORGANISM: Escherichia coli

<400> SEQUENCE: 19

Met Asn Gly Lys Lys Leu Tyr Ile Ser Asp Val Thr Leu Arg Asp Gly
1               5                   10                  15

Met His Ala Ile Arg His Gln Tyr Ser Leu Glu Asn Val Arg Gln Ile
            20                  25                  30

Ala Lys Ala Leu Asp Asp Ala His Val Asp Ser Ile Glu Val Ala His
        35                  40                  45

Gly Asp Gly Leu Gln Gly Ser Ser Phe Asn Tyr Gly Phe Gly Ala His
    50                  55                  60

Ser Asp Leu Glu Trp Ile Glu Ala Ala Asp Val Val Lys His Ala
65                  70                  75                  80

Lys Ile Ala Thr Leu Leu Pro Gly Ile Gly Thr Ile His Asp Leu
                85                  90                  95

Lys Asn Ala Trp Gln Ala Gly Ala Arg Val Val Arg Val Ala Thr His
            100                 105                 110

Cys Thr Glu Ala Asp Val Ser Ala Gln His Ile Gln Tyr Ala Arg Glu
        115                 120                 125

Leu Gly Met Asp Thr Val Gly Phe Leu Met Met Ser His Met Thr Thr
    130                 135                 140

Pro Glu Asn Leu Ala Lys Gln Ala Lys Leu Met Glu Gly Tyr Gly Ala
145                 150                 155                 160

Thr Cys Ile Tyr Val Val Asp Ser Gly Gly Ala Met Asn Met Ser Asp
                165                 170                 175

Ile Arg Asp Arg Phe Arg Ala Leu Lys Ala Val Leu Lys Pro Glu Thr
            180                 185                 190

Gln Thr Gly Met His Ala His His Asn Leu Ser Leu Gly Val Ala Asn
        195                 200                 205
```

```
Ser Ile Glu Ala Val Glu Gly Cys Asp Arg Ile Asp Ala Ser Leu
    210                 215                 220

Ala Gly Met Gly Ala Gly Ala Gly Asn Ala Pro Leu Glu Val Phe Ile
225                 230                 235                 240

Ala Ala Ala Asp Lys Leu Gly Trp Gln His Gly Thr Asp Leu Tyr Ala
                245                 250                 255

Leu Met Asp Ala Ala Asp Asp Leu Val Arg Pro Leu Gln Asp Arg Pro
                260                 265                 270

Val Arg Val Asp Arg Glu Thr Leu Ala Leu Gly Tyr Ala Gly Val Tyr
            275                 280                 285

Ser Ser Phe Leu Arg His Cys Glu Thr Ala Ala Arg Tyr Gly Leu
            290                 295                 300

Ser Ala Val Asp Ile Leu Val Glu Leu Gly Lys Arg Arg Met Val Gly
305                 310                 315                 320

Gly Gln Glu Asp Met Ile Val Asp Val Ala Leu Asp Leu Arg Asn Asn
                    325                 330                 335

Lys

<210> SEQ ID NO 20
<211> LENGTH: 316
<212> TYPE: PRT
<213> ORGANISM: Escherichia coli

<400> SEQUENCE: 20

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
                20                  25                  30

Val Met Val Gly Ile Asp Pro Gln Ser Asp Gly Leu Ala Arg Ala Arg
            35                  40                  45

Arg Met Gly Val Ala Thr Thr His Glu Gly Val Ile Gly Leu Met Asn
        50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
210                 215                 220

Ser Ile Asn Glu Met Ala Glu Ala Val Gln Ala Tyr Val Pro Gly Tyr
225                 230                 235                 240
```

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
                260                 265                 270

Trp Leu Glu Val Glu Gly Ala Ala His Tyr Leu Pro Ala Tyr Ala Gly
                275                 280                 285

Asn Leu Asp Ile Met Thr Ser Ser Ala Leu Ala Thr Ala Glu Lys Met
                290                 295                 300

Ala Gln Ser Leu Ala Arg Lys Ala Gly Glu Ala Ala
305                 310                 315

<210> SEQ ID NO 21
<211> LENGTH: 269
<212> TYPE: PRT
<213> ORGANISM: Escherichia coli

<400> SEQUENCE: 21

Met Thr Lys His Thr Leu Glu Gln Leu Ala Ala Asp Leu Arg Arg Ala
1               5                   10                  15

Ala Glu Gln Gly Glu Ala Ile Ala Pro Leu Arg Asp Leu Ile Gly Ile
                20                  25                  30

Asp Asn Ala Glu Ala Ala Tyr Ala Ile Gln His Ile Asn Val Gln Tyr
            35                  40                  45

Asp Val Ala Gln Gly Arg Arg Val Val Gly Arg Lys Val Gly Leu Thr
        50                  55                  60

His Pro Lys Val Gln Gln Gln Leu Gly Val Asp Gln Pro Asp Phe Gly
65                  70                  75                  80

Thr Leu Phe Ala Asp Met Cys Tyr Gly Asp Asn Glu Ile Ile Pro Phe
                85                  90                  95

Ser Arg Val Leu Gln Pro Arg Ile Glu Ala Glu Ile Ala Leu Val Leu
                100                 105                 110

Asn Arg Asp Leu Pro Ala Thr Asp Ile Thr Phe Asp Glu Leu Tyr Asn
            115                 120                 125

Ala Ile Glu Trp Val Leu Pro Ala Leu Glu Val Val Gly Ser Arg Ile
        130                 135                 140

Arg Asp Trp Ser Ile Gln Phe Val Asp Thr Val Ala Asp Asn Ala Ser
145                 150                 155                 160

Cys Gly Val Tyr Val Ile Gly Gly Pro Ala Gln Arg Pro Ala Gly Leu
                165                 170                 175

Asp Leu Lys Asn Cys Ala Met Lys Met Thr Arg Asn Asn Glu Glu Val
                180                 185                 190

Ser Ser Gly Arg Gly Ser Glu Cys Leu Gly His Pro Leu Asn Ala Ala
            195                 200                 205

Val Trp Leu Ala Arg Lys Met Ala Ser Leu Gly Glu Pro Leu Arg Thr
        210                 215                 220

Gly Asp Ile Ile Leu Thr Gly Ala Leu Gly Pro Met Val Ala Val Asn
225                 230                 235                 240

Ala Gly Asp Arg Phe Glu Ala His Ile Glu Gly Ile Gly Ser Val Ala
                245                 250                 255

Ala Thr Phe Ser Ser Ala Ala Pro Lys Gly Ser Leu Ser
                260                 265

<210> SEQ ID NO 22
<211> LENGTH: 293
<212> TYPE: PRT

<213> ORGANISM: Escherichia coli

<400> SEQUENCE: 22

Met Gln Glu Lys Met Met Ser Tyr Gln Pro Gln Thr Glu Ala Ala Thr
1               5                   10                  15

Ser Arg Phe Leu Asn Val Glu Glu Ala Gly Lys Thr Leu Arg Ile His
            20                  25                  30

Phe Asn Asp Cys Gly Gln Gly Asp Glu Thr Val Val Leu Leu His Gly
        35                  40                  45

Ser Gly Pro Gly Ala Thr Gly Trp Ala Asn Phe Ser Arg Asn Ile Asp
    50                  55                  60

Pro Leu Val Glu Ala Gly Tyr Arg Val Ile Leu Leu Asp Cys Pro Gly
65                  70                  75                  80

Trp Gly Lys Ser Asp Ser Ile Val Asn Ser Gly Ser Arg Ser Asp Leu
                85                  90                  95

Asn Ala Arg Ile Leu Lys Ser Val Val Asp Gln Leu Asp Ile Ala Lys
            100                 105                 110

Ile His Leu Leu Gly Asn Ser Met Gly Gly His Ser Ser Val Ala Phe
        115                 120                 125

Thr Leu Asn Trp Pro Glu Arg Val Gly Lys Leu Val Leu Met Gly Gly
    130                 135                 140

Gly Thr Gly Gly Met Ser Leu Phe Thr Pro Met Pro Thr Glu Gly Ile
145                 150                 155                 160

Lys Arg Leu Asn Gln Leu Tyr Arg Gln Pro Thr Ile Glu Asn Leu Lys
                165                 170                 175

Leu Met Met Asp Ile Phe Val Phe Asp Thr Ser Asp Leu Thr Asp Ala
            180                 185                 190

Leu Phe Glu Ala Arg Leu Asn Asn Met Leu Ser Arg Arg Asp His Leu
        195                 200                 205

Glu Asn Phe Val Lys Ser Leu Glu Ala Asn Pro Lys Gln Phe Pro Asp
    210                 215                 220

Phe Gly Pro Arg Leu Ala Glu Ile Lys Ala Gln Thr Leu Ile Val Trp
225                 230                 235                 240

Gly Arg Asn Asp Arg Phe Val Pro Met Asp Ala Gly Leu Arg Leu Leu
                245                 250                 255

Ser Gly Ile Ala Gly Ser Glu Leu His Ile Phe Arg Asp Cys Gly His
            260                 265                 270

Trp Ala Gln Trp Glu His Ala Asp Ala Phe Asn Gln Leu Val Leu Asn
        275                 280                 285

Phe Leu Ala Arg Pro
    290

<210> SEQ ID NO 23
<211> LENGTH: 314
<212> TYPE: PRT
<213> ORGANISM: Escherichia coli

<400> SEQUENCE: 23

Met His Ala Tyr Leu His Cys Leu Ser His Ser Pro Leu Val Gly Tyr
1               5                   10                  15

Val Asp Pro Ala Gln Glu Val Leu Asp Glu Val Asn Gly Val Ile Ala
            20                  25                  30

Ser Ala Arg Glu Arg Ile Ala Ala Phe Ser Pro Glu Leu Val Val Leu
        35                  40                  45

```
Phe Ala Pro Asp His Tyr Asn Gly Phe Phe Tyr Asp Val Met Pro Pro
    50                  55                  60
Phe Cys Leu Gly Val Gly Ala Thr Ala Ile Gly Asp Phe Gly Ser Ala
65                  70                  75                  80
Ala Gly Glu Leu Pro Val Pro Val Glu Leu Ala Glu Ala Cys Ala His
                85                  90                  95
Ala Val Met Lys Ser Gly Ile Asp Leu Ala Val Ser Tyr Cys Met Gln
            100                 105                 110
Val Asp His Gly Phe Ala Gln Pro Leu Glu Phe Leu Leu Gly Gly Leu
        115                 120                 125
Asp Lys Val Pro Val Leu Pro Val Phe Ile Asn Gly Val Ala Thr Pro
    130                 135                 140
Leu Pro Gly Phe Gln Arg Thr Arg Met Leu Gly Glu Ala Ile Gly Arg
145                 150                 155                 160
Phe Thr Ser Thr Leu Asn Lys Arg Val Leu Phe Leu Gly Ser Gly Gly
                165                 170                 175
Leu Ser His Gln Pro Pro Val Pro Glu Leu Ala Lys Ala Asp Ala His
            180                 185                 190
Met Arg Asp Arg Leu Leu Gly Ser Gly Lys Asp Leu Pro Ala Ser Glu
        195                 200                 205
Arg Glu Leu Arg Gln Gln Arg Val Ile Ser Ala Glu Lys Phe Val
    210                 215                 220
Glu Asp Gln Arg Thr Leu His Pro Leu Asn Pro Ile Trp Asp Asn Gln
225                 230                 235                 240
Phe Met Thr Leu Leu Glu Gln Gly Arg Ile Gln Glu Leu Asp Ala Val
                245                 250                 255
Ser Asn Glu Glu Leu Ser Ala Ile Ala Gly Lys Ser Thr His Glu Ile
            260                 265                 270
Lys Thr Trp Val Ala Ala Phe Ala Ala Ile Ser Ala Phe Gly Asn Trp
        275                 280                 285
Arg Ser Glu Gly Arg Tyr Tyr Arg Pro Ile Pro Glu Trp Ile Ala Gly
    290                 295                 300
Phe Gly Ser Leu Ser Ala Arg Thr Glu Asn
305                 310

<210> SEQ ID NO 24
<211> LENGTH: 554
<212> TYPE: PRT
<213> ORGANISM: Escherichia coli

<400> SEQUENCE: 24

Met Ala Ile Gln His Pro Asp Ile Gln Pro Ala Val Asn His Ser Val
1               5                   10                  15
Gln Val Ala Ile Ala Gly Ala Gly Pro Val Gly Leu Met Met Ala Asn
            20                  25                  30
Tyr Leu Gly Gln Met Gly Ile Asp Val Leu Val Glu Lys Leu Asp
        35                  40                  45
Lys Leu Ile Asp Tyr Pro Arg Ala Ile Gly Ile Asp Asp Glu Ala Leu
    50                  55                  60
Arg Thr Met Gln Ser Val Gly Leu Val Asp Asp Val Leu Pro His Thr
65                  70                  75                  80
Thr Pro Trp His Ala Met Arg Phe Leu Thr Pro Lys Gly Arg Cys Phe
                85                  90                  95
```

-continued

Ala Asp Ile Gln Pro Met Thr Asp Glu Phe Gly Trp Pro Arg Arg Asn
            100                 105                 110

Ala Phe Ile Gln Pro Gln Val Asp Ala Val Met Leu Glu Gly Val Ser
            115                 120                 125

Arg Phe Pro Asn Val Arg Cys Leu Phe Ser Arg Glu Leu Glu Ala Phe
130                 135                 140

Ser Gln Gln Asp Asp Glu Val Thr Leu His Leu Lys Thr Ala Glu Gly
145                 150                 155                 160

Gln Arg Glu Ile Val Lys Ala Gln Trp Leu Val Ala Cys Asp Gly Gly
                165                 170                 175

Ala Ser Phe Val Arg Arg Thr Leu Asn Val Pro Phe Glu Gly Lys Thr
            180                 185                 190

Ala Pro Asn Gln Trp Ile Val Val Asp Ile Ala Asn Asp Pro Leu Ser
            195                 200                 205

Thr Pro His Ile Tyr Leu Cys Cys Asp Pro Val Arg Pro Tyr Val Ser
            210                 215                 220

Ala Ala Leu Pro His Ala Val Arg Arg Phe Glu Phe Met Val Met Pro
225                 230                 235                 240

Gly Glu Thr Glu Glu Gln Leu Arg Glu Pro Gln Asn Met Arg Lys Leu
                245                 250                 255

Leu Ser Lys Val Leu Pro Asn Pro Asp Asn Val Glu Leu Ile Arg Gln
            260                 265                 270

Arg Val Tyr Thr His Asn Ala Arg Leu Ala Gln Arg Phe Arg Ile Asp
            275                 280                 285

Arg Val Leu Leu Ala Gly Asp Ala Ala His Ile Met Pro Val Trp Gln
290                 295                 300

Gly Gln Gly Tyr Asn Ser Gly Met Arg Asp Ala Phe Asn Leu Ala Trp
305                 310                 315                 320

Lys Leu Ala Leu Val Ile Gln Gly Lys Ala Arg Asp Ala Leu Leu Asp
                325                 330                 335

Thr Tyr Gln Gln Glu Arg Arg Asp His Ala Lys Ala Met Ile Asp Leu
            340                 345                 350

Ser Val Thr Ala Gly Asn Val Leu Ala Pro Pro Lys Arg Trp Gln Gly
            355                 360                 365

Thr Leu Arg Asp Gly Val Ser Trp Leu Leu Asn Tyr Leu Pro Pro Val
370                 375                 380

Lys Arg Tyr Phe Leu Glu Met Arg Phe Lys Pro Met Pro Gln Tyr Tyr
385                 390                 395                 400

Gly Gly Ala Leu Val Arg Glu Gly Glu Ala Lys His Ser Pro Val Gly
                405                 410                 415

Lys Met Phe Ile Gln Pro Lys Val Thr Leu Glu Asn Gly Asp Val Thr
            420                 425                 430

Leu Leu Asp Asn Ala Ile Gly Ala Asn Phe Ala Val Ile Gly Trp Gly
            435                 440                 445

Cys Asn Pro Leu Trp Gly Met Ser Asp Glu Gln Ile Gln Gln Trp Arg
450                 455                 460

Ala Leu Gly Thr Arg Phe Ile Gln Val Val Pro Glu Val Gln Ile His
465                 470                 475                 480

Thr Ala Gln Asp Asn His Asp Gly Val Leu Arg Val Gly Asp Thr Gln
                485                 490                 495

Gly Arg Leu Arg Ser Trp Phe Ala Gln His Asn Ala Ser Leu Val Val
            500                 505                 510

Met Arg Pro Asp Arg Phe Val Ala Thr Ala Ile Pro Gln Thr Leu
            515                 520                 525

Gly Asn Thr Leu Asn Lys Leu Ala Ser Val Met Thr Leu Thr Arg Pro
530                 535                 540

Asp Ala Asp Val Ser Val Glu Lys Val Ala
545                 550

<210> SEQ ID NO 25
<211> LENGTH: 315
<212> TYPE: PRT
<213> ORGANISM: Escherichia coli

<400> SEQUENCE: 25

Met Ile Phe Tyr Cys Ala Leu Ser Ile Gly Arg Val Phe Ser Ala Thr
1               5                   10                  15

Ile Lys Thr Cys Pro Asn Val His Gln Val His His Val Val Leu Thr
            20                  25                  30

Ile Glu Met Ser Ile Asn Met Gln Asn Asn Glu Gln Thr Glu Tyr Lys
        35                  40                  45

Thr Val Arg Gly Leu Thr Arg Gly Leu Met Leu Leu Asn Met Leu Asn
    50                  55                  60

Lys Leu Asp Gly Gly Ala Ser Val Gly Leu Leu Ala Glu Leu Ser Gly
65                  70                  75                  80

Leu His Arg Thr Thr Val Arg Arg Leu Leu Glu Thr Leu Gln Glu Glu
                85                  90                  95

Gly Tyr Val Arg Arg Ser Pro Ser Asp Asp Ser Phe Arg Leu Thr Ile
            100                 105                 110

Lys Val Arg Gln Leu Ser Glu Gly Phe Arg Asp Glu Gln Trp Ile Ser
            115                 120                 125

Ala Leu Ala Ala Pro Leu Leu Gly Asp Leu Leu Arg Glu Val Val Trp
        130                 135                 140

Pro Thr Asp Val Ser Thr Leu Asp Val Asp Ala Met Val Val Arg Glu
145                 150                 155                 160

Thr Thr His Arg Phe Ser Arg Leu Ser Phe His Arg Ala Met Val Gly
                165                 170                 175

Arg Arg Leu Pro Leu Leu Lys Thr Ala Ser Gly Leu Thr Trp Leu Ala
            180                 185                 190

Phe Cys Pro Glu Gln Asp Arg Lys Glu Leu Ile Glu Met Leu Ala Ser
            195                 200                 205

Arg Pro Gly Asp Asp Tyr Gln Leu Ala Arg Glu Pro Leu Lys Leu Glu
        210                 215                 220

Ala Ile Leu Ala Arg Ala Arg Lys Glu Gly Tyr Gly Gln Asn Tyr Arg
225                 230                 235                 240

Gly Trp Asp Gln Glu Glu Lys Ile Ala Ser Ile Ala Val Pro Leu Arg
                245                 250                 255

Ser Glu Gln Arg Val Ile Gly Cys Leu Asn Leu Val Tyr Met Ala Ser
            260                 265                 270

Ala Met Thr Ile Glu Gln Ala Ala Glu Lys His Leu Pro Ala Leu Gln
            275                 280                 285

Arg Val Ala Lys Gln Ile Glu Glu Gly Val Glu Ser Gln Ala Ile Leu
        290                 295                 300

Val Ala Gly Arg Arg Ser Gly Met His Leu Arg
305                 310                 315

<210> SEQ ID NO 26

```
<211> LENGTH: 360
<212> TYPE: PRT
<213> ORGANISM: Escherichia coli

<400> SEQUENCE: 26

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 27
<211> LENGTH: 353
<212> TYPE: PRT
```

-continued

<213> ORGANISM: Escherichia coli

<400> SEQUENCE: 27

Met Ala Ile Asp Glu Asn Lys Gln Lys Ala Leu Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Glu Thr Ile Ser Thr Gly Ser Leu Ser Leu
        35                  40                  45

Asp Ile Ala Leu Gly Ala Gly Gly Leu Pro Met Gly Arg Ile Val Glu
    50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
            100                 105                 110

Asp Asn Leu Leu Cys Ser Gln Pro Asp Thr Gly Glu Gln Ala Leu Glu
        115                 120                 125

Ile Cys Asp Ala Leu Ala Arg Ser Gly Ala Val Asp Val Ile Val Val
    130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Tyr
            260                 265                 270

Gly Glu Leu Val Asp Leu Gly Val Lys Glu Lys Leu Ile Glu Lys Ala
        275                 280                 285

Gly Ala Trp Tyr Ser Tyr Lys Gly Glu Lys Ile Gly Gln Gly Lys Ala
    290                 295                 300

Asn Ala Thr Ala Trp Leu Lys Asp Asn Pro Glu Thr Ala Lys Glu Ile
305                 310                 315                 320

Glu Lys Lys Val Arg Glu Leu Leu Leu Ser Asn Pro Asn Ser Thr Pro
                325                 330                 335

Asp Phe Ser Val Asp Asp Ser Glu Gly Val Ala Glu Thr Asn Glu Asp
            340                 345                 350

Phe

<210> SEQ ID NO 28
<211> LENGTH: 49
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 28
ctgtataaaa ccacagccaa tcaaacgaaa ccaggctata ctcaagcct          49

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
ttttataaat acacagccaa tcaaacgaaa ccaggctata ctcaagcct          49

<210> SEQ ID NO 30
<211> LENGTH: 133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
ctcagcggtg gcagcagcct aggttaacta cttttctttg ttggtctttg cctccatttt     60
gtcggcctgg taatgactcc aacttattga tagtgtttta tgttcagata atgcccgatg    120
actttgtcat gca                                                       133

<210> SEQ ID NO 31
<211> LENGTH: 133
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (22)..(22)
<223> OTHER INFORMATION: a, c, t, g, unknown or other

<400> SEQUENCE: 31
ctcagcggtg gcagcagcct angttaatca tttttctttg ttggttttgg cttccatttt     60
atctgcttgg taatgactcc aacttattga tagtgtttta tgttcagata atgcccgatg    120
actttgtcat gca                                                       133

<210> SEQ ID NO 32
<211> LENGTH: 133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
ctcagcggtg gcagcagcct aggttaatca tttttctttg ttggttttgg cttccatttt     60
atctgcttgg taatgactcc aacttattga tagtgtttta tgttcagata atgcccgatg    120
actttgtcat gca                                                       133